US 8,658,665 B2

(12) United States Patent
Clunas et al.

(10) Patent No.: US 8,658,665 B2
(45) Date of Patent: Feb. 25, 2014

(54) 3,6-DISUBSTITUTED XANTHYLIUM SALTS AND USE THEREOF IN TREATMENT OF TAUOPATHIES

(75) Inventors: Scott Clunas, Old Aberdeen (GB); John Mervyn David Storey, Old Aberdeen (GB); Janet Elizabeth Rickard, Aberdeen (GB); David Horsley, Aberdeen (GB); Charles Robert Harrington, Aberdeen (GB); Claude Michel Wischik, Aberdeen (GB)

(73) Assignee: WisTa Laboratories Ltd., Singapore (SG)

( * ) Notice: Subject to any disclaimer, the term of this patent is extended or adjusted under 35 U.S.C. 154(b) by 33 days.

(21) Appl. No.: 13/133,868

(22) PCT Filed: Dec. 10, 2009

(86) PCT No.: PCT/GB2009/002865
§ 371 (c)(1),
(2), (4) Date: Jun. 9, 2011

(87) PCT Pub. No.: WO2010/067078
PCT Pub. Date: Jun. 17, 2010

(65) Prior Publication Data
US 2011/0300074 A1    Dec. 8, 2011

Related U.S. Application Data

(60) Provisional application No. 61/121,288, filed on Dec. 10, 2008.

(51) Int. Cl.
*A61K 31/44*       (2006.01)
*C07D 491/00*     (2006.01)
(52) U.S. Cl.
USPC ............. 514/279; 514/277; 546/35; 546/34; 546/33; 546/26
(58) Field of Classification Search
None
See application file for complete search history.

(56) References Cited

U.S. PATENT DOCUMENTS

| | | | |
|---|---|---|---|
| 3,932,415 A | 1/1976 | Reynolds | |
| 6,953,794 B2 * | 10/2005 | Wischik et al. | ............ 514/224.8 |
| 2006/0240007 A1 * | 10/2006 | Sanders | ............... 424/144.1 |

FOREIGN PATENT DOCUMENTS

| | | |
|---|---|---|
| DE | 3322945 A1 | 1/1985 |
| EP | 0 805 441 B1 | 11/1997 |
| JP | 2004-61947 | 2/2004 |
| WO | WO 96/30766 | 10/1996 |
| WO | WO 2007/110627 A2 | 10/2007 |
| WO | WO 2007/110630 A1 | 10/2007 |

OTHER PUBLICATIONS

Clark et al., "Red edge photophysics of ethanolic rhodamine 101 and the observation of laser cooling in the condensed phase," J. Physical Chem. A, 1998, pp. 4428-4437, vol. 102, No. 24.
Ramos et al., "1H and 13C NMR spectra of commercial rhodamine ester derivatives," Magnetic Resonance in Chem., 2000, pp. 475-478, vol. 38, No. 6.
Jiao et al., "Microwave-assisted syntheses of regioisomerically pure bromorhodamine derivatives," Organic Letters, 2003, pp. 3675-3677, vol. 5, No. 20.
The International Search Report for the corresponding International Patent Application PCT/GB2009/002865, dated Oct. 5, 2010.
Jae K. Ryu, A leaky blood-brain barrier, fibrinogen infiltration and microglial reactivity in inflamed Alzheimer's disease brain, Journal of Cellular and Molecular Medicine, vol. 13, Issue 9a, pp. 2911-2925, Sep. 2009 (printed from Internet).
Effect of intraperitoneal administration of WL0090 (0.5 and 2 mg/kg) on scopolamine-induced cognitive deficit in NMRI wild-type mice aged 2-3 months, (2006).
Histological Study of Line 66 Homozygotic Mice treated with WL0090.

* cited by examiner

*Primary Examiner* — Brandon Fetterolf
*Assistant Examiner* — Theodore R West
(74) *Attorney, Agent, or Firm* — Foley & Lardner LLP

(57) ABSTRACT

This invention pertains generally to processes, uses, methods and materials utilizing particular xanthylium compounds, including compounds of formula (I) and (II), as further defined herein. These compounds are useful as drugs, for example, in the treatment of tauopathies, such as Alzheimer's disease.

22 Claims, No Drawings

3,6-DISUBSTITUTED XANTHYLIUM SALTS AND USE THEREOF IN TREATMENT OF TAUOPATHIES

CROSS-REFERENCE TO RELATED PATENT APPLICATIONS

This application is the U.S. National Phase of PCT/GB2009/002865, filed Dec. 10, 2009, which was published in English on Jun. 17, 2010, as WO 2010/067078, and which claims priority from U.S. Provisional Application No. 61/121,288, filed Dec. 10, 2008, all of which are incorporated herein by reference in entirety.

TECHNICAL FIELD

This invention pertains generally to processes, uses, methods and materials utilising particular xanthylium compounds. These compounds are useful as drugs, for example, in the treatment of tauopathies, such as Alzheimer's disease.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Conditions of dementia such as Alzheimer's disease (AD) are frequently characterised by a progressive accumulation of intracellular and/or extracellular deposits of proteinaceous structures such as β-amyloid plaques and neurofibrillary tangles (NFTs) in the brains of affected patients. The appearance of these lesions largely correlates with pathological neurofibrillary degeneration and brain atrophy, as well as with cognitive impairment (see, e.g., Mukaetova-Ladinska, E. B., et al., 2000, Am. J. Pathol., Vol. 157, No. 2, pp. 623-636).

In AD, both neuritic plaques and NFTs contain paired helical filaments (PHFs), of which a major constituent is the microtubule-associated protein tau (see, e.g., Wischik et al., 1988, PNAS USA, Vol. 85, pp. 4506-4510). Plaques also contain extracellular β-amyloid fibrils derived from the abnormal processing of amyloid precursor protein (APP) (see, e.g., Kang et al., 1987, Nature, Vol. 325, p. 733). An article by Wischik et al. (in 'Neurobiology of Alzheimer's Disease', 2nd Edition, 2000, Eds. Dawbarn, D. and Allen, S. J., The Molecular and Cellular Neurobiology Series, Bios Scientific Publishers, Oxford) discusses in detail the putative role of tau protein in the pathogenesis of neurodegenerative dementias. Loss of the normal form of tau, accumulation of pathological PHFs, and loss of synapses in the mid-frontal cortex all correlate with associated cognitive impairment. Furthermore, loss of synapses and loss of pyramidal cells both correlate with morphometric measures of tau-reactive neurofibrillary pathology, which parallels, at a molecular level, an almost total redistribution of the tau protein pool from a soluble to a polymerised form (i.e., PHFs) in Alzheimer's disease.

Tau exists in alternatively-spliced isoforms, which contain three or four copies of a repeat sequence corresponding to the microtubule-binding domain (see, e.g., Goedert, M., et al., 1989, EMBO J., Vol. 8, pp. 393-399; Goedert, M., et al., 1989, Neuron, Vol. 3, pp. 519-526). Tau in PHFs is proteolytically processed to a core domain (see, e.g., Wischik, C. M., et al., 1988, PNAS USA, Vol. 85, pp. 4884-4888; Wischik et al., 1988, PNAS USA, Vol. 85, pp. 4506-4510; Novak, M., et al., 1993, EMBO J., Vol. 12, pp. 365-370) which is composed of a phase-shifted version of the repeat domain; only three repeats are involved in the stable tau-tau interaction (see, e.g., Jakes, R., et al., 1991, EMBO J., Vol. 10, pp. 2725-2729). Once formed, PHF-like tau aggregates act as seeds for the further capture and provide a template for proteolytic processing of full-length tau protein (see, e.g., Wischik et al., 1996, PNAS USA, Vol. 93, pp. 11213-11218).

The phase shift which is observed in the repeat domain of tau incorporated into PHFs suggests that the repeat domain undergoes an induced conformational change during incorporation into the filament. During the onset of AD, it is envisaged that this conformational change could be initiated by the binding of tau to a pathological substrate, such as damaged or mutated membrane proteins (see, e.g., Wischik, C. M., et al., 1997, in "Microtubule-associated proteins: modifications in disease", Eds. Avila, J., Brandt, R. and Kosik, K. S. (Harwood Academic Publishers, Amsterdam) pp. 185-241).

In the course of their formation and accumulation, PHFs first assemble to form amorphous aggregates within the cytoplasm, probably from early tau oligomers which become truncated prior to, or in the course of, PHF assembly (see, e.g., Mena, R., et al., 1995, Acta Neuropathol., Vol. 89, pp. 50-56; Mena, R., et al., 1996, Acta Neuropathol., Vol. 91, pp. 633-641). These filaments then go on to form classical intracellular NFTs. In this state, the PHFs consist of a core of truncated tau and a fuzzy outer coat containing full-length tau (see, e.g., Wischik et al., 1996, PNAS USA, Vol. 93, pp. 11213-11218). The assembly process is exponential, consuming the cellular pool of normal functional tau and inducing new tau synthesis to make up the deficit (see, e.g., Lai, R. Y. K., et al., 1995, Neurobiology of Ageing, Vol. 16, No. 3, pp. 433-445). Eventually, functional impairment of the neurone progresses to the point of cell death, leaving behind an extracellular NFT. Cell death is highly correlated with the number of extracellular NFTs (see, e.g., Wischik et al., in 'Neurobiology of Alzheimer's Disease', 2nd Edition, 2001, Eds. Dawbarn, D. and Allen, S. J., The Molecular and Cellular Neurobiology Series, Bios Scientific Publishers, Oxford). As tangles are extruded into the extracellular space, there is progressive loss of the fuzzy outer coat of the neurone with corresponding loss of N-terminal tau immunoreactivity, but preservation of tau immunoreactivity associated with the PHF core (see, e.g., Bondareff, W. et al., 1994, J. Neuropath. Exper. Neurol., Vol. 53, No. 2, pp. 158-164).

Xanthylium compounds (also known as pyronine compounds) have previously been shown to act as fluorescent dyes. Xanthylium compounds previously disclosed include:

| Compound | Structure and Name | Citation |
|---|---|---|
| A | 2,3,6,7,12,13,16,17-Octahydro-1H,5H,11H,15H-diquinolizino[1,9-bc: 1′,9′-hi] xanthylium chloride | See e.g.: U.S. Pat. No. 3,932,415 |
| C | 8-(Trifluoromethyl-2,3,5,6,11,12,14,15-octahydro-1H,4H,10H,13H-diquinolizino[9,9a,1-bc; 9′,9a′1′-hi] xanthylium perchlorate | See e.g.: Haley et al. |
| X | 2,3,6,7,12,13,16,17-Octahydro-1H,5H,11H,15H-diquinolizino[1,9-bc: 1′,9′-hi] xanthylium perchlorate | See e.g.: Prostota et al. |
| E | 3,6-Bis-diethylamino xanthylium chloride | See e.g.: J. Biehringer *Journal Fur Praktische Chemie* |
| G | 3,6-Bis-diethylamino xanthylium iron tetrachloride | See e.g.: JP 2000 344684 Chamberlin et al. |
| LZ | 3,6-Bis(dimethylamino)thioxanthylium zinc trichloride | See e.g.: Nealey et al. |
| LP | 3,6-Bis(dimethylamino)thioxanthylium perchlorate | See e.g.: Müller et al. |

| Compound | Structure and Name | Citation |
|---|---|---|
| MC | 3,7-Bis(diethylamino)phenazinium chloride | See e.g.: Gloster et al. |
| MP | 3,7-Bis(dimethylamino)phenazinium perchlorate | See e.g.: Müller et al. |
| O | 3,7-Bis(dimethylamino)oxazinium perchlorate | See e.g.: Müller et al. |
| Y | 3,6-Bis-diethylamino xanthylium zinc trichloride | See e.g.: Albert |
| Z | 3,6-bis-methylamino xanthylium chloride | See e.g.: DE 65282 |
| AA | 9-(2-Carboxyethyl)-3,6-Bis-dimethylamino xanthylium chloride | See e.g.: JP 2000/344684 |

| Compound | Structure and Name | Citation |
|---|---|---|
| AL | 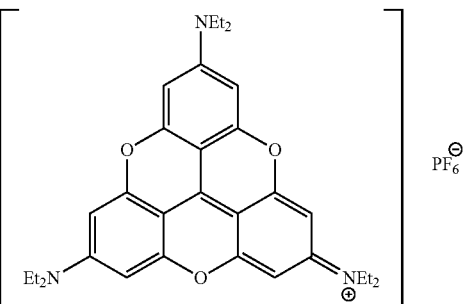<br>2,6,10-Tris-diethylamino-4,8,12-trioxatriangulenium hexafluorophosphate | See e.g.:<br>Laursen, et al |

JP 2000/344684 describes the use of xanthylium compounds, such as compound G and AA, as probes for diseases which accumulate β-amyloid protein.

WO 96/30766 describes the use of a xanthylium compound, DMAXC, as capable of inhibiting tau-tau protein interactions:

| Compound | Structure and Name |
|---|---|
| DMAXC | 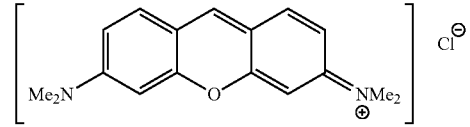<br>3,6-Bis-dimethylamino xanthylium chloride |

Diaminophenothiazines have previously been shown to inhibit tau protein aggregation and to disrupt the structure of PHFs, and reverse the proteolytic stability of the PHF core (see, e.g., WO 96/30766, F Hoffman-La Roche). Such compounds were disclosed for use in the treatment or prophylaxis of various diseases, including Alzheimer's disease. These included, amongst others:

| Compound | Structure and Name |
|---|---|
| MTC | 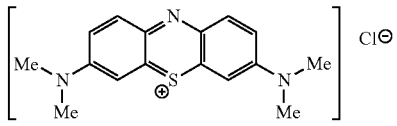<br>Methyl-thioninium chloride |
| DMMTC | 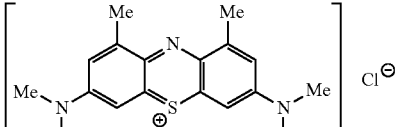<br>1,9-Dimethyl-methyl-thioninium chloride |

It will be understood that the term 'xanthylium compounds', as used herein, refers generally to compounds having a xanthylium core structure and compounds having related core structures including, but not limited to thioxanthylium, phenazinium, oxazinium, and thioninium.

Notwithstanding the above disclosures, it will be appreciated that the provision of one or more xanthylium compounds, not previously specifically identified as being effective tau protein aggregation inhibitors, would provide a contribution to the art.

DESCRIPTION OF THE INVENTION

The present inventors have now identified certain xanthylium compounds as being effective tau protein aggregation inhibitors and in preferred forms having certain other desirable properties, for example by comparison with the compounds of the prior art discussed above.

As discussed above, tau proteins are characterised as being one among a larger number of protein families which co-purify with microtubules during repeated cycles of assembly and disassembly (Shelanski et al. *Proc. Natl. Acad. Sci. USA* 1973, 70, 765-768), and are known as microtubule-associated-proteins (MAPs). Members of the tau family share the common features of having a characteristic N-terminal segment, sequences of approximately 50 amino acids inserted in the N-terminal segment, which are developmentally regulated in the brain, a characteristic tandem repeat region consisting of 3 or 4 tandem repeats of 31-32 amino acids, and a C-terminal tail.

One or more of the xanthylium compounds are known in the art—for example compound A (2,3,6,7,12,13,16,17-Octahydro-1H,5H,11H,15H-diquinolizino[1,9-bc:1',9'-hi]xanthylium chloride) is described in U.S. Pat. No. 3,932,415. However it is believed that none of these have previously been disclosed in the prior art as tau protein aggregation inhibitors.

The invention therefore relates to methods, uses, compositions and other materials employing these compounds as tau protein aggregation inhibitors and as therapeutics or prophylactics of diseases associated with tau protein aggregation ("tauopathies"). The invention further provides processes for making these compounds.

These and other aspects of the invention are discussed in more detail hereinafter.

Compounds

In one aspect the present invention provides compounds of formula (I), and particularly their use in medicine:

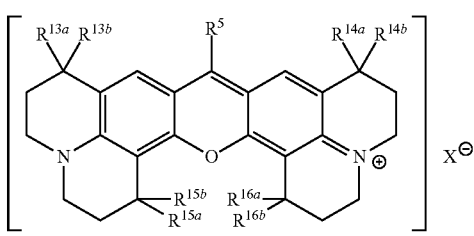

(I)

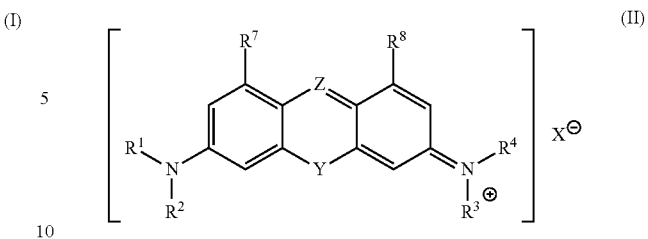

(II)

wherein:

X⁻ is an anion;

—$R^5$ is independently —H, or saturated $C_{1-6}$alkyl, which is unsubstituted or substituted with one or more substituents —$R^{5A}$, or phenyl, which is unsubstituted or substituted with one or more substituents —$R^{6A}$;

each —$R^{5A}$ is independently selected from —F, —Cl, —Br, —I, —OH, —$OR^6$, —SH, —$SR^6$, —CN, —$NO_2$, —$NH_2$, —$NHR^6$, —$NR^6_2$, —NHC(=O)$R^6$, —$NR^6$C(=O)$R^6$, —C(=O)$OR^6$, —OC(=O)$R^6$, —C(=O)$NH_2$, —C(=O)$NHR^6$, —C(=O)$NR^6_2$, —C(=O)$R^6$, —C(=O)OH, —S(=O)$R^6$, —S(=O)$_2R^6$, and —S(=O)$_2$OH; and each —$R^6$ is independently saturated aliphatic $C_{1-4}$alkyl, phenyl, or benzyl;

—$R^{13a}$, —$R^{13b}$, —$R^{14a}$, —$R^{14b}$, —$R^{15a}$, —$R^{15b}$, —$R^{16a}$, and —$R^{16b}$ are each independently selected from H and saturated aliphatic $C_{1-4}$ alkyl.

In one embodiment —$R^{13a}$, —$R^{13b}$, —$R^{14a}$, —$R^{14b}$, —$R^{15a}$, —$R^{15b}$, —$R^{16a}$, and —$R^{16b}$ are all H, providing a compound of formula (Ic).

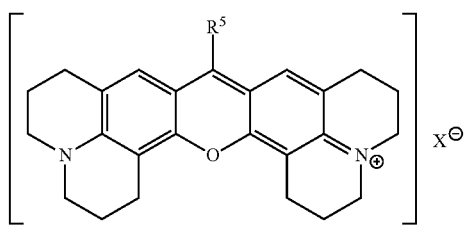

(Ic)

wherein X and $R^5$ are as defined above.

In one embodiment —$R^5$ is independently —H, or saturated $C_{1-6}$alkyl, which is unsubstituted or substituted with one or more substituents —$R^{5A}$.

In one embodiment, the compound of the invention is a compound of formula (I) or (I') with the proviso that the compound is not:

2,3,6,7,12,13,16,17-octahydro-1H,5H,11H,15H-diquinolizino[1,9-bc:1',9'-hi]xanthylium chloride ("compound A");

8-(trifluoromethyl)-2,3,5,6,11,12,14,15-octahydro-1H,4H,10H,13H-diquinolizino[9,9a,1-bc;9',9a'1'-hi]xanthylium perchlorate ("compound C"); or 2,3,6,7,12,13,16,17-octahydro-1H,5H,11H,15H-diquinolizino[1,9-bc:1',9'-hi]xanthylium perchlorate ("compound X").

In a further aspect of the present invention there are provided compounds of formula (II) and particularly their use in medicine:

wherein:

X⁻ is a counter ion;

Y is O, and Z is N or C—$R^5$; or

Y is S, and Z is C—$R^5$;

—$R^1$ and —$R^2$, are each independently saturated $C_{1-6}$alkyl, or $R^1$ and $R^2$, together with the nitrogen atom to which they are bound, form a saturated $C_{3-7}$ heterocycle;

—$R^3$ and —$R^4$ are each independently saturated $C_{1-6}$alkyl, or $R^3$ and $R^4$, together with the nitrogen atom to which they are bound, form a saturated $C_{3-7}$ heterocycle;

—$R^5$ is independently —H, saturated $C_{1-6}$alkyl, which is unsubstituted or substituted with one or more substituents —$R^{5A}$, or phenyl, which is unsubstituted or substituted with one or more substituents —$R^{5A}$;

each —$R^{5A}$ is independently selected from —F, —Cl, —Br, —I, —OH, —$OR^6$, —SH, —$SR^6$, —CN, —$NO_2$, —$NH_2$, —$NHR^6$, —$NR^6_2$, —NHC(=O)$R^6$, —$NR^6$C(=O)$R^6$, —C(=O)$OR^6$, —OC(=O)$R^6$, —C(=O)$NH_2$, —C(=O)$NHR^6$, —C(=O)$NR^6_2$, —C(=O)$R^6$, —C(=O)OH, —S(=O)$R^6$, —S(=O)$_2R^6$, and —S(=O)$_2$OH;

each —$R^6$ is independently saturated aliphatic $C_{1-4}$alkyl, phenyl, or benzyl; and —$R^7$ and —$R^8$ are each independently selected from: —H, saturated $C_{1-4}$alkyl, $C_{2-4}$alkenyl, and halogenated $C_{1-4}$alkyl; and additionally, when Z is C—$R^5$ and $R^5$ is phenyl, —$R^7$ and —$R^8$ may each independently be a bridging group, W, which is bonded to said $R^5$; and W is O, $NR^{17}$, S, or $C(R^{17})_2$ wherein each $R^{17}$ is independently selected from H, saturated aliphatic $C_{1-4}$ alkyl, and $R^{5A}$.

In one embodiment, —$R^1$, —$R^2$, —$R^3$ and —$R^4$ are each independently saturated aliphatic $C_{1-6}$alkyl.

In one embodiment, —$R^7$ and —$R^8$ are each independently selected from: —H, saturated $C_{1-4}$alkyl, $C_{2-4}$alkenyl, and halogenated $C_{1-4}$alkyl.

In one embodiment, —$R^5$ is independently —H, saturated $C_{1-6}$alkyl, which is unsubstituted or substituted with one or more substituents —$R^{5A}$.

In one embodiment, at least one of —$R^1$, —$R^2$, —$R^3$ and —$R^4$ is independently unsubstituted saturated aliphatic $C_{2-6}$alkyl.

In one embodiment, the compound of the invention is a compound of formula (II) with the proviso that the compound is not:

3,6-bis(dimethylamino)thioxanthylium zinc trichloride ("compound LZ");

3,6-bis(dimethylamino)thioxanthylium perchlorate ("compound LP");

3,7-bis(dimethylamino)phenazinium chloride ("compound MC");

3,7-Bis(dimethylamino)phenazinium perchlorate ("compound MP"); or 3,7-bis(dimethylamino)oxazinium chloride ("compound O").

In another embodiment, the compound of the invention is a compound of formula (II) with the proviso that the compound is not:

3,6-bis-diethylamino xanthylium chloride ("compound E");

3,6-bis-diethylamino xanthylium iron tetrachloride ("compound G"); or 3,6-bis-diethylamino xanthylium zinc trichloride ("compound Y").

In another embodiment, the compound of the invention is a compound of formula (II) with the proviso that the compound is not 9-(2-carboxyethyl)-3,6-Bis-dimethylamino xanthylium chloride ("compound AA").

In another embodiment, the compound of the invention is a compound of formula (II) with the proviso that the compound is not 3,6-bis-dimethylamino xanthylium chloride ("DMAXC").

In a preferred embodiment of the invention there are provided compounds of formula (IIa) and particularly their use in medicine:

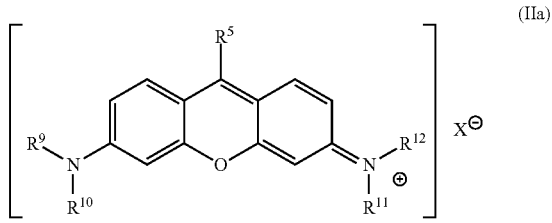

(IIa)

wherein:

X$^-$ is a counter ion;

—R$^9$, and —R$^{10}$ are each independently saturated C$_{1-6}$alkyl; or —R$^9$ and —R$^{10}$, together with the nitrogen atom to which they are bound, form a saturated C$_{3-7}$ heterocycle;

—R$^{11}$ and —R$^{12}$ are each independently saturated C$_{1-6}$alkyl, or —R$^{11}$ and —R$^{12}$, together with the nitrogen atom to which they are bound, form a saturated C$_{3-7}$ heterocycle; and —R$^5$ is defined according to the compounds of formula (II).

In one embodiment, R$^9$, —R$^{10}$, —R$^{11}$ and —R$^{12}$ are each independently saturated C$_{2-6}$alkyl.

In one embodiment, the compound of the invention is a compound of formula (IIa) with the proviso that the compound is not:

3,6-bis-diethylamino xanthylium chloride ("compound E");

3,6-bis-diethylamino xanthylium iron tetrachloride ("compound G");

3,6-bis-diethylamino xanthylium zinc trichloride ("compound Y");

In one embodiment, the compound of the invention is a compound of formula (IIa) with the proviso that the compound is not 3,6-bis-dimethylamino xanthylium chloride (DMAXC).

In a preferred embodiment of the invention there are provided compounds of formula (IIb) and particularly their use in medicine:

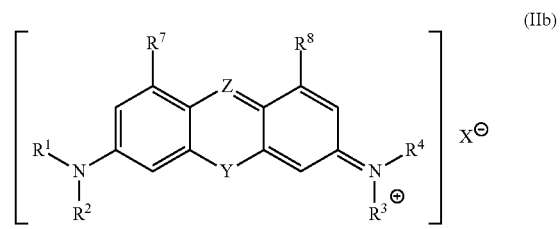

(IIb)

wherein:

X$^-$ is a counter ion;

Y is O or NH, and Z is N; or

Y is S, and Z is C—R$^5$;

—R$^1$, —R$^2$, —R$^3$, —R$^4$, —R$^5$, —R$^7$ and —R$^8$ are defined according to the compound of formula (II).

In one embodiment, the compound of the invention is a compound of formula (IIb) with the proviso that the compound is not:

3,6-bis(dimethylamino)thioxanthylium zinc trichloride ("compound L");

3,7-bis(dimethylamino)phenazinium chloride ("compound M"); or 3,7-bis(dimethylamino)oxazinium chloride ("compound O").

In an alternative embodiment of the invention, there are provided compounds of formula (IIc) and particularly their use in medicine:

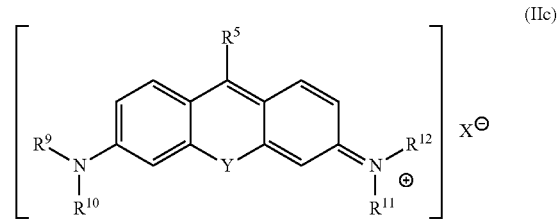

(IIc)

wherein:

X$^-$ is a counter ion;

Y is O or S;

—R$^9$ and —R$^{10}$ are each independently saturated C$_{1-6}$alkyl; - or R$^9$ and R$^{10}$, together with the nitrogen atom to which they are bound, form a saturated C$_{3-7}$ heterocycle;

—R$^{11}$ and —R$^{12}$ are each independently saturated C$_{1-6}$alkyl, or R$^{11}$ and R$^{12}$, together with the nitrogen atom to which they are bound, form a saturated C$_{3-7}$ heterocycle; and —R$^5$ is defined according to the compounds of formula (II).

In one embodiment, R$^9$, —R$^{10}$, —R$^{11}$ and —R$^{12}$ are each independently saturated C$_{2-6}$alkyl.

In one embodiment, the compound of the invention is a compound of formula (IIc) with the proviso that the compound is not:

3,6-bis-diethylamino xanthylium chloride ("compound E");

3,6-bis-diethylamine xanthylium iron tetrachloride ("compound G"); or 3,6-bis-diethylamino xanthylium zinc trichloride ("compound Y")

In one embodiment, the compound of the invention is a compound of formula (IIc) with the proviso that the compound is not 3,6-bis-dimethylamino xanthylium chloride (DMAXC).

In an alternative embodiment, there are provided compounds wherein Z is C—$R^5$, $R^5$ is phenyl, and —$R^7$ and —$R^8$ are each independently a bridging group, W, which is bonded to said $R^5$, and their use in medicine.

These compounds can also be described as compounds of formula (VI):

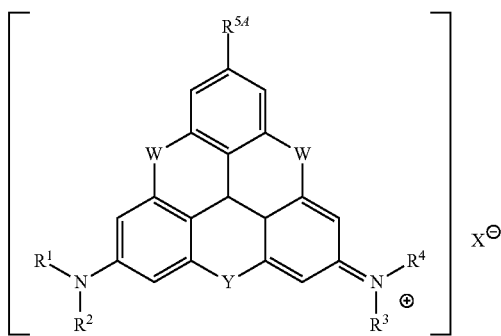

(VI)

wherein $X^-$, Y, W, —$R^1$, —$R^2$, —$R^3$, —$R^4$ and —$R^{5A}$ are as defined according to the compounds of formula (II).

In one embodiment, at least one of —$R^1$, —$R^2$, —$R^3$ and —$R^4$ is independently unsubstituted saturated aliphatic $C_{2-6}$alkyl.

In one embodiment, the compound of the invention is a compound of formula (VI) with the proviso that the compound is not 2,6,10-tris-diethylamino-4,8,12-trioxatrianguleum hexafluorophosphate ('compound AL').

In a preferred embodiment of the invention, there are provided compounds of formula (VIa) and particularly their use in medicine:

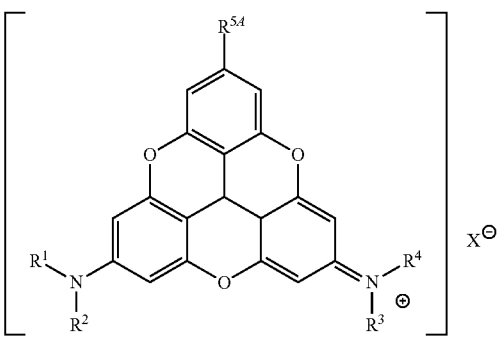

(VIa)

wherein $X^-$, —$R^1$, —$R^2$, —$R^3$, —$R^4$, —$R^5$ and —$R^{5A}$ are as defined according to the compounds of formula (VI).

In one embodiment, the compound of the invention is a compound of formula (VIa) with the proviso that the compound is not 2,6,10-tris-diethylamino-4,8,12-trioxatrianguleum hexafluorophosphate ('compound AL').

In a further aspect of the present invention there are provided compounds of formula (III), and particularly their use in medicine:

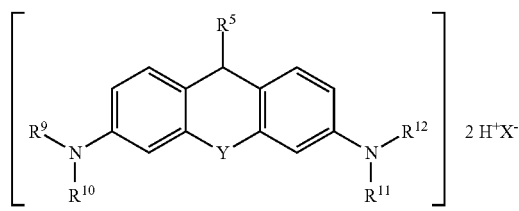

(III)

wherein:
$X^-$ is a counter ion;
Y is O or S;
—$R^9$ and —$R^{10}$ are each independently saturated $C_{1-6}$alkyl;
or $R^9$ and $R^{10}$, together with the nitrogen atom to which they are bound, form a saturated $C_{3-7}$ heterocycle;
—$R^{11}$ and —$R^{12}$ are each independently saturated $C_{1-6}$alkyl,
or $R^{11}$ and $R^{12}$, together with the nitrogen atom to which they are bound, form a saturated $C_{3-7}$ heterocycle; and
—$R^5$ is defined according to the compounds of formula (II).

In one embodiment, $R^9$, —$R^{10}$, —$R^{11}$ and —$R^{12}$ are each independently saturated $C_{2-6}$alkyl.

In one embodiment, the compound of the invention is a compound of formula (III) with the proviso that the compound is not 3,6-bis-diethylamino xanthene dihydrochloride ("compound H").

The compounds (I), (Ic), (II), (IIa), (IIb), (IIc), (III), (VI), and (VIa) are described herein as "xanthylium compounds" or "compounds of the invention" or (unless context demands otherwise) "active compounds".

The preferred counter ions and substituents for the compounds (I), (Ic), (II), (IIa), (IIb), (IIc), (III), (VI) and (VIa) are set out below. They are combinable in any combination, where appropriate. Each and every compatible combination of the embodiments described above, and below, is explicitly disclosed herein, as if each and every combination was individually and explicitly recited.

Preferences for $X^-$ $X^-$ is a counter ion. $X^-$ is one or more anionic counter ions to achieve electrical neutrality.

In one embodiment, $X^-$ is one anionic counter ion.

In one embodiment, each $X^-$ is a pharmaceutically acceptable anion.

In one embodiment, each $X^-$ may be selected from the group consisting of: $NO_3^-$, $ClO_4^-$, $F^-$, $Cl^-$, $Br^-$, $I^-$, $ZnCl_3^-$, $FeCl_4^-$, and $PF_6^-$.

In one embodiment, each $X^-$ may be selected from the group consisting of: $NO_3$, $ClO_4^-$, $Cl^-$, $Br^-$, $I^-$, $FeCl_4^-$, and $PF_6^-$.

In one embodiment, each $X^-$ may be selected from $NO_3^-$, $Cl^-$, and $ClO_4^-$.

In one embodiment, each $X^-$ may be selected from $NO_3^-$, $Cl^-$, Br and $FeCl_4$.

In one embodiment, each $X^-$ may be selected from $I^-$, Br, $NO_3^-$ and $Cl^-$.

In one embodiment, each $X^-$ may be selected from $I^-$, $NO_3^-$ and $Cl^-$.

$X^-$ may be $ZnCl_3^-$.
$X^-$ may be $NO_3^-$.
$X^-$ may be $Cl^-$.
$X^-$ may be $ClO_4^-$.
$X^-$ may be $Br^-$.

$X^-$ may be $I^-$.

$X^-$ may be $FeCl_4^-$.

$X^-$ may be $PF_6^-$.

In one embodiment, $X^-$ is a mixed anionic counter ion. In one embodiment, the compound is in the form of a mixed salt, for example, a $HNO_3$ mixed salt. In one embodiment the compound is in the form of a $NO_3^-$ and $HNO_3$ mixed salt.

Preferences for $—R^{13a}$, $—R^{13b}$, $—R^{14a}$, $—R^{14b}$, $—R^{15a}$, $—R^{16a}$, and $—R^{16b}$ $—R^{13a}$, $—R^{13b}$, $—R^{14a}$, $—R^{14b}$, $—R^{15a}$, $—R^{15b}$, $—R^{16a}$, and $—R^{16b}$ are each independently selected from H and saturated aliphatic $C_{1-4}$ alkyl.

In one embodiment, $—R^{13a}$, $—R^{13b}$, $—R^{14a}$, $—R^{14b}$, $—R^{15a}$, $—R^{15b}$, $—R^{16a}$, and $—R^{16b}$ are each independently H.

In one embodiment, $—R^{13a}$, $—R^{14a}$, $—R^{14b}$, $—R^{15a}$, $—R^{15b}$, $—R^{16a}$, and $—R^{16b}$ are all H.

In one embodiment, $—R^{13a}$, $—R^{13b}$, $—R^{14a}$, $—R^{15a}$, $—R^{15b}$, $—R^{16a}$, and $—R^{16b}$ are each independently saturated aliphatic $C_{1-4}$ alkyl.

In one embodiment, $—R^{13a}$, $—R^{14a}$, $—R^{14b}$, $—R^{15a}$, $—R^{15b}$, $—R^{16a}$, and $—R^{16b}$ are each independently selected from methyl, ethyl, n-propyl, iso-propyl, n-butyl, iso-butyl, and t-butyl.

In one embodiment, $—R^{13a}$, $—R^{13b}$, $—R^{14a}$, $—R^{14b}$, $—R^{15a}$, $—R^{15b}$, $—R^{16a}$, and $—R^{16b}$ are each independently methyl or ethyl.

In one embodiment, $—R^{13a}$, $—R^{13b}$, $—R^{14a}$, $—R^{14b}$, $—R^{15a}$, $—R^{15b}$, $—R^{16a}$, and $R^{16b}$ are each independently methyl.

In one embodiment, $—R^{13a}$, $—R^{13b}$, $—R^{14a}$, $—R^{14b}$, $—R^{15a}$, $—R^{15b}$, $—R^{16a}$, and $—R^{16b}$ are all methyl.

Preferences for Y, Z, and W

For the compounds of formula (II), Y is independently O, NH or S.

In one embodiment, Y is O.

In one embodiment, Y is NH.

In one embodiment, Y is S.

In one embodiment, Y is O or NH, and Z is N.

In one embodiment, Y is O or S, and Z is C—$R^5$.

In one embodiment, Y is O, and Z is N or C—$R^5$.

In one embodiment, Y is O, and Z is N.

In one embodiment, Y is O, and Z is C—$R^5$.

In one embodiment, Y is NH, and Z is N.

In one embodiment, Y is S, and Z is C—$R^5$.

For the compounds of formula (IIb), Y is independently O, NH or S.

In one embodiment, Y is O, and Z is N.

In one embodiment, Y is NH, and Z is N.

In one embodiment, Y is S, and Z is C—$R^5$.

For the compounds of formula (IIc), Y is independently O or S.

In one embodiment, Y is O.

In one embodiment, Y is S.

For the compounds of formula (III), Y is independently O or S.

In one embodiment, Y is O.

In one embodiment, Y is S.

For the compounds of formula (IV), Y is independently O, NH or S.

In one embodiment, Y is O.

In one embodiment, Y is NH.

In one embodiment, Y is S.

Each W is independently O, $NR^{17}$, $CR^{17}_2$, or S.

In one embodiment, each W is independently O, $NR^{17}$ or S.

In one embodiment, each W is independently O, NH or S.

In one embodiment, each W is independently O or S.

In one embodiment, each W is independently O.

In one embodiment, each W is independently $CR^{17}_2$.

In one embodiment, each W is independently $CH_2$.

Preferences for $—R^{17}$

Each $R^{17}$ is independently H, saturated aliphatic $C_{1-4}$ alkyl, or is as defined for $R^{5A}$.

In one embodiment, each $R^{17}$ is H.

In one embodiment, each $R^{17}$ is independently H or saturated aliphatic $C_{1-4}$ alkyl.

In one embodiment, each $R^{17}$ is independently saturated aliphatic $C_{1-4}$ alkyl.

In one embodiment, each $R^{17}$ is independently selected from methyl, ethyl, n-propyl, iso-propyl, n-butyl, iso-butyl, and t-butyl.

In one embodiment, each $R^{17}$ is independently selected from H or methyl.

In one embodiment W is $NR^{17}$ and $R^{17}$ is H or saturated aliphatic $C_{1-4}$ alkyl.

In one embodiment W is $NR^{17}$ and $R^{17}$ is H.

In one embodiment W is $NR^{17}$ and $R^{17}$ is saturated aliphatic $C_{1-4}$ alkyl.

In one embodiment W is $C(R^{17})_2$ and each $R^{17}$ is H or saturated aliphatic $C_{1-4}$ alkyl.

In one embodiment W is $C(R^{17})_2$ and each $R^{17}$ is H.

In one embodiment W is $C(R^{17})_2$ wherein one $R^{17}$ is H and the other is saturated aliphatic $C_{1-4}$ alkyl.

In one embodiment W is $C(R^{17})_2$ and each $R^{17}$ is saturated aliphatic $C_{1-4}$ alkyl.

Preferences for $—R^1$, $—R^2$, $—R^3$ and $—R^4$

In one embodiment, $—R^1$ and $—R^2$, are each independently saturated $C_{1-6}$alkyl, or $R^1$ and $R^2$, together with the nitrogen atom to which they are bound, form a saturated $C_{3-7}$ heterocycle; and $—R^3$ and $—R^4$ are each independently saturated $C_{1-6}$alkyl, or $R^3$ and $R^4$, together with the nitrogen atom to which they are bound, form a saturated $C_{3-7}$ heterocycle.

In one embodiment, $—R^1$, $—R^2$, $—R^3$ and $—R^4$ are each independently saturated aliphatic $C_{1-6}$alkyl.

In one embodiment, at least one of $—R^1$, $—R^2$, $—R^3$ and $—R^4$ is independently saturated aliphatic $C_{2-6}$alkyl.

In one embodiment, $—R^1$, $—R^2$, $—R^3$ and $—R^4$ are each independently saturated aliphatic $C_{2-6}$alkyl.

In one embodiment, $—R^1$, $—R^2$, $—R^3$ and $—R^4$ are each independently saturated $C_{3-6}$cycloalkyl.

In one embodiment, at least one of $—R^1$, $—R^2$, $—R^3$ and $—R^4$ is independently saturated $C_{3-6}$cycloalkyl.

In one embodiment, $—R^2$, $—R^3$ and $—R^4$ are defined according to $—R^9$, $—R^{10}$, $R^{11}$ and $—R^{12}$ respectively.

In one embodiment, $—R^1$ and $—R^2$ are the same.

In one embodiment, $—R^1$ and $—R^2$ are each -Me.

In one embodiment, $—R^1$ and $—R^2$ are each -Et.

In one embodiment, $—R^1$ and $—R^3$ are the same.

In one embodiment, $—R^3$ and $—R^3$ are the same.

In one embodiment, $—R^3$ and $—R^4$ are each -Me.

In one embodiment, $—R^3$ and $—R^4$ are each -Et.

In one embodiment, $—R^2$ and $—R^4$ are the same.

In one embodiment, one of $—R^1$ and $—R^2$ is -Me.

In one embodiment, one of $—R^1$ and $—R^2$ is -Et.

In one embodiment, one of $—R^3$ and $—R^3$ is -Me.

In one embodiment, one of $—R^3$ and $—R^3$ is -Et.

In one embodiment, $—R^1$, $—R^2$, $—R^3$ and $—R^4$ are each -Me.

In one embodiment, $—R^1$, $—R^2$, $—R^3$ and $—R^4$ are each -Et.

In one embodiment, $—R^1$ and $—R^2$, together with the nitrogen atom to which they are bound, form a saturated $C_{3-7}$ heterocycle; and —$R^3$ and —$R^4$, together with the nitrogen atom to which they are bound, independently form a saturated $C_{3-7}$ heterocycle.

In one embodiment the saturated $C_{3-7}$ heterocycle formed by $R^1$ and $R^2$ and the saturated $C_{3-7}$ heterocycle formed by $R^3$ and $R^4$ are independently selected from: aziridine, azetidine, pyrrolidine, imidazolidine, pyrazolidine, oxazolidine, isoxazolidine, piperidine, piperazine, morpholine, azepine, oxazepine, and diazepine.

In one embodiment the saturated $C_{3-7}$ heterocycle formed by $R^1$ and $R^2$ and the saturated $C_{3-7}$ heterocycle formed by $R^3$ and $R^4$ are independently selected from: morpholine, piperidine, and pyrrolidine.

In one embodiment the saturated $C_{3-7}$ heterocycle is morpholine.

In one embodiment the saturated $C_{3-7}$ heterocycle is piperidine.

In one embodiment the saturated $C_{3-7}$ heterocycle is pyrrolidine.

In one embodiment the saturated $C_{3-7}$ heterocycle formed by $R^1$ and $R^2$ and the saturated $C_{3-7}$ heterocycle formed by $R^3$ and $R^4$ are the same.

Preferences for —$R^5$ and —$R^{5A}$

In one embodiment, —$R^5$ is independently —H, saturated $C_{1-6}$alkyl, which is unsubstituted or substituted with one or more substituents —$R^{5A}$, or phenyl, which is unsubstituted or substituted with one or more substituents —$R^{5A}$. —$R^{5A}$ is independently selected from —F, —Cl, —Br, —I, —OH, —SH, —$SR^6$, —CN, —$NO_2$, —$NH_2$, —$NHR^6$, —$NR^6_2$, —NHC(=O)$R^6$, —$NR^6$C(=O)$R^6$, —C(=O)$OR^6$, —OC(=O)$R^6$, —C(=O)$NH_2$, —C(=O)$NHR^6$, —C(=O)$NR^6_2$, —C(=O)$R^6$, —C(=O)OH, —S(=O)$R^6$, —S(=O)$_2R^6$, and —S(=O)$_2$OH.

In one embodiment, —$R^5$ is —H.

In one embodiment, —$R^5$ is saturated aliphatic $C_{1-6}$alkyl, which is unsubstituted or substituted with one or more substituents —$R^{5A}$.

In one embodiment, —$R^5$ is saturated $C_{3-6}$cycloalkyl or saturated aliphatic $C_{1-4}$alkyl, both of which are unsubstituted or substituted with one or more substituents —$R^{5A}$.

In one embodiment, —$R^5$ is saturated $C_{3-6}$cycloalkyl, which is unsubstituted or substituted with one or more substituents —$R^{5A}$.

In one embodiment, —$R^5$ is unsubstituted saturated aliphatic $C_{1-4}$alkyl.

In one embodiment, —$R^5$ is saturated aliphatic $C_{1-4}$alkyl, which is unsubstituted or substituted with one or more substituents —$R^{5A}$.

In one embodiment, —$R^5$ is $C_{1-4}$alkyl substituted with one or more substituents —$R^{5A}$.

In one embodiment, —$R^5$ is saturated aliphatic $C_{1-4}$alkyl substituted with one or more substituents In one embodiment, —$R^5$ is -Me or -Et, which is unsubstituted or substituted with one or more substituents —$R^{5A}$.

In one embodiment, —$R^5$ is —$CF_3$ or -Et.

In one embodiment, —$R^5$ is —$CF_3$.

In one embodiment, —$R^5$ is -Et.

In one embodiment, —$R^5$ is independently phenyl, which is unsubstituted or substituted with one or more substituents —$R^{5A}$.

In one embodiment, —$R^5$ is independently phenyl, which is substituted with one or more substituents —$R^{5A}$.

When $R^5$ is phenyl, it may be substituted with one or more substituents —$R^{5A}$ in a position ortho, meta or para to the tricyclic core.

In one embodiment, a substituent —$R^{5A}$ is in the ortho position.

In one embodiment, a substituent —$R^{5A}$ is in the meta position.

In one embodiment, a substituent —$R^{5A}$ is in the para position.

In one embodiment, each —$R^{5A}$ is independently selected from —F, —Cl, —Br, —I, —OH, —$OR^6$, —$SR^6$, —$NO_2$, —$NH_2$, —$NHR^6$, —$NR^6_2$, —NHC(=O)$R^6$, —$NR^6$C(=O)$R^6$, —C(=O)$OR^6$, —OC(=O)$R^6$, —C(=O)$NH_2$, —C(=O)$NHR^6$, —C(=O)$NR^6_2$, —C(=O)$R^6$, and —C(=O)OH.

In one embodiment, each —$R^{5A}$ is independently selected from —F, —Cl, —Br, —I, —OH, —$OR^6$, —$SR^6$, —$NO_2$, —$NH_2$, —$NHR^6$, —$NR^6_2$, —NHC(=O)$R^6$, —$NR^6$C(=O)$R^6$, —C(=O)$OR^6$, —OC(=O)$R^6$, —C(=O)$NH_2$, —C(=O)$NHR^6$, and —C(=O)$NR^6_2$, and —C(=O)$R^6$.

In one embodiment, each —$R^{5A}$ is independently selected from —F, —Cl, —Br, —I, —OH, —$OR^6$, —$SR^6$, —$NO_2$, —$NH_2$, —$NHR^6$, and —$NR^6_2$, In one embodiment, each —$R^{5A}$ is independently selected from —F, —Cl, —Br, —I, or —OH.

In one embodiment, each —$R^{5A}$ is independently selected from —F, —Cl, —Br, or —I.

In one embodiment, each $R^{5A}$ is independently selected from —$NH_2$, —$NHR^6$, —$NR^6_2$ and —$NO_2$.

In one embodiment, each $R^{5A}$ is independently selected from —$NR^6_2$ and —$NO_2$.

In one embodiment, —$R^5$ is substituted with one substituent —$R^{5A}$.

In one embodiment, —$R^5$ is substituted with two substituents —$R^{5A}$. The substituents may be the same or different.

In one embodiment, —$R^5$ is substituted with three substituents —$R^{5A}$. The substituents may be the same or different.

Preferences for —$R^6$

Each —$R^6$ is independently saturated aliphatic $C_{1-4}$alkyl, phenyl, or benzyl.

In one embodiment, —$R^6$ is saturated aliphatic $C_{1-4}$alkyl.

In one embodiment, —$R^6$ is phenyl.

In one embodiment, —$R^6$ is benzyl.

Preferences for —$R^7$ and —$R^8$

—$R^7$ and —$R^8$ are each independently selected from: —H, saturated $C_{1-4}$alkyl, $C_{2-4}$alkenyl, and halogenated $C_{1-4}$alkyl; and additionally, when Z is C—$R^5$ and $R^5$ is phenyl, —$R^7$ and —$R^8$ may each independently be a bridging group, W, which is bonded to said $R^5$.

In one embodiment —$R^7$ and —$R^8$ are each independently selected from: —H; saturated $C_{1-4}$alkyl; $C_{2-4}$alkenyl; and halogenated $C_{1-4}$alkyl.

In one embodiment, —$R^7$ and —$R^8$ are each independently —H.

In one embodiment, the $C_{1-4}$ alkyl groups are selected from: linear $C_{1-4}$alkyl groups, such as -Me, -Et, -nPr, -iPr, and -nBu; branched $C_{3-4}$alkyl groups, such as -iPr, -iBu, -sBu, and -tBu; and cyclic $C_{3-4}$alkyl groups, such as -cPr and -cBu.

In one embodiment, the $C_{2-4}$alkenyl groups are selected from linear $C_{1-4}$alkenyl groups, such as —CH=$CH_2$ (vinyl) and —$CH_2$—CH=$CH_2$ (allyl).

In one embodiment, the halogenated $C_{1-4}$alkyl groups are selected from: —$CF_3$, —$CH_2CF_3$, and —$CF_2CF_3$.

in one embodiment, each of —$R^7$ and —$R^8$ independently —H, or saturated aliphatic $C_{1-4}$alkyl.

In one embodiment, each of —$R^7$ and —$R^8$ is independently $C_{1-4}$alkyl.

In one embodiment, each of —$R^7$ and —$R^8$ is independently —H, -Me, -Et, or —$CF_3$.

In one embodiment, each of —$R^7$ and —$R^8$ is independently —H, -Me, or -Et.

In one embodiment, each of —R⁷ and —R⁸ is independently —H.

In one embodiment, each of —R⁷ and —R⁸ is independently -Me.

In one embodiment, each of —R⁷ and —R⁸ is independently -Et.

In one embodiment, —R⁷ and —R⁸ are the same.

In one embodiment, —R⁷ and —R⁸ are different.

In one embodiment, when Z is C—R⁵ and R⁵ is phenyl, —R⁷ and —R⁸ may each independently be a bridging group, W, which is bonded to said R⁵.

In one embodiment, —R⁷ and —R⁸ are each a bridging group, W, which is bonded to said phenyl group R⁵.

In one embodiment, —R⁷ and —R⁸ are each a bridging group, W, which is bonded to said phenyl group R⁵ at an ortho position, relative to the xanthylium core, to produce a six-membered fused ring.

In one embodiment, both —R⁷ and —R⁸ are bridging groups, W, and are each bonded to said phenyl group R⁵ at respective ortho positions, to produce six-membered fused rings as shown in formula (VI).

Preferences for —R⁹, —R¹⁰, —R¹¹ and —R¹²

—R⁹, —R¹⁰, —R¹¹ and —R¹² are each independently saturated $C_{2-6}$alkyl.

In one embodiment, —R⁹, —R¹⁰, —R¹¹ and —R¹² are each independently saturated $C_{2-6}$alkyl.

In one embodiment, the $C_{2-6}$alkyl groups are selected from: linear $C_{2-6}$alkyl groups, such as -Et, -nPr, -iPr, and -nBu; branched $C_{3-4}$alkyl groups, such as -iPr, -iBu, -sBu, and -tBu; and cyclic $C_{3-4}$alkyl groups, such as -cPr and -cBu.

In one embodiment, each —R⁹, —R¹⁰, —R¹¹ and —R¹² is independently saturated $C_{3-6}$cycloalkyl or unsubstituted saturated aliphatic $C_{2-6}$alkyl.

In one embodiment, each —R⁹, —R¹⁰, —R¹¹ and —R¹² is independently saturated $C_{3-6}$cycloalkyl.

In one embodiment, each —R⁹, —R¹⁰, —R¹¹ and —R¹² is independently saturated aliphatic $C_{2-6}$alkyl.

In one embodiment, each —R⁹, —R¹⁰, —R¹¹ and —R¹² is independently saturated aliphatic $C_{2-4}$alkyl.

In one embodiment each —R⁹, —R¹⁰, —R¹¹ and —R¹² is independently selected from -Et; -n-Pr, -iso-Pr, -n-Bu, -sec-Bu, -iso-Bu, and -tert-Bu.

In one embodiment, one of —R⁹ and —R¹⁰ is -Et.

In one embodiment, one of —R¹¹ and —R¹² is -Et.

In one embodiment, —R⁹ and —R¹⁰ are the same.

In one embodiment, —R⁹ and —R¹⁰ are each -Et.

In one embodiment, —R¹¹ and —R¹² are the same.

In one embodiment, —R¹¹ and —R¹² are each -Et.

In one embodiment, —R⁹ and —R¹¹ are the same. In one embodiment —R⁹ and —R¹¹ are each -Et.

In one embodiment, —R¹⁰ and —R¹² are the same. In one embodiment, —R¹⁰ and —R¹² are each -Et.

In one embodiment, —R⁹, —R¹⁰, —R¹¹ and —R¹² are the same.

In one embodiment, —R⁹, —R¹⁰, —R¹¹ and —R¹² are each -Et.

In one embodiment, —R⁹ and —R¹⁰, together with the nitrogen atom to which they are bound, form a saturated $C_{3-7}$ heterocycle; and —R¹¹ and —R¹², together with the nitrogen atom to which they are bound, independently form a saturated $C_{3-7}$ heterocycle.

In one embodiment the saturated $C_{3-7}$ heterocycle formed by R⁹ and R¹⁰ and the saturated $C_{3-7}$ heterocycle formed by R¹¹ and R¹² are independently selected from: aziridine, azetidine, pyrrolidine, imidazolidine, pyrazolidine, oxazolidine, isoxazolidine, piperidine, piperazine, morpholine, azepine, oxazepine, and diazepine.

In one embodiment the saturated $C_{3-7}$ heterocycle formed by R⁹ and R¹⁰ and the saturated $C_{3-7}$ heterocycle formed by R¹¹ and R¹² are independently selected from: morpholine, piperidine, and pyrrolidine.

In one embodiment the saturated $C_{3-7}$ heterocycle is morpholine.

In one embodiment the saturated $C_{3-7}$ heterocycle is piperidine.

In one embodiment the saturated $C_{3-7}$ heterocycle is pyrrolidine.

In one embodiment the saturated $C_{3-7}$ heterocycle formed by R⁹ and R¹⁰ and the saturated $C_{3-7}$ heterocycle formed by R¹¹ and R¹² are the same.

Preferred Compounds

In general, the present invention relates to one or more compounds selected from the following compounds, and their use in medicine:

| Compound | Structure and Name |
|---|---|
| A | 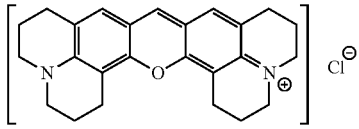<br>2,3,6,7,12,13,16,17-Octahydro-1H,5H,11H,15H-diquinolizino-[1,9-bc: 1′,9′-hi] xanthylium chloride |
| B | 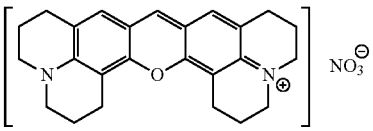<br>2,3,6,7,12,13,16,17-Octahydro-1H,5H,11H,15H-diquinolizino-[1,9-bc: 1′,9′-hi] xanthylium nitrate |
| C | 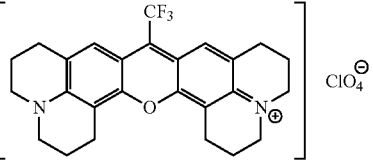<br>8-(Trifluoromethyl)-2,3,5,6,11,12,14,15-octahydro-1H,4H,10H,13H-diquinolizino[9,9a,1-bc; 9′,9a′1′-hi] xanthylium perchlorate |
| D | 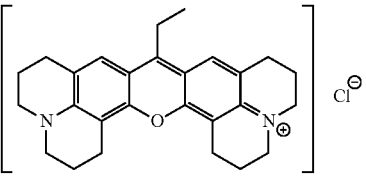<br>8-Ethyl-2,3,6,7,12,13,16,17-octahydro-1H,5H,11H,15H-diquinolizino[1,9-bc; 1′,9′-hi] xanthylium chloride |

-continued

| Compound | Structure and Name |
|---|---|
| E | [xanthylium structure with Et₂N and NEt₂] Cl⁻<br>3,6-Bis-diethylamino xanthylium chloride |
| F | [xanthylium structure with Et₂N and NEt₂] Br⁻<br>3,6-Bis-diethylamino xanthylium bromide |
| G | [xanthylium structure with Et₂N and NEt₂] FeCl₄⁻<br>3,6-Bis-diethylamino xanthylium iron tetrachloride |
| H | [xanthene structure with Et₂N and NEt₂] · 2 HCl<br>3,6-Bis-diethylamino xanthene dihydrochloride |
| I | [xanthylium structure with Et₂N and NEt₂] NO₃⁻<br>3,6-Bis-diethylamino xanthylium nitrate |
| I·HNO₃ | [xanthylium structure with Et₂N and NEt₂] NO₃⁻ HNO₃<br>3,6-Bis-diethylamino xanthylium nitrate·HNO₃ |
| J | [9-ethyl xanthylium structure with Et₂N and NEt₂] Cl⁻<br>9-Ethyl-3,6-bis-diethylamino xanthylium chloride |
| K | [thioxanthylium structure with Et₂N and NEt₂] I⁻<br>3,6-Bis(diethylamino)-thioxanthylium iodide |

-continued

| Compound | Structure and Name |
|---|---|
| L | [thioxanthylium structure with Me₂N and NMe₂] ZnCl₃⁻<br>3,6-Bis(diethylamino)-thioxanthylium zinc trichloride |
| M | [1,9-dimethylthioxanthylium structure with Me₂N and NMe₂] ZnCl₃⁻<br>3,6-Bis(dimethylamino)-1,9-dimethylthioxanthylium zinc trichloride |
| N | [phenazinium structure with Me₂N and NMe₂] Cl⁻<br>3,7-Bis(dimethylamino)-phenazinium chloride |
| O | [oxazinium structure with Me₂N and NMe₂] ClO₄⁻<br>3,7-Bis(dimethylamino)-oxazinium perchlorate |
| AB | [xanthylium structure with Me₂N and NMe₂] NO₃⁻<br>3,6-Bis-dimethylamino xanthylium nitrate |
| AC | [9-(4-diethylanilino) xanthylium structure with Et₂N and NEt₂] NO₃⁻<br>3,6-Bis-diethylamino-9-(4-diethylanilino) xanthylium nitrate |

| Compound | Structure and Name |
|---|---|
| AD | 3,6-Bis-diethylamino-9-(4-nitrophenyl) xanthylium nitrate |
| AE | 1,1,7,7,11,11,17,17-Octamethyl-2,3,6,7,12,13,16,17-octahydro-1H,5H,11H,15H-diquinolizino[1,9-bc: 1',9'-hi] xanthylium nitrate |
| AF | 3,6-Bis-morpholino xanthylium nitrate |
| AG | 3,6-Bis-piperidino xanthylium nitrate |
| AH | 3,6-Bis-pyrrolidino xanthylium nitrate |
| AI | 3,6-Bis-morpholino xanthene dihydrochloride |
| AJ | 3,6-Bis-pyrrolidino xanthene dihydrochloride |
| AK | 3,6-Bis-piperidino xanthene dihydrochloride |
| AL | 2,6,10-Tris-diethylamino-4,8,12-trioxotrianguleum hexafluorophosphate |
| AM | 3-Diethylamino-7-dimethylaminophenazinium chloride |
| AN | 3-Diethylamino-7-dimethylaminooxazinium perchlorate |

In this and all other aspects of the invention, unless context demands otherwise, a compound may be selected from the list consisting of A, B, C, D, E, F, G, H, I, I.HNO$_3$, J, K, L, M, N, O, AB, AC, AD, AE, AF, AG, AH, AI, AJ, AK, AL, AM and AN.

In one embodiment, a compound may be selected from the list consisting of A, B, C, D, E, F, G, H, I, I.HNO$_3$, J, K, L, M, N, and O.

In one embodiment, a compound may be selected from the list consisting of A, B, C, D, E, F, G, H, I, I.HNO$_3$, and J.

In one embodiment, the compound is selected from list consisting of A, B, C, and D.

In one embodiment, the compound is selected from list consisting of B and D.

In one embodiment, the compound is selected from list consisting of E, F, G, H, I, I.HNO$_3$, J, and K.

In one embodiment, the compound is selected from list consisting of E, F, G, I, I.HNO$_3$, J, and K.

In one embodiment, the compound is selected from list consisting of F, I, I.HNO$_3$, and J.

In one embodiment, the compound is selected from list consisting of L, M, N, and O.

In one embodiment, the compound is selected from list consisting of N and O.

In one embodiment, the compound is selected from list consisting of K, L, and, M.

In one embodiment, the compound is selected from list consisting of L and M.

In one embodiment, the compound is selected from list consisting of AB, AC, AD, AE, AF, AG, AH, AI, AJ, AK, and AL.

In one embodiment, the compound is selected from the list consisting of AB, AC, AD, AE, AF, AG, AH, AI, AJ, and AK.

In one embodiment, the compound is selected from the list consisting of AC and AD.

In one embodiment, the compound is selected from the list consisting of AF, AG, AH, AI, AJ, and AK.

In one embodiment, the compound is selected from the list consisting of AF, AG and AH.

In one embodiment, the compound is selected from the list consisting of AI, AJ, and AK.

In one embodiment, the compound is selected from the list consisting of AM and AN.

In one embodiment, it is compound A.
In one embodiment, it is compound B.
In one embodiment, it is compound C.
In one embodiment, it is compound D.
In one embodiment, it is compound E.
In one embodiment, it is compound F.
In one embodiment, it is compound G.
In one embodiment, it is compound H.
In one embodiment, it is compound I.
In one embodiment, it is compound I.$HNO_3$.
In one embodiment, it is compound J.
In one embodiment, it is compound K.
In one embodiment, it is compound L.
In one embodiment, it is compound M.
In one embodiment, it is compound N.
In one embodiment, it is compound O.
In one embodiment, it is compound AB.
In one embodiment, it is compound AC.
In one embodiment, it is compound AD.
In one embodiment, it is compound AE.
In one embodiment, it is compound AF.
In one embodiment, it is compound AG.
In one embodiment, it is compound AH.
In one embodiment, it is compound AI.
In one embodiment, it is compound AJ.
In one embodiment, it is compound AK.
In one embodiment, it is compound AL.
In one embodiment, it is compound AM.
In one embodiment, it is compound AN.

In one embodiment the xanthylium compound may be one which is obtained by, or is obtainable by, a method as described herein (see "Methods of Synthesis" below).

Preferred compounds of the present invention are those which show high activity in the assays described herein, particularly the in vitro assay described below. Preferred compounds have a B50 of less than 500, more preferably less than 300, 200, 100, 90, 80, 70, 60, 50, or 40 µM, as determined with reference to the Examples herein.

In one embodiment the xanthylium compound has a RxIndex (RxI) value obtained as determined with reference to the Examples herein of greater than or equal to 150, more preferably greater than or equal to 200, 250, 300, 500, 1000, 1500, or 2000.

The present invention also provides intermediates for use in the preparation of the compounds of the invention. Such intermediates are described below in the methods of synthesis section Isotopic Variation In one embodiment, one or more of the carbon atoms of the compound is $^{11}C$ or $^{13}C$ or $^{14}C$.

In one embodiment, one or more of the carbon atoms of the compound is $^{11}C$.

In one embodiment, one or more of the carbon atoms of the compound is $^{13}C$.

In one embodiment, one or more of the carbon atoms of the compound is $^{14}C$.

In one embodiment, one or more of the nitrogen atoms of the compound is $^{15}N$.

In one embodiment, one or more or all of the carbon atoms of one or more or all of the groups —$R^1$, —$R^2$, —$R^3$, —$R^4$, —$R^9$, —$R^{10}$, $R^{11}$, and —$R^{12}$ is $^{11}C$.

In one embodiment, the groups —$R^1$, —$R^2$, —$R^3$ and —$R^4$ are each —($^{11}CH_2$$^{11}CH_3$).

In one embodiment, the groups —$R^1$, —$R^2$, —$R^3$ and —$R^4$ are each —($^{11}CH_3$).

In one embodiment, the groups —$R^9$, —$R^{10}$, —$R^{11}$ and —$R^{12}$ are each —($^{11}CH_2$$^{11}CH_3$).

In one embodiment, one or more or all of the carbon atoms, where present, of the groups —$R^5$, —$R^{5A}$, —$R^6$, —$R^7$, or —$R^8$ is $^{11}C$.

In one embodiment, one or more or all of the carbon atoms, where present, of the groups —$R^5$, —$R^{5A}$, or —$R^6$ is $^{11}C$.

In one embodiment, one or more or all of the carbon atoms, where present, of the groups —$R^7$ or —$R^8$ is $^{11}C$.

Uses to Reverse or Inhibit the Aggregation of tau Protein.

One aspect of the invention is the use of a xanthylium compound to reverse or inhibit the aggregation of tau protein. This aggregation may be in vitro, or in vivo, and may be associated with a tauopathy disease state as discussed herein.

Also provided are methods of reversing or inhibiting the aggregation of tau protein comprising contacting the aggregate or protein with a compound as described herein.

As discussed below, various tauopathy disorders that have been recognized which feature prominent tau pathology in neurons and/or glia and this term has been used in the art for several years. The similarities between these pathological inclusions and the characteristic tau inclusions in diseases such as AD indicate that the structural features are shared and that it is the topographic distribution of the pathology that is responsible for the different clinical phenotypes observed. In addition to specific diseases discussed below, those skilled in the art can identify tauopathies by combinations of cognitive or behavioural symptoms, plus additionally through the use of appropriate ligands for aggregated tau as visualised using PET or MRI, such as those described in WO02/075318.

Methods of Treatment or Prophylaxis and $1^{st}$ & $2^{nd}$ Medical Uses

One aspect of the present invention pertains to a method of treatment or prophylaxis of a tauopathy condition in a patient, comprising administering to said patient a therapeutically-effective amount of a xanthylium compound, as described herein.

Aspects of the present invention relate to "tauopathies". As well as Alzheimer's disease (AD), the pathogenesis of neurodegenerative disorders such as Pick's disease and Progressive Supranuclear Palsy (PSP) appears to correlate with an accumulation of pathological truncated tau aggregates in the dentate gyrus and stellate pyramidal cells of the neocortex, respectively. Other dementias include fronto-temporal dementia (FTD); parkinsonism linked to chromosome 17 (FTDP-17); disinhibition-dementia-parkinsonism-amyotrophy complex (DDPAC); pallido-ponto-nigral degeneration (PPND); Guam-ALS syndrome; pallido-nigro-luysian degeneration (PNLD); cortico-basal degeneration (CBD); Dementia with Argyrophilic grains (AgD); Dementia pugilistica (DP) wherein despite different topography, NFTs are similar to those observed in AD (H of P. R., Bouras C., Buée L., Delacourte A., Perl D. P. and Morrison J. H. (1992) Differential distribution of neurofibrillary tangles in the cerebral cortex of dementia pugilistica and Alzheimer's disease cases. Acta Neuropathol. 85, 23-30); Chronic traumatic encephalopathy (CTE), a tauopathy including DP as well as repeated and sports-related concussion (McKee, A., Cantu, R., Nowinski, C., Hedley-Whyte, E., Gavett, B., Budson, A., Santini, V., Lee, H.-S., Kubilus, C. & Stern, R. (2009) Chronic traumatic encephalopathy in athletes: progressive tauopathy after repetitive head injury. Journal of Neuropathology & Experimental Neurology 68, 709-735). Others are discussed in Wischik et al. 2000, loc. cit, for detailed discussion—especially Table 5.1).

Abnormal tau in NFTs is found also in Down's Syndrome (DS) (Flament S., Delacourte A. and Mann D. M. A. (1990) Phosphorylation of tau proteins: a major event during the process of neurofibrillary degeneration. A comparative study between AD and Down's syndrome. Brain Res., 516, 15-19). Also Dementia with Lewy bodies (DLB) (Harrington, C. R., Perry, R. H., Perry, E. K., Hurt, J., McKeith, I. G., Roth, M. & Wischik, C. M. (1994) Senile dementia of Lewy body type and Alzheimer type are biochemically distinct in terms of paired helical filaments and hyperphosphorylated tau protein. Dementia 5, 215-228). Tau-positive NFTs are also found in Postencephalitic parkinsonism (PEP) (H of P. R., Charpiot, A., Delacourte A., Buee, L., Purohit, D., Perl D. P. and Bouras, C. (1992) Distribution of neurofibrillary tangles and senile plaques in the cerebral cortex in postencephalitic parkinsonism. Neurosci. Lett. 139, 10-14). Glial tau tangles are observed in Subacute sclerosing panencephalitis (SSPE) (Ikeda K., Akiyama H., Kondo H., Arai T., Arai N. and Yagishita S. (1995) Numerous glial fibrillary tangles in oligodendroglia in cases of Subacute sclerosing panencephalitis with neurofibrillary tangles. Neurosci. Lett., 194, 133-135).

Other tauopathies include Niemann-Pick disease type C (NPC) (Love, S., Bridges, L. R. & Case, C. P. (1995), *Brain*, 118, 119-129); Sanfilippo syndrome type B (or mucopolysaccharidosis III B, MPS III B) (Ohmi, K., Kudo, L. C., Ryazantsev, S., et al. (2009) *PNAS*, 106, 8332-8337; myotonic dystrophies (DM), DM1 (Sergeant, N., Sablonniere, B., Schraen-Maschke, S., et al. (2001) *Human Molecular Genetics*, 10, 2143-2155 and references cited therein) and DM2 (Maurage, C. A., Udd, B., Ruchoux, M. M., et al. (2005) *Neurology*, 65, 1636-1638).

Additionally there is a growing concensus in the literature that a tau pathology may also contribute more generally to cognitive deficits and decline, including in mild cognitive impairment (MCI) (see e.g. Braak, H., Del Tredici, K, Braak, E. (2003) Spectrum of pathology. In Mild cognitive impairment: Aging to Alzheimer's disease edited by Petersen, R. C.; pp. 149-189).

All of these diseases, which are characterized primarily or partially by abnormal tau aggregation, are referred to herein as "tauopathies" or "diseases of tau protein aggregation".

In this and all other aspects of the invention relating to tauopathies, preferably the tauopathy is selected from the list consisting of the indications above, i.e., AD, Pick's disease, PSP, FTD, FTDP-17, DDPAC, PPND, Guam-ALS syndrome, PNLD, and CBD and AgD, DS, SSPE, DP, PEP, DLB, CTE and MCI.

In one preferred embodiment the tauopathy is Alzheimer's disease (AD).

One aspect of the present invention pertains to a xanthylium compound, as described herein, for use in a method of treatment or prophylaxis (e.g., of a tauopathy condition) of the human or animal body by therapy.

One aspect of the present invention pertains to use of a xanthylium compound, as described herein, in the manufacture of a medicament for use in the treatment or prophylaxis of a tauopathy condition.

A further embodiment is a method of treatment or prophylaxis of a disease of tau protein aggregation as described herein, which method comprises administering to a subject a xanthylium compound, or therapeutic composition comprising the same, such as to inhibit the aggregation of the tau protein associated with said disease state.

Other Methods and Uses

In a further embodiment there is disclosed a xanthylium compound, or therapeutic composition comprising the same, for use in a method of treatment or prophylaxis of a disease of tau protein aggregation as described above, which method comprises administering to a subject the xanthylium compound or composition such as to inhibit the aggregation of the tau protein associated with said disease state.

In a further embodiment there is disclosed use of a xanthylium compound in the preparation of a medicament for use in a method of treatment or prophylaxis of a disease of tau protein aggregation as described above, which method comprises administering to a subject the medicament such as to inhibit the aggregation of the tau protein associated with said disease state.

In one embodiment there is disclosed a method of regulating the aggregation of a tau protein in the brain of a mammal, which aggregation is associated with a disease state as described above, the treatment comprising the step of administering to said mammal in need of said treatment, a prophylactically or therapeutically effective amount of an inhibitor of said aggregation, wherein the inhibitor is a xanthylium compound.

One aspect of the invention is a method of inhibiting production of protein aggregates (e.g. in the form of paired helical filaments (PHFs), optionally in neurofibrillary tangles (NFTs)) in the brain of a mammal, the treatment being as described herein.

In one aspect the invention provides a drug product for the treatment of a disease state associated with tau protein aggregation in a mammal suffering therefrom, comprising a container labeled or accompanied by a label indicating that the drug product is for the treatment of said disease, the container containing one or more dosage units each comprising at least one pharmaceutically acceptable excipient and, as an active ingredient, an isolated pure xanthylium compound of the invention.

Compositions, Formulations and Purity

In one embodiment, the xanthylium compound may be provided or used in a composition which is equal to or less than 100, 99, 98, 97, 96, 95, 94, 93, 92, 91, or 90% pure.

One aspect of the present invention pertains to a dosage unit (e.g., a pharmaceutical tablet or capsule) comprising 20 to 300 mg of a xanthylium compound as described herein (e.g., obtained by, or obtainable by, a method as described herein; having a purity as described herein; etc.), and a pharmaceutically acceptable carrier, diluent, or excipient.

In one embodiment, the dosage unit is a tablet.

In one embodiment, the dosage unit is a capsule.

Dosage units (e.g., a pharmaceutical tablet or capsule) comprising 20 to 300 mg of a xanthylium compound as described herein and a pharmaceutically acceptable carrier, diluent, or excipient are discussed in more detail hereinafter.

In one embodiment, the amount is 30 to 200 mg.

In one embodiment, the amount is about 25 mg.

In one embodiment, the amount is about 35 mg.

In one embodiment, the amount is about 50 mg.

In one embodiment, the amount is about 70 mg.

In one embodiment, the amount is about 125 mg.

In one embodiment, the amount is about 175 mg.

In one embodiment, the amount is about 250 mg.

In one embodiment, the pharmaceutically acceptable carrier, diluent, or excipient is or comprises one or both of a glyceride (e.g., Gelucire 44/14®; lauroyl macrogol-32 glycerides PhEur, USP) and colloidal silicon dioxide (e.g., 2% Aerosil 200®; Colliodal Silicon Dioxide PhEur, USP).

Formulations

While it is possible for the xanthylium compound to be used (e.g., administered) alone, it is often preferable to present it as a composition or formulation.

In one embodiment, the composition is a pharmaceutical composition (e.g., formulation, preparation, medicament) comprising a xanthylium compound, as described herein, and a pharmaceutically acceptable carrier, diluent, or excipient.

In one embodiment, the composition is a pharmaceutical composition comprising at least one xanthylium compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, *Handbook of Pharmaceutical Additives,* 2nd Edition (eds. M. Ash and I. Ash), 2001 (Synapse Information Resources, Inc., Endicott, N.Y. , USA), *Remington's Pharmaceutical Sciences,* 20th edition, pub. Lippincott, Williams & Wilkins, 2000; and *Handbook of Pharmaceutical Excipients,* 2nd edition, 1994.

Another aspect of the present invention pertains to methods of making a pharmaceutical composition comprising admixing at least one [$^{11}$C]-radiolabelled xanthylium or xanthylium-like compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable," as used herein, pertains to compounds, ingredients, materials, compositions, dosage forms, etc., which are, within the scope of sound medical judgment, suitable for use in contact with the tissues of the subject in question (g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the xanthylium compound, and compositions comprising the xanthylium compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the xanthylium compound is administered to a human patient according to the following dosage regime: about 50 or about 75 mg, 3 or 4 times daily.

In one embodiment, the xanthylium compound is administered to a human patient according to the following dosage regime: about 100 or about 125 mg, 2 times daily.

Preferred Combination Therapies

Combination treatments and therapies, in which two or more treatments or therapies are combined, for example, sequentially or simultaneously, are discussed in more detail hereinafter. Thus it will be understood that any of the medical uses or methods described herein may be used in a combination therapy.

In one embodiment, a treatment of the invention (e.g., employing a compound of the invention) is in combination with a cholinesterase inhibitor such as donepezil (Aricept™) rivastigmine (Exelon™) or galantamine (Reminyl™).

In one embodiment, a treatment of the invention (e.g., employing a compound of the invention) is in combination with an NMDA receptor antagonist such as memantine (Ebixa™, Namenda™).

In one embodiment, a treatment of the invention (e.g. employing a compound of the invention) is in combination with a muscarinic receptor agonist.

In one embodiment, a treatment of the invention (e.g. employing a compound of the invention) is in combination with an inhibitor of amyloid precursor protein to beta-amyloid (e.g., an inhibitor of amyloid precursor protein processing that leads to enhanced generation of beta-amyloid).

Ligands and Labels

Xanthylium compounds discussed herein that are capable of inhibiting the aggregation of tau protein will also be capable of acting as ligands or labels of tau protein (or aggregated tau protein). Thus, in one embodiment, the xanthylium compound is a ligand of tau protein (or aggregated tau protein).

Such xanthylium compounds (ligands) may incorporate, be conjugated to, be chelated with, or otherwise be associated with, other chemical groups, such as stable and unstable detectable isotopes, radioisotopes, positron-emitting atoms, magnetic resonance labels, dyes, fluorescent markers, antigenic groups, therapeutic moieties, or any other moiety that may aid in a prognostic, diagnostic or therapeutic application.

For example, as noted above, in one embodiment, the xanthylium compound is as defined above, but with the additional limitation that the compound incorporates, is conjugated to, is chelated with, or is otherwise associated with one or more (e.g., 1, 2, 3, 4, etc.) isotopes, radioisotopes, positron-emitting atoms, magnetic resonance labels, dyes, fluorescent markers, antigenic groups, or therapeutic moieties.

In one embodiment, the xanthylium compound is a ligand as well as a label, e.g., a label for tau protein (or aggregated tau protein), and incorporates, is conjugated to, is chelated with, or is otherwise associated with, one or more (e.g., 1, 2, 3, 4, etc.) detectable labels.

For example, in one embodiment, the xanthylium compound is as defined above, but with the additional limitation that the compound incorporates, is conjugated to, is chelated with, or is otherwise associated with, one or more (e.g., 1, 2, 3, 4, etc.) detectable labels.

Labelled xanthylium compounds (e.g., when ligated to tau protein or aggregated tau protein) may be visualised or detected by any suitable means, and the skilled person will appreciate that any suitable detection means as is known in the art may be used.

For example, the xanthylium compound (ligand-label) may be suitably detected by incorporating a positron-emitting atom (e.g., $^{11}C$) (e.g., as a carbon atom of one or more alkyl group substituents, e.g., methyl group substituents) and detecting the compound using positron emission tomography (PET) as is known in the art.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

Routes of Administration

The xanthylium compound, or pharmaceutical composition comprising it, may be administered to a subject/patient by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal (including, e.g., intracatheter injection into the brain); by implant of a depot or reservoir, for example, subcutaneously or intramuscularly.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Suitable subjects for the method may be selected on the basis of conventional factors. Thus the initial selection of a patient may involve any one or more of: rigorous evaluation by experienced clinician; exclusion of non-AD diagnosis as far as possible by supplementary laboratory and other investigations; objective evaluation of level of cognitive function using neuropathologically validated battery.

In one embodiment, the subject/patient is not a human.

The invention will now be further described with reference to the following non-limiting Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

Methods of Synthesis

Methods for the chemical synthesis of compounds of the present invention are described in the Examples herein. These and/or other well known methods may be modified and/or adapted in known ways in order to facilitate the synthesis of other compounds of the present invention.

Thus one aspect of the invention provides a method of synthesising a compound of the invention as described herein, described, or substantially as described, with reference to any of the Examples hereinafter.

The invention further provides a xanthylium compound of the invention which is obtained by or is obtainable by, a method as described herein.

One aspect of the present invention pertains to methods for the preparation of xanthylium compounds, as described herein.

The present invention also provides intermediate compounds for use in the preparation of the compounds of the invention.

Compounds (IVa) and (IVb)

The compounds of formula (Ic) may be prepared from a compound of formula (IVa) and the salts thereof, the compounds of formula (I) may be prepared from a compound of formula (IVd) and the salts thereof, and the compounds of formula (IIa) and (III) may be prepared from the compound of formula (IVb) and the salts thereof:

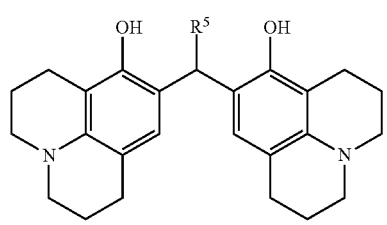

(IVa)

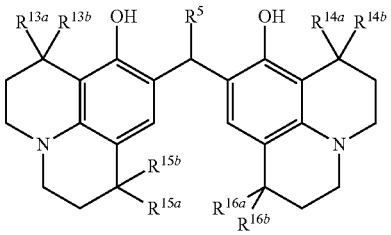

(IVd)

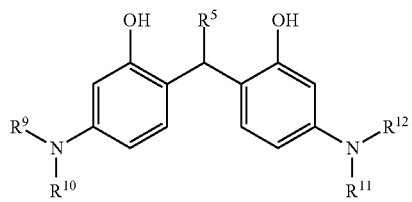

(IVb)

wherein substituents —$R^5$, —$R^9$ to —$R^{12}$, —$R^{13a}$, —$R^{13b}$, —$R^{14a}$, —$R^{14b}$, —$R^{15a}$, —$R^{15b}$, —$R^{16a}$, and —$R^{16b}$ are as defined for the compounds of formula (I), (Ic), (IIa) and (III) as appropriate.

In one aspect of the invention there is provided a compound of formula (IVa) and salts thereof, where —$R^5$ is saturated $C_{1-6}$alkyl, which is unsubstituted or substituted with one or more substituents —$R^{5A}$, and —$R^{5A}$ is as defined for the compounds of formula (I).

In one embodiment, there is provided a compound of formula (IVa) with the proviso that —$R^5$ is not —$CF_3$.

In another aspect of the invention there is provided a compound of formula (IVb) and salts thereof, where —$R^9$ to —$R^{12}$ are defined according to the compounds of formula (IIa) and (III), and —$R^5$ is saturated $C_{1-6}$alkyl, which is unsubstituted or substituted with one or more substituents —$R^{5A}$, where —$R^{5A}$ is as defined for the compounds of formula (IIa) and (III).

In one aspect of the invention there is provided a method of preparing a compound of formula (IVa), the method comprising the step of reacting a mixture of 8-hydroxyjulolidine and a compound $R^5$—CHO in a solvent at room temperature or above, wherein —$R^5$ is as defined for the compounds of formula (IVa).

In another aspect of the invention there is provided a method of preparing a compound of formula (IVb) from a compound of formula (V):

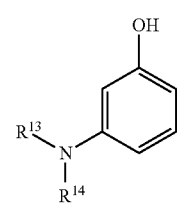

(V)

wherein —$R^{13}$ and —$R^{14}$ are each independently saturated $C_{1-6}$alkyl.

In one embodiment, —$R^{13}$ and —$R^{14}$ are each independently saturated $C_{2-6}$alkyl.

In one embodiment, the $C_{2-6}$alkyl groups are selected from: linear $C_{2-6}$alkyl groups, such as -Et, -nPr, -iPr, and -nBu; branched $C_{3-4}$alkyl groups, such as -iPr, -iBu, -sBu, and -tBu; and cyclic $C_{3-4}$alkyl groups, such as -cPr and -cBu.

In one embodiment, each —$R^{13}$ and —$R^{14}$ is independently saturated aliphatic $C_{1-4}$alkyl.

In one embodiment, each —$R^{13}$ and —$R^{14}$ is independently saturated aliphatic $C_{2-4}$alkyl.

In one embodiment each —$R^{13}$ and —$R^{14}$ is independently selected from -Me, -Et; -n-Pr, -iso-Pr, -n-Bu, -sec-Bu, -iso-Bu, and -tert-Bu.

In one embodiment, —$R^{13}$ and —$R^{14}$ are the same.

In one embodiment, —$R^{13}$ and —$R^{14}$ are each -Et. In one embodiment, —$R^{13}$ and —$R^{14}$ are each -Me.

The method comprises the step of reacting a mixture of a compound of formula (V) and a compound $R^5$—CHO in a solvent at room temperature or above, wherein —$R^5$ is as defined for the compounds of formula (IVb).

The preferences for —$R^5$ for the compounds of formula (I) are also applicable to the compounds of formula (IVa) and (IVb), and compound $R^5$—CHO, where appropriate.

Where —$R^5$ is —H, the compound $R^5$—CHO is formalin. Where —$R^5$ is -Et, the compound $R^5$—CHO is propionaldehyde.

In the methods described above, the reaction may be performed at 35° C. or above, 40° C. or above, 50° C. or above, or 55° C. or above.

In one embodiment, the temperature may be performed at ±2° C. of the temperature specified.

The solvent may be a $C_{1-4}$alkyl alcohol. The solvent may be methanol or ethanol.

The reaction may be performed in the presence of an acid. Preferably the acid is hydrochloric acid. In one embodiment, the compounds of formula (IVa) and (IVb) may be obtained as hydrochloride salts.

In one embodiment, the method further comprises the step of adding sufficient base to the product of the reaction such that the resulting mixture has a pH of 7 or more. In one embodiment the compounds of formula (IVa) and (IVb) may be obtained as a free base.

Compound P

In one embodiment, there is provided a method of preparing a compound P and the salts thereof, the method comprising the step of reacting a mixture of 8-hydroxyjulolidine and formalin in a solvent at room temperature or above.

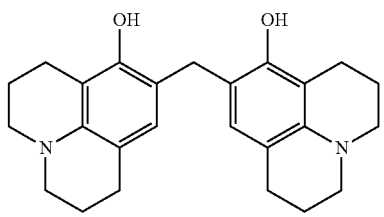

7,7'-Methylenebis-2,3,6,7-tetrahydrobenzo[i,j]quinolizine-8,8'-diol

The solvent may be methanol.

The reaction mixture may be heated to reflux.

The reaction may be performed at 35° C. or above, 40° C. or above, 50° C. or above, or 55° C. or above.

In one embodiment the reaction is performed at 55° C. or above.

In one embodiment the temperature may be performed at ±2° C. of the temperature specified.

The reaction may be performed in the presence of an acid. Preferably the acid is hydrochloric acid. In one embodiment, compound P may be obtained as a hydrochloride salt.

In one embodiment, the method further comprises the step of adding sufficient base to the product of the reaction such that the resulting mixture has a pH of 7 or more. In one embodiment, compound P may be obtained as a free base.

Compound P finds use as an intermediate in the synthesis of compounds A and B. In one aspect of the methods described herein, the hydrochloride salt of compound P finds use in the synthesis of compounds of formula (I), and preferably the synthesis of compounds A and B.

The method described herein provides a greater yield of compound P than described previously in U.S. Pat. No. 3,932,415. The present method has a yield of 81%, whilst the method described in U.S. Pat. No. 3,932,415 is said to have a yield of 68%. Furthermore, compound P may be obtained substantially free of impurities in the present method without the need for column chromatography in contrast to the method of U.S. Pat. No. 3,932,415.

Compound Q

The present invention provides an intermediate compound Q and the salts thereof:

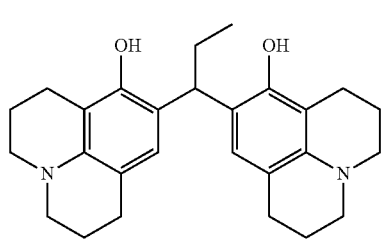

7,7'-Propylidinebis-2,3,6,7-tetrahydrobenzo[i,j]quinolizine-8,8'-diol

Compound Q finds use as an intermediate in the synthesis of compound D.

In one embodiment, there is provided a method of preparing a compound of formula Q and the salts thereof, the method comprising the step of reacting a mixture of 8-hydroxyjulolidine and propionaldehyde in a solvent at room temperature or above.

The solvent may be ethanol.

The reaction may be performed at about 35° C. or above, or about 40° C. or above. In one embodiment the reaction is performed at about 40° C. or above.

In one embodiment the reaction may be performed at ±2° C. of the temperature specified.

The reaction may be performed in the presence of an acid. Preferably the acid is hydrochloric acid. In one embodiment, compound Q may be obtained as a hydrochloride salt.

In one embodiment, the method further comprises the step of adding sufficient base to the product of the reaction such that the resulting mixture has a pH of 7 or more. In one embodiment, compound Q may be obtained as a free base.

Compound R

The present invention provides an intermediate compound R and the salts thereof:

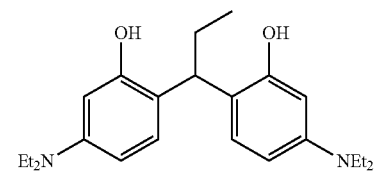

5,5'-Bis-diethylamino-2,2'-propylidine-di-phenol

Compound R finds use as an intermediate in the synthesis of compound J.

In one embodiment, there is provided a method of preparing a compound of formula R and the salts thereof, the method comprising the step of reacting a mixture of 3-diethylaminophenol and propionaldehyde in a solvent at room temperature or above.

The solvent may be methanol.

The reaction may be performed at about 35° C. or above, or about 40° C. or above.

In one embodiment the reaction is performed at about 40° C. or above.

In one embodiment the reaction may be performed at ±2° C. of the temperature specified.

The reaction may be performed in the presence of an acid. Preferably the acid is hydrochloric acid. In one embodiment, compound R may be obtained as a hydrochloride salt.

In one embodiment, the method further comprises the step of adding sufficient base to the product of the reaction such that the resulting mixture has a pH of 7 or more. In one embodiment, compound R may be obtained as a free base.

Compounds (I), (IIa) or (III)

In one aspect of the invention there is provided a method of preparing a compound of formula (I), (IIa) or (III), the method comprising the steps of (i) reacting a compound of formula (IVa) or (IVb) with acid; and (ii) subsequently adding sufficient base to the reaction mixture such that the resulting mixture has a pH of 7 or more.

The compound of formula (IVa) may be used to prepare compounds of formula (I). The compound of formula (IVb) may be used to prepare compounds of formula (II) and (III).

The acid may be sulfuric acid.

Step (i) may comprise reacting a compound of formula (IVa) or (IVb) with acid at 40° C. or above, 60° C. or above, or 80° C. or above.

Step (ii) may comprise adding sufficient base to the reaction mixture such that the resulting mixture has a pH of 8 or more, or 9 or more.

Step (ii) may comprise adding sufficient base to the reaction mixture such that the resulting mixture has a pH of around 7-8.

Step (ii) may comprise adding sufficient sodium hydroxide to the reaction mixture such that the resulting mixture has a pH of 7 or more. The sodium hydroxide may be an aqueous solution.

During the addition of the base, the mixture may be maintained at a temperature of 20° C. or below.

The method described herein may provide a greater yield of the product, compared to the reactions that have been previously described in the art.

In another aspect of the invention there is provided a method of preparing a compound of formula (I), (IIa) or (III), the method comprising the steps of (i) reacting a compound of formula (IVa) or (IVb) with acid; and (ii) subsequently adding an oxidant to the product of step (i).

In step (ii) the oxidant is independently selected from nitric acid, chloranil, benzoquinone, DDQ, sodium hypochlorite, hydrogen peroxide, potassium permanganate, chromium-containing oxidants, manganese dioxide, sodium nitrite, isopentyl nitrite, tert-butyl nitrite and $FeCl_3$. In one embodiment, the oxidant is nitric acid. In another embodiment the oxidant is $FeCl_3$. The inventors have established that use of the oxidant $FeCl_3$ allows the preparation of product having a greater purity compared to the products produced using other oxidants.

In one embodiment, step (i) comprises the step of (i) reacting a compound of formula (IVa) or (IVb) with acid and subsequently adding sufficient base to the reaction mixture such that the resulting mixture has a pH of 7 or more.

In one aspect of the invention there is provided a method for the preparation of compounds formula (I), (IIa) or (III) where X is $NO_3^-$, the method comprising the steps of (i) reacting a compound of formula (IVa) or (IVb) with acid and, and then treating the product with $FeCl_3$ and optionally an acid, and (ii) subsequently adding nitric acid to the product of step (i).

It has been found that the addition of nitric acid to the iron tetrachloride product formed in this step (i) provides compounds (I), (IIa) or (III) with low levels of iron. Excessive levels of iron are generally unacceptable in pharmaceutical products. It has also been established such compounds may be produced having low levels of other pharmaceutically unacceptable metals such as lead, aluminium, and mercury.

Compound A or Compound B

In one aspect of the invention there is provided a method of preparing compound A or compound B, the method comprising the steps of: (i) reacting compound P with acid; and (ii) subsequently adding sufficient base to the reaction mixture such that the resulting mixture has a pH of 7 or more.

The preferences for the method for the preparation of compounds of formula (I) described above, also apply to the methods for the preparation of compounds A and B, where appropriate.

The method described herein may provides a greater yield of compound A than described previously in U.S. Pat. No. 3,932,415. The present method has a yield of 52%, whilst the method described in U.S. Pat. No. 3,932,415 gives 33%.

Compound E, Compound F, Compound H or Compound I

In one aspect of the invention there is provided a method of preparing compound E, compound F, compound H, or compound I, the method comprising the steps of: (i) reacting a compound of formula (IVb) with acid; and (ii) adding sufficient base to the reaction mixture such that the resulting mixture has a pH of 7 or more.

The preferences for the method for the preparation of compounds of formula (IIa) described above, also apply to the methods for the preparation of compounds E, F, H, and I, where appropriate.

Compound AB, Compound AC, Compound AD, Compound AF, Compound AG, Compound AH, Compound AI, Compound AJ, and Compound AK In one aspect of the invention there is provided a method of preparing compound AB, compound AC, compound AD, compound AF, compound AG, compound AH, compound AI, compound AJ, and compound AK, the method comprising the steps of: (i) reacting a compound of formula (IVb) with acid; and (ii) adding sufficient base to the reaction mixture such that the resulting mixture has a pH of 7 or more.

The preferences for the method for the preparation of compounds of formula (IIa) described above, also apply to the methods for the preparation of compounds AB, AC, AD, AF, AG, AH, AI, AJ, and AK, where appropriate.

Compound (Ia)

In one aspect of the invention there is provided a method of preparing a compound of formula (Ia):

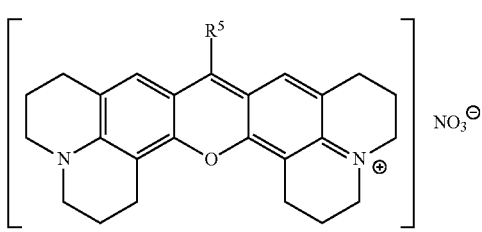

(Ia)

wherein —R⁵ is as defined according to the compounds of formula (I), the method comprising the steps of (i) reacting a compound of formula (IVa) with acid; and (ii) subsequently adding an oxidant to the product of step (i).

The acid may be sulfuric acid.

Step (i) may comprise reacting a compound of formula (IVa) with acid at 40° C. or above, 60° C. or above, or 80° C. or above.

Step (i) may comprise reacting a compound of formula (IVa) with acid then adding sufficient base to the reaction mixture such that the resulting mixture has a pH of 7 or more. Sufficient base may be added to the reaction mixture such that the resulting mixture has a pH of 8 or more, or 9 or more. The step may comprise adding sufficient sodium hydroxide to the reaction mixture such that the resulting mixture has a pH of 7 or more. The sodium hydroxide may be an aqueous solution.

During the addition of the base, the mixture may be maintained at a temperature of 20° C. or below.

In step (ii), the oxidant is preferably nitric acid or FeCl₃.

In step (ii), nitric acid may be added to the product of step (i), and the resulting solid may be isolated from the reaction mixture.

In step (ii), nitric acid may be added to the product of step (i), and the resulting mixture heated to 40° C. or above, or 50° C. or above.

The resulting solid may be further treated with nitric acid and the solid product may be isolated from the reaction mixture.

Compound B

In one aspect of the invention there is provided a method of preparing compound B, the method comprising the steps of: (i) reacting compound P with acid; and (ii) subsequently adding nitric acid to the product of step (i).

The preferences for the method for the preparation of compounds of formula (Ia) described above, also apply to the methods for the preparation of compound B, where appropriate.

Compound (Ib)

In one aspect of the invention there is provided a method of preparing a compound of formula (Ib) from a compound of formula (IVc).

The compound of formula (Ib) is represented thus:

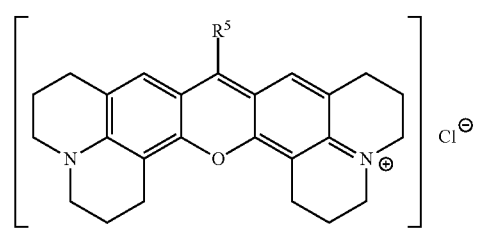

(Ib)

wherein —R⁵ is independently saturated C₁₋₆alkyl, which is unsubstituted or substituted with one or more substituents —R⁵ᴬ, where —R⁵ᴬ is as defined according to the compounds of formula (I).

The compound of formula (IVc) is represented thus:

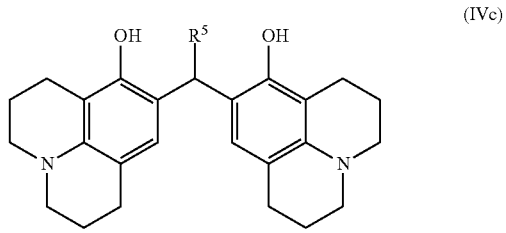

(IVc)

wherein —R⁵ is independently saturated C₁₋₆alkyl, which is unsubstituted or substituted with one or more substituents —R⁵ᴬ, where —R⁵ᴬ is as defined according to the compounds of formula (I).

The method comprises the steps of (i) reacting a compound of formula (IVc) with acid; and (ii) adding sufficient base to the reaction mixture such that the resulting mixture has a pH of 7 or more; then (iii) subsequently adding hydrochloric acid and sodium nitrite to the reaction mixture, The acid may be sulfuric acid.

Step (ii) may comprise adding sufficient base to the reaction mixture such that the resulting mixture has a pH of 8 or more, or 9 or more.

Step (ii) may comprise adding sufficient base to the reaction mixture such that the resulting mixture has a pH of around 7-8.

Step (ii) may comprise adding sufficient sodium hydroxide to the reaction mixture such that the resulting mixture has a pH of 7 or more. The sodium hydroxide may be an aqueous solution.

Compound D

In one aspect of the invention there is provided a method of preparing compound D, the method comprising the steps of: (i) reacting 7,7'-propylidinebis(2,3,6,7-tetrahydrobenzo[i,j]quinolizine-8,8'-diol) with acid; and (ii) adding sufficient base to the reaction mixture such that the resulting mixture has a pH of 7 or more; then (iii) subsequently adding hydrochloric acid and sodium nitrite to the reaction mixture, The preferences for the method for the preparation of compounds of formula (Ib) described above, also apply to the methods for the preparation of compound D, where appropriate.

Compound (Ie)

In one aspect of the invention there is provided a method of preparing a compound of formula (Ie) from a compound of formula (IVe).

The compound of formula (Ie) is represented thus:

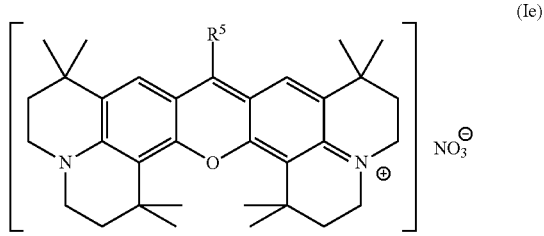

(Ie)

wherein —$R^5$ is as defined according to the compounds of formula (I).

The compound of formula (IVe) is represented thus:

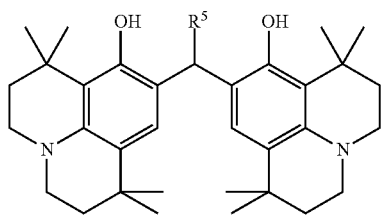

(IVe)

wherein —$R^5$ is as defined according to the compounds of formula (I).

The method comprises the steps of (i) reacting a compound of formula (IVe) with acid; and (ii) subsequently adding an oxidant to the product of step (i).

The acid may be sulfuric acid.

Step (i) may comprise reacting a compound of formula (IVe) with acid at 40° C. or above, 50° C. or above, or 65° C. or above.

Step (i) may comprise reacting a compound of formula (IVe) with acid then neutralizing the reaction mixture. Sufficient base may be added to the reaction mixture such that the resulting mixture has a pH of 7 or more, 8 or more, or 9 or more. The step may comprise adding sufficient sodium hydroxide to the reaction mixture such that the resulting mixture has a pH of 7 or more. The sodium hydroxide may be an aqueous solution.

During the addition of the base, the mixture may be maintained at a temperature of 20° C. or below, or 18° C. or below.

In step (ii), the oxidant comprises $FeCl_3$.

In step (ii), the oxidant may be added to the product of step (i), and the resulting solid may be isolated from the reaction mixture.

The resulting solid may be further treated with nitric acid and the solid product may be isolated from the reaction mixture.

Compound AE

In one aspect of the invention there is provided a method of preparing compound AE, the method comprising the steps of: (i) reacting 1,1,7,7,-tetramethyl-8-hydroxyjulolidine with acid; and (ii) subsequently adding sufficient base to the reaction mixture such that the resulting mixture has a pH of 7 or more.

The preferences for the method for the preparation of compounds of formula (I) described above, also apply to the methods for the preparation of compounds AE, where appropriate.

Compound (IId)

In one aspect of the invention there is provided a method of preparing a compound of formula (IId) from a compound of formula (IVb).

The compound of formula (IId) is represented thus:

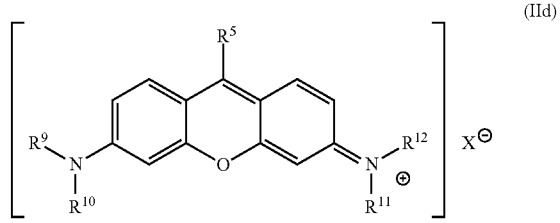

(IId)

wherein $X^-$ is a counter ion selected from $Cl^-$, $Br^-$ and $NO_3^-$;

—$R^9$, —$R^{10}$, —$R^{11}$ and —$R^{12}$ are as defined according to the compounds of formula (IIa), the method comprising the steps of (i) reacting a compound of formula (III) with acid; and (ii) subsequently adding hydrochloric acid, hydrobromic acid or nitric acid to the product of step (i); with the proviso that where $X^-$ is $Cl^-$, —$R^5$ is not —H.

In one embodiment, the method comprises the step of preparing a compound of formula (IId) where the group —$R^5$ is independently saturated $C_{1-6}$alkyl, which is unsubstituted or substituted with one or more substituents —$R^{5A}$.

In one embodiment $X^-$ is a counter ion selected from $Br^-$ and $NO_3^-$. Consequently step (ii) comprises subsequently adding hydrobromic acid or nitric acid to the product of step (i).

In step (ii) hydrobromic acid may be used to generate a product where $X^-$ is $Br^-$. Step (ii) may comprise subsequently adding hydrobromic acid to the product of step (i), and then adding an alkali metal nitrite to the subsequent mixture. The alkali metal nitrite may be sodium nitrite.

In the embodiment above, step (ii) comprises subsequently adding hydrobromic acid to the product of step (i). Alternatively, step (ii) comprises subsequently nitric acid to the product of step (i), and then subsequently treating with product with KBr. In this embodiment, the method comprises the step of (i) reacting a compound of formula (III) with acid, and then subsequently treating the product with $FeCl_3$ and optionally an acid.

Step (i) may comprise reacting a compound of formula (III) with sulfuric acid.

Step (i) may comprise reacting a compound of formula (III) with acid then subsequently adding sufficient base to the reaction mixture such that the resulting mixture has a pH of 7 or more. The base may be sodium hydroxide. During the addition of the base, the mixture may be maintained at a temperature of 20° C. or below.

In step (ii) nitric acid may be used to generate a product where $X^-$ is $NO_3^-$.

In an alternative embodiment, the method comprises the step of (i) reacting a compound of formula (III) with acid, and then subsequently treating the product with $FeCl_3$ and optionally an acid. The acid may be hydrochloric acid. Step (ii) comprises subsequently adding nitric acid to the product of step (i).

As noted above, It has been found that the addition of nitric acid to the iron tetrachloride product formed in this step (i) provides compound (IId) with low levels of iron and other metals.

In step (ii) hydrochloric acid may be used to generate a product where $X^-$ is $Cl^-$. Step (ii) may comprise subsequently adding hydrochloric acid to the product of step (i), and then adding an alkali metal nitrite to the subsequent mixture. The alkali metal nitrite may be sodium nitrite.

Compound F, Compound I or Compound J

In one aspect of the invention there is provided a method of preparing compound F or compound I, the method comprising the steps of: (i) reacting 5,5'-bis-diethylamino-2,2'-methandiyl-di-phenol or 5,5'-bis-diethylamino-2,2'-propylidine-di-phenol with acid; and (ii) subsequently adding hydrobromic acid, nitric acid or hydrochloric acid to the product of step (i).

The preferences for the method for the preparation of compounds of formula (IId) described above, also apply to the methods for the preparation of compounds F, I or J, where appropriate.

Compound (IIe)

In an alternative aspect of the invention, there is provided a method of preparing a compound of formula (IIe) from a compound of formula (IVb), wherein the compound of formula (IIe) is as defined according to the compound of formula (IId) except that X is $FeCl_4^-$.

The method comprising the steps of (i) reacting a compound of formula (III) with acid; and (ii) subsequently adding $FeCl_3$ to the product of step (i).

Step (i) may comprise reacting a compound of formula (III) with sulfuric acid.

Compound (IIb)

The present invention provides methods of preparing compounds of formula (IIb) as described herein.

Compound M

In one aspect of the invention there is provided a method of preparing compound M, the method comprising the step of reacting 4,4'-bis(dimethylamino)diphenylmethane with sulfur and acid.

The acid in step (i) may be sulfuric acid.

In step (i), the sulfur may be added to the acid, followed subsequently by addition of 4,4'-bis(dimethylamino)diphenylmethane to the reaction mixture. The reaction mixture may be kept at 5° C. prior to addition of bis(dimethylamino)diphenylmethane. The reaction mixture may be maintained at 20° C. or below during addition of bis(dimethylamino)diphenylmethane.

The method may comprise the additional step of (ii) subsequently adding zinc chloride to the product of step (i).

EXAMPLES

Example 1

Methods of Synthesis

The following syntheses are provided solely for illustrative purposes and are not intended to limit the scope of the invention, as described herein.

Synthesis 1

2,3,6,7,12,13,16,17-Octahydro-1H,5H,11H,15H-diquinolizino[1,9-bc:1',9'-hi]xanthylium chloride

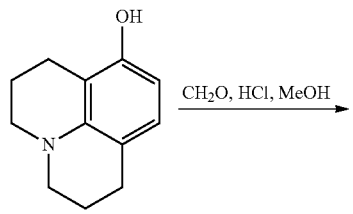

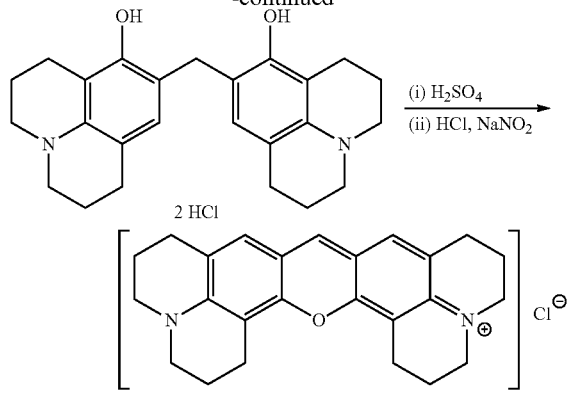

Method A—From U.S. Pat. No. 3,932,415

7,7'-Methylenebis(2,3,6,7-tetrahydrobenzo[i,j]quinolizine-8,8'-diol)

Hydrochloric acid (0.8 cm³, 32%) was added drop wise to a solution of 8-hydroxyjulolidine (3.00 g, 15.9 mmol) in methanol (16 cm³) at 5° C. Formalin (0.593 cm³, 40% in water) was then added to the reaction and the resulting mixture was allowed to stand overnight at 5° C. The mixture was then poured into water (50 cm³) before being neutralised with a saturated solution of sodium bicarbonate. The mixture was extracted with chloroform (3×40 cm³), the combined extracts were dried over sodium sulphate, filtered and the solvent removed under reduced pressure. Column chromatography (3:7 ethyl acetate/hexane) gave the target material as a colourless solid (2.11 g, 68%).

$\delta_H$ (250 MHz, CDCl$_3$): 6.68 (2H, s, CH), 3.64 (2H, s, CH$_2$), 3.00 (8H, t, J$_1$=6 Hz, CH$_2$), 2.67 (4H, J=6 Hz, CH$_2$), 2.60 (4H, t, J$_2$=7 Hz, CH$_2$), 1.97-1.90 (8H, m, CH$_2$); $\delta_c$ (100 MHz, CDCl$_3$): 149.3, 142.7, 127.6, 114.6, 114.5, 108.5, 50.2, 49.4, 30.9, 27.0, 22.5, 21.7, 21.2; $v_{max}$ (KBr)/cm$^{-1}$: 3431, 2927, 2853, 2842, 1618, 1494, 1450, 1350, 1332, 1310, 1281, 1270, 1153, 1132; m/z (ESI): 389.3 (100%, [M–H]$^+$).

2,3,6,7,12,13,16,17-Octahydro-1H,5H,11H,15H-diquinolizino[1,9-bc;1',9'-hi]xanthylium chloride 7,7'-Methylenebis(2,3,6,7-tetrahydrobenzo[i,j]quinolizine-8,8'-diol) (630 mg, 1.62 mmol) was added to concentrated sulphuric acid (2.5 cm³) at 25° C. The resulting solution was heated to 95° C. for 3 hours. The reaction was allowed to cool to room temperature before being poured onto ice (15 cm³). The pH of the solution was adjusted to pH 5 with sodium hydroxide (40%) whilst maintaining the temperature below 15° C. Hydrochloric acid (1 cm³, 32%) was added and the reaction temperature was then allowed to rise to room temperature. A solution of sodium nitrite (222 mg, 3.23 mmol) in water (10 cm³) was added drop wise with stirring and the reaction allowed to stand for 20 hours. The solution was then saturated with sodium chloride before being extracted with chloroform (6×30 cm³). The combined extracts were dried over sodium sulphate, filtered and the solvent removed under reduced pressure to give the target material as a green solid (214 mg, 33%).

Method B 7,7'-Methylenebis(2,3,6,7-tetrahydrobenzo[i,j]quinolizine-8,8'-diol) dihydrochloride Hydrochloric acid (1 cm³, 32%) was added drop wise to a solution of 8-hydroxyjulolidine (3.51 g, 18.57 mmol) in methanol (17.5 cm$^3$) at 5° C. Formalin (0.72 cm$^3$, 40% in water) was then added to the reaction and the resulting mixture was heated to 60° C. for 6 hours. Hydrochloric acid (1 cm$^3$, 32%) was added to the mixture, prior to cooling to room temperature. The product was then collected by filtration, washed with cold methanol (2×5 cm$^3$) and dried under vacuum overnight to give the target material as a colourless solid (3.49 g, 81%).

$\delta_H$ (250 MHz, D$_2$O): 6.76 (2H, s, CH), 3.76 (2H, s, CH$_2$), 3.46-3.38 (8H, m, CH$_2$), 2.78-2.72 (8H, m, CH$_2$), 2.10-2.04 (8H, m, CH$_2$); $\nu_{max}$ (KBr)/cm$^{-1}$: 3463, 2930, 1634, 1477, 1435, 1306, 1224, 1095; m/z (ESI): 391.3 (89%, [M−HCl$_2$]$^+$), 196.7 (100%).

2,3,6,7,12,13,16,17-Octahydro-1H, 5H,11H,15H-diquinolizino[1,9-bc;1',9'-hi]xanthylium chloride 7,7'-Methylenebis(2,3,6,7-tetrahydrobenzo[i,j]quinolizine-8,8'-diol) dihydrochloride (1.00 g, 2.15 mmol) was added to concentrated sulphuric acid (4 cm$^3$) at 25° C. The resulting solution was heated to 90° C. for 3 hours. The reaction was allowed to cool before being poured onto ice (5 cm$^3$). The pH of the solution was adjusted to pH 9 with sodium hydroxide (40%) whilst maintaining a temperature below 15° C. Hydrochloric acid (2 cm$^3$, 32%) was added and the reaction temperature was allowed to rise to room temperature. A solution of sodium nitrite (298 mg, 4.32 mmol) in water (5 cm$^3$) was added drop wise with stirring and the reaction stirred at room temperature for 20 hours. The mixture was filtered and solid collected and dried under vacuum overnight. The solid was then extracted with methanol (15 cm$^3$) and solvent removed under reduced pressure to yield the product as a green solid (455 mg, 52%).

$\delta_H$ (250 MHz, CD$_3$OD): 8.18 (1H, s, CH), 7.32 (2H, s, CH), 3.63 (8H, t, J$_1$=6 Hz, CH$_2$), 3.00 (4H, J$_1$=6 Hz, CH$_2$), 2.87 (4H, t, J$_2$=7 Hz, CH$_2$), 2.09-2.02 (8H, m, CH$_2$); $\delta_c$ (100 MHz, CD$_3$OD): 152.4, 151.7, 142.7, 128.0, 124.1, 113.7, 105.3, 50.8, 50.2, 27.2, 20.6, 19.6, 19.5; $\nu_{max}$ (KBr)/cm$^{-1}$: 3042, 3028, 2921, 1600, 1580, 1517, 1305, 1166, 1147; m/z (ESI): 371.3 (100%, [M−Cl]$^+$).

Synthesis 2

2,3,6,7,12,13,16,17-Octahydro-1H,5H,11H,15H-diquinolizino[1,9-bc:1',9'-hi]xanthylium nitrate

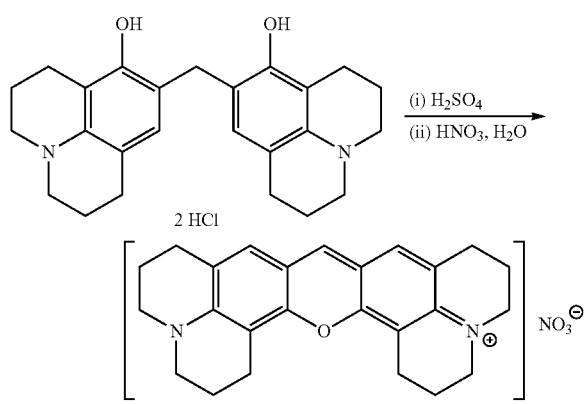

2,3,6,7,12,13,16,17-Octahydro-1H,5H,11H,15H-diquinolizino[1,9-bc:1',9'-hi]xanthylium nitrate 7,7'-Methylenebis(2,3,6,7-tetrahydrobenzo[i,j]quinolizine-8,8'-diol) dihydrochloride (1.00 g, 2.15 mmol) was added to concentrated sulphuric acid (3 cm$^3$) at 25° C. The resulting solution was heated to 90° C. for 2 hours. The reaction was allowed to cool to room temperature before ice water (6 cm$^3$) was added. The pH of the solution was adjusted to pH 9 with sodium hydroxide (40%) whilst maintaining a temperature below 20° C. Nitric acid (0.5 cm$^3$, 70%) was added and the reaction temperature was allowed to rise to room temperature. The reaction was stirred at room temperature for 1 hour, prior to filtration. The solid was collected and dissolved in fresh water (50 cm$^3$). Nitric acid (0.5 cm$^3$, 70%) was added and the reaction stirred at room temperature for 24 hours. The crude product was collected by filtration and dried under vacuum overnight. The solid was re-dissolved in water (25 cm$^3$) and nitric acid (70%) added until turbidity point reached. Mixture heated to 50° C. for 1 hour before cooling to room temperature over 1 hour. Precipitate collected and dried under vacuum overnight to give the product as a green solid (323 mg, 34%).

$\delta_H$ (250 MHz, DMSO-d$_6$): 8.26 (1H, s, CH), 7.35 (2H, s, CH), 3.49-3.41 (8H, m, CH$_2$), 2.90-2.71 (8H, m, CH$_2$), 2.00-1.82 (8H, m, CH$_2$); $\delta_c$ (100 MHz, DMSO-d$_6$): 152.2, 151.6, 143.1, 128.6, 124.0, 113.5, 105.3, 51.0, 50.4, 27.4, 20.7, 19.8, 19.7; $\nu_{max}$ (KBr)/cm$^{-1}$: 2972, 2853, 1600, 1514, 1436, 1361, 1336, 1299, 1200, 1164, 1093, 1030.

Synthesis 3

8-(Trifluoromethyl)-2,3,5,6,11,12,14,15-octahydro-1H,4H,10H,13H-diquinolizino[9,9a,1-bc;9',9a'1'-hi]xanthylium perchlorate

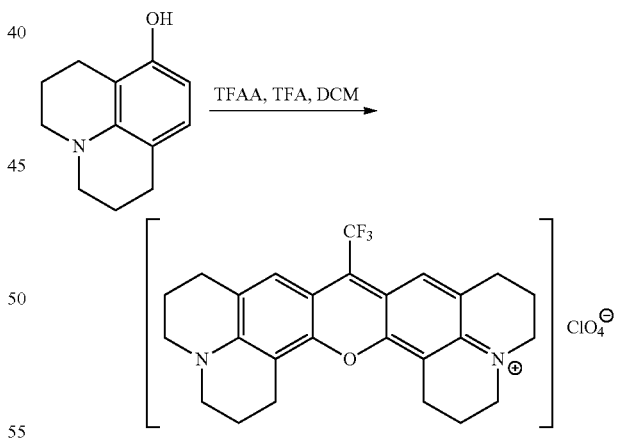

Method described in N. F. Haley, *Journal of Heterocyclic Chemistry* 1977, 14, 683.

8-(Trifluoromethyl)-2,3,5,6,11,12,14,15-octahydro-1H,4H,10H,13H-diquinolizino[9,9a,1-bc;9',9a'1'-hi]xanthylium perchlorate Trifluoroacetic acid (0.25 cm$^3$), 8-hydroxyjulolidine (1.00 g, 5.29 mmol) and trifluoroacetic anhydride (3.94 g, 21.1 mmol) were stirred together in dichloromethane (8 cm$^3$) under nitrogen at room temperature for 4 days. The solvent was removed under vacuum and remaining solid added to water (100 cm³). The resulting mixture was filtered and the solid washed with water (2×10 cm³). Perchloric acid (3 cm³) was added to the filtrate and the mixture left to stand at room temperature overnight. The precipitate was collected by filtration and dried. Column chromatography (1:9 methanol/dichloromethane) gave the target material as a purple solid (67 mg, 5%).

$\delta_H$ (250 MHz, CDCl₃): 7.52 (2H, s, CH), 3.60 (8H, t, $J_1$=6 Hz, CH₂), 2.97 (4H, $J_1$=6 Hz, CH₂), 2.88 (4H, t, $J_2$=7 Hz, CH₂), 2.07-2.03 (8H, m, CH₂); $\delta_c$ (100 MHz, CD₃OD): 152.2, 151.4, 125.9, 124.0, 123.9, 110.0, 106.2, 51.0, 50.4, 27.7, 20.6, 19.7, 19.5; $\nu_{max}$ (KBr)/cm⁻¹: 2926, 1598, 1500, 1317, 1297, 1265, 1150, 1109; m/z (ESI): 439.3 (100%, [M–ClO₄]⁺).

Synthesis 4

8-Ethyl-2,3,6,7,12,13,16,17-Octahydro-1H,5H,11H, 15H-diquinolizino[1,9-bc;1',9'-hi]xanthylium chloride

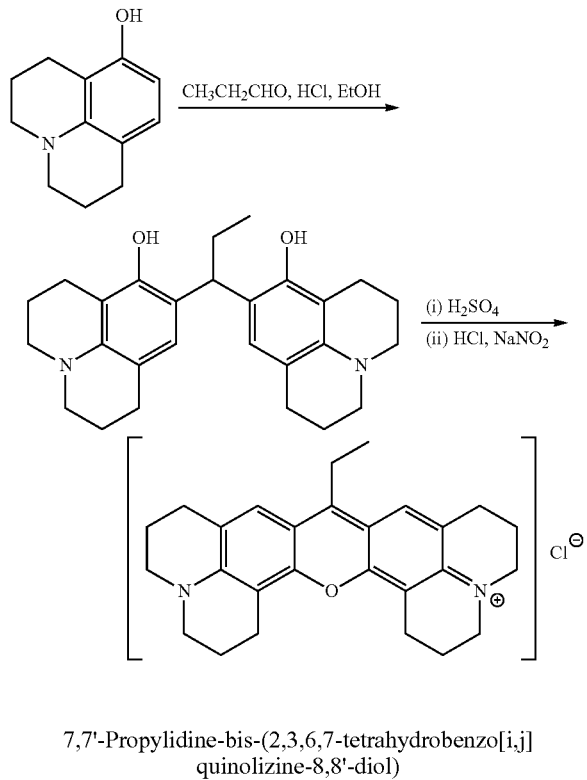

7,7'-Propylidine-bis-(2,3,6,7-tetrahydrobenzo[i,j]quinolizine-8,8'-diol)

8-Hydroxyjulolidine (5.00 g, 26.45 mmol) was dissolved in a solution of ethanol (50 cm³) and hydrochloric acid (1.3 cm³, 32%). Propionaldehyde (767 mg, 13.23 mmol) was added to the mixture and the reaction heated to 40° C. for 18 hours. An additional quantity of propionaldehyde (767 mg, 13.23 mmol) was added and the reaction heated for a further 24 hours. The resulting solution was cooled and poured into water (75 cm³). The mixture was neutralised with sodium bicarbonate (saturated solution) and extracted with dichloromethane (3×40 cm³). The combined extracts were dried over sodium sulphate and the solvent removed under reduced pressure. Column chromatography (3:7 ethyl acetate/hexane) gave the target material as a low melting colourless solid (2.76 g, 50%).

$\delta_H$ (250 MHz, CDCl₃): 6.69 (2H, s, CH), 5.57 (2H, s, OH), 3.83 (1H, t, $J_1$=6.5 Hz, CH), 3.02-3.00 (8H, m, CH₂), 2.68-2.65 (4H, m, CH₂), 2.60-2.55 (4H, m, CH₂), 2.02-1.91 (6H, m, CH₂), 0.88 (3H, t, $J_2$=7 Hz, CH₃); $\nu_{max}$ (KBr)/cm⁻¹: 3411, 2930, 1626, 1493, 1353, 1197.

8-Ethyl-2,3,6,7,12,13,16,17-Octahydro-1H,5H,11H, 15H-diquinolizino[1,9-bc;1',9'-hi]xanthylium chloride 7,7'-Propylidine-bis-(2,3,6,7-tetrahydrobenzo[i,j]quinolizine-8,8'-diol) (1.00 g, 2.39 mmol) was dissolved in concentrated sulphuric acid (4 cm³) and the resulting solution heated to 90° C. for 3 hours. The reaction was allowed to cool to room temperature prior to quenching with ice water (20 cm³). The mixture was neutralised with sodium hydroxide (40%) whilst maintaining a reaction temperature of 15° C. or below. Hydrochloric acid (2 cm³, 32%) was added and the mixture allowed to warm to room temperature. Sodium nitrite (330 mg, 4.78 mmol) in water (15 cm³) was added drop wise and the reaction stirred at room temperature for 16 hours. The resulting precipitate was collected by filtration and dried under vacuum overnight. Column chromatography (1:9 methanol/dichloromethane) gave the target material as a green solid (94 mg, 9%).

$\delta_H$ (250 MHz, CD₃OD): 7.64 (2H, s, CH), 3.53 (8H, t, $J_1$=5 Hz, CH₂), 3.00-2.89 (8H, m, CH₂), 2.03-2.01 (10H, m, CH₂), 1.34 (3H, t, $J_2$=7 Hz, CH₃); m/z (ESI): 399.3 (100%, [M–Cl]⁺).

Synthesis 5

3,6-Bis-Diethylamino Xanthylium Chloride

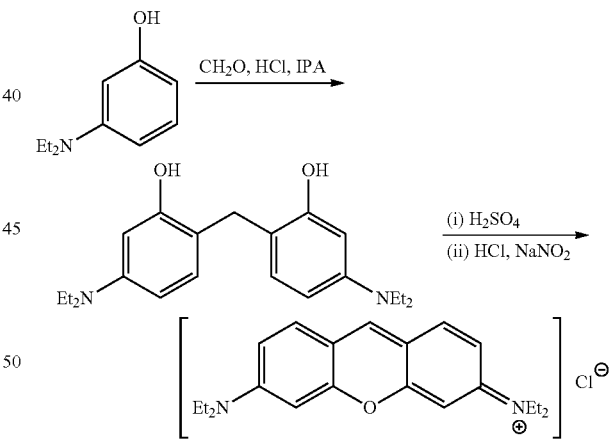

5,5'-Bis-diethylamino-2,2'-methandiyl-di-phenol

Adapted from J. Biehringer, *Journal Fur Praktische Chemie* 1896, 54, 235.

A suspension of 3-diethylaminophenol (200 g, 1.21 mmol) and isopropanol (600 cm³) was stirred in a 2 L jacketed reactor vessel. The jacket was maintained at 20° C. whilst concentrated hydrochloric acid (67 cm³, 32%) was added. The reaction was allowed to cool to 20° C. before formalin (47 cm³, 39% in water) was added drop wise over a 10 minute period. The resulting solution was stirred at 20° C. for 3.5 hour after which the reaction was judged complete by TLC

[R$_f$=0.4 (product) vs. 0.7 (starting material) (3:7 Ethyl acetate/Pet. Ether 40/60)]. A solution of ammonium bicarbonate (90.0 g) in water (800 cm$^3$) was prepared, and then added drop wise to the reaction over 35 minutes. The reaction was stirred for an additional 1 hours after which the resulting solid was filtered and washed with water (2×200 cm$^3$). The solid was dried at 60° C. overnight and then dissolved in isopropanol (250 cm$^3$) under reflux for 1 hour. The solution was cool to 5° C. over 90 minutes, and stirred at 5° C. for an additional 1 hour. The product was collected by filtration, washed with pre-chilled isopropanol (2×100 cm$^3$), and dried at 50° C. for 2 hours to give the target material as a light brown crystalline solid (141 g, 68%).

$\delta_H$ (250 MHz, CDCl$_3$): 7.03 (2H, d, J$_1$=8 Hz, CH), 6.20 (2H, dd, J$_1$=8 Hz, J$_2$=3 Hz, CH), 6.14 (2H, d, J$_2$=3 Hz, CH), 3.71 (2H, s, CH$_2$), 3.22 (8H, q, J$_3$=7 Hz, CH$_2$), 1.07 (12H, t, J$_3$=7 Hz, CH$_3$); $\delta_c$ (63 MHz, CDCl$_3$): 153.6, 147.7, 131.0, 116.2, 106.3, 100.9, 44.7, 29.8, 12.3; $\nu_{max}$ (KBr)/cm$^{-1}$: 3446, 3383, 2975, 2925, 1596, 1519, 1396, 1374, 1262, 1169, 1152; m/z (ESI): 343.3 (100%, [M+H]$^+$).

3,6-Bis-diethylamino xanthylium chloride

Adapted from J. Biehringer, *Journal Fur Praktische Chemie* 1896, 54, 217;
J. Biehringer, *Chemische Berichte* 1894, 27, 3299; and U.S. Pat. No. 3,932,415.

5,5'-Bis-diethylamino-2,2'-methandiyl-di-phenol (2.00 g, 5.85 mmol) was added portion-wise to a mixture of concentrated sulphuric acid (7.2 cm$^3$) and water (0.8 cm$^3$). The solution was heated to 140° C. for 2 hours under nitrogen. The solution was allowed to cool to 5° C. prior to the addition of ice water (10 cm$^3$). The pH of the solution was adjusted to pH 9 by the slow addition of sodium hydroxide (40%) whilst maintaining a temperature of 20° C. or below. Hydrochloric acid (3.5 cm$^3$, 32%) was added and the solution allowed to warm to room temperature. Sodium nitrite (807 mg, 11.7 mmol) dissolved in water (10 cm$^3$) was added drop wise. Once the addition was complete the reaction was stirred at room temperature for 16 h. The mixture was filtered and the solid dried under vacuum for 20 hours. The solid was extracted with methanol and the solvent removed under reduced pressure to give the product as a green solid (1.18 g, 56%).

Scaled-Up Procedure:

5,5'-Bis-diethylamino-2,2'-methandiyl-di-phenol (10.00 g, 29.24 mmol) was added portion-wise to a mixture of concentrated sulphuric acid (28.5 cm$^3$) and water (9.5 cm$^3$) pre-cooled to 5° C. The solution was heated to 140° C. for 2 hours under nitrogen. The solution was allowed to cool to 5° C. prior to the addition of ice water (50 cm$^3$). The pH of the solution was adjusted to pH 9 by the slow addition of sodium hydroxide (40%) whilst maintaining a temperature of 20° C. or below. Hydrochloric acid (17.5 cm$^3$, 32%) was added and the solution allowed to warm to room temperature. Sodium nitrite (4.03 mg, 58.48 mmol) dissolved in water (25 cm$^3$) was added dropwise. Once the addition was complete the reaction was stirred at room temperature for 2 h. The mixture was filtered and the solid dried under vacuum. The solid was extracted with methanol (60 cm$^3$) and the solvent removed under reduced pressure to give the product as a green solid (5.78 g, 55%).

$\delta_H$ (250 MHz, CD$_3$OD): 8.51 (1H, s, CH), 7.76 (2H, d, J$_1$=9 Hz, CH), 7.13 (2H, dd, J$_1$=9 Hz, J$_2$=3 Hz, CH), 6.88 (2H, d, J$_2$=3 Hz, CH), 3.68 (8H, q, J$_3$=7 Hz, CH$_2$), 1.31 (12H, t, J$_3$=7 Hz, CH$_3$); $\delta_c$ (100 MHz, DMSO-d$_6$): 158.2, 156.2, 146.3, 134.2, 114.9, 114.3, 96.4, 46.0, 13.1; $\nu_{max}$ (KBr)/cm$^{-1}$: 2975, 2925, 1596, 1579, 1519, 1347, 1169, 1132, 1076; m/z (ESI): 323.3 (100%, [M–Cl]$^+$).

Synthesis 6

3,6-Bis-diethylamino xanthylium bromide

3,6-Bis-diethylamino xanthylium bromide

Method A

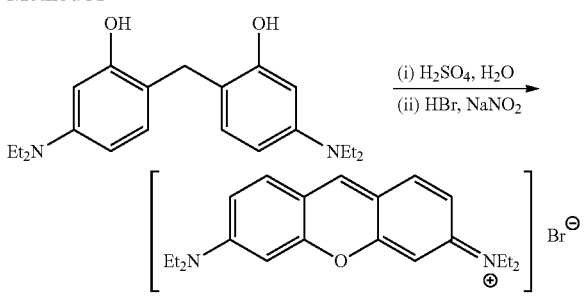

5,5'-Bis-diethylamino-2,2'-methandiyl-di-phenol (5.00 g, 14.62 mmol) was added portion-wise to a mixture of concentrated sulphuric acid (15 cm$^3$) and water (5 cm$^3$). The solution was heated to 160° C. for 2 hours under nitrogen. The solution was allowed to cool to 5° C. prior to the addition of ice water (25 cm$^3$). The pH of the solution was adjusted to pH 9 by the slow addition of sodium hydroxide (40%) whilst maintaining a temperature of 20° C. or below. Hydrobromic acid (8 cm$^3$, 48%) was added drop wise and the solution allowed to warm to room temperature. Sodium nitrite (2.02 mg, 29.24 mmol) dissolved in water (25 cm$^3$) was added drop wise. Once the addition was complete the reaction was stirred at room temperature for 18 hours. The resulting precipitate was collected by filtration and dried under vacuum to give the product as a green/brown solid (2.51 g, 43%).

Method B

Concentrated sulphuric acid (10.8 cm$^3$) was added to water (1.2 cm$^3$) and the mixture cooled to 5° C. in ice. 5,5'-Bis-diethylamino-2,2'-methandiyl-di-phenol (4.00 g, 11.70 mmol) was added portion wise with stirring. The mixture was then heated at 110° C. for 22 hours under nitrogen. The resulting dark orange solution was cooled in ice to 5° C. before the addition of ice water (20 cm$^3$). The mixture was neutralised by the slow addition of sodium hydroxide (40% in water) whilst maintaining a temperature of 20° C. or below. Hydrochloric acid (12 cm$^3$, 32%) was added drop wise and the mixture stirred at room temperature for 30 minutes. Iron (III) chloride (12.64 g, 46.78 mmol) in water (12 cm$^3$) was added and the mixture heated to 90° C. for 4 hours. The solution was allowed to cool to room temperature over 3 hours. The resulting green precipitate was collected by filtration. The solid was dissolved in water (60 cm³). Nitric acid (3 cm³, 70%) was added and the mixture stirred at room temperature for 30 minutes. The resulting solid was collected by filtration and dried under vacuum overnight. The solid was dissolved in water (40 cm³) and KBr (4.00 g, 33.61 mmol) was added and the mixture heated to 60° C. for 30 minutes. The mixture was allowed to cool to room temperature over 3 hours. The resulting solid was collected by filtration and dried under vacuum overnight to give the product as a green crystalline solid (3.52 g, 74%).

Method C

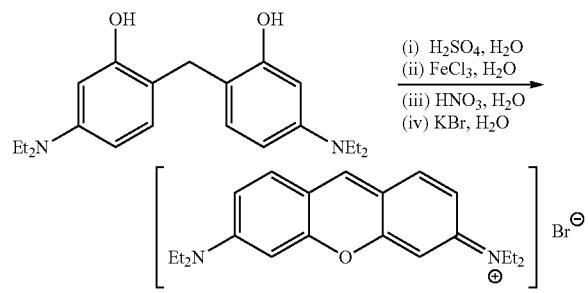

Concentrated sulphuric acid (162 cm³) was added to water (18 cm³) and the mixture cooled to 5° C. in ice. 5,5'-Bis-diethylamino-2,2'-methandiyl-di-phenol (60.00 g, 0.175 mol) was added portion wise with stirring. The mixture was then heated at 110° C. for 22 hours under argon. The resulting dark orange solution was cooled in ice to 5° C. before the addition of ice water (300 cm³). Iron (III) chloride (94.74 g, 0.351 mol) in water (240 cm³) was added and the mixture heated to 90° C. for 22 hours in air. The solution was allowed to cool to room temperature over 3 hours. The resulting green precipitate was collected by filtration. The solid was dissolved in water (90 cm³). Nitric acid (50 cm³, 70%) was added and the mixture stirred at room temperature for 30 minutes. The resulting solid was collected by filtration and dried under vacuum overnight. The solid was dissolved in water (170 cm³) and KBr (38.00 g, 0.319 mol) was added and the mixture heated to 60° C. for 30 minutes. The mixture was allowed to cool to room temperature over 3 hours. The resulting solid was collected by filtration and dried under vacuum overnight to give the product as a green crystalline solid (34.34 g, 48%).

$\delta_H$ (250 MHz, DMSO-$d_6$): 8.74 (1H, s, CH), 7.85 (2H, d, $J_1$=9 Hz, CH), 7.19 (2H, d, J=9 Hz, CH), 6.88 (2H, s, CH), 3.65 (8H, q, $J_2$=6 Hz, CH), 1.20 (12H, t, $J_2$=6 Hz, $CH_3$); $\delta_c$ (100 MHz, DMSO-$d_6$): 158.1, 156.2, 146.2, 134.2, 114.9, 114.3, 96.4, 46.0, 19.1; $\nu_{max}$ (KBr)/cm$^{-1}$: 2970, 1650, 1594, 1520, 1489, 1428, 1396, 1346, 1265, 1168, 1073, 1006, 968; m/z (ESI): 323.2 (100%, [M−Br]$^+$).

Synthesis 7

3,6-Bis-diethylamino xanthylium iron tetrachloride 3,6-Bis-diethylamino xanthylium iron tetrachloride Method A

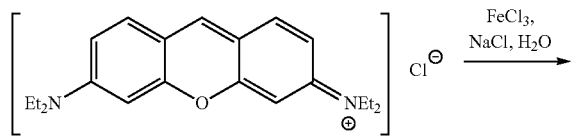

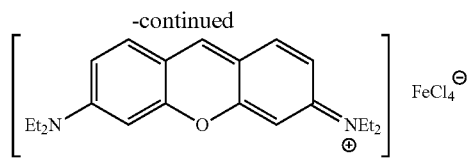

3,6-Bis-diethylamino xanthylium chloride (40 mg, 0.111 mmol), was dissolved in water (5 cm³). Iron (III) chloride (30 mg, 0.111 mmol) was added and the solution was allowed to stand at room temperature for 2 hours. Sodium chloride was added until a green precipitate was observed. This was collected by filtration and dried under vacuum overnight (53 mg, 91%).

Modified Method:

3,6-Bis-diethylamino xanthylium chloride (100 mg, 0.279 mmol), was dissolved in water (15 cm³). Iron (III) chloride (75 mg, 0.279 mmol) was added and the solution was allowed to stand at room temperature for 30 minutes. Sodium chloride was added until a green precipitate was observed. This was collected by filtration and dried under vacuum overnight (141 mg, 97%).

Method B

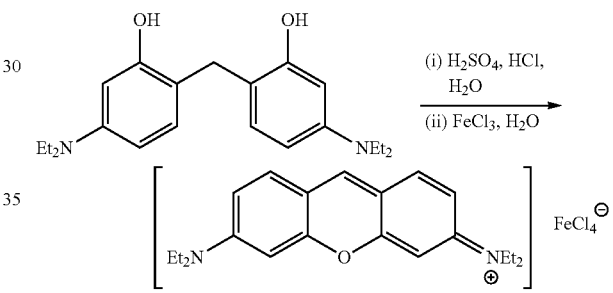

Concentrated sulphuric acid (27 cm³) was added to water (3 cm³) and the mixture cooled to 5° C. in ice. 5,5'-Bis-diethylamino-2,2'-methandiyl-di-phenol (10.00 g, 29.24 mmol) was added portion wise with stirring. The mixture was then heated at 140° C. for 90 minutes under nitrogen. The resulting dark orange solution was cooled in ice to 5° C. before the addition of ice water (60 cm³). The mixture was neutralised by the slow addition of sodium hydroxide (40% in water) whilst maintaining a temperature of 20° C. or below. Hydrochloric acid (10 cm³, 32%) was added drop wise and the mixture stirred at room temperature for 30 minutes. The mixture was filtered and the solid sodium sulphate washed with water (3×50 cm³). Iron (III) chloride (15.79 g, 58.47 mmol) in water (50 cm³) was added to the filtrate and the mixture heated to 90° C. for 2 hours. The solution was allowed to cool to room temperature and concentrated hydrochloric acid was added slowly until precipitation of the product occurred (pH~1). The mixture was filtered and the solid dried under vacuum overnight to give the product as a green solid (11.43 g, (5%).

$\delta_H$ (250 MHz, DMSO-$d_6$): 8.76 (1H, s, CH), 7.85 (2H, d, $J_1$=9 Hz, CH), 7.16 (2H, dd, $J_1$=9 Hz, $J_2$=3 Hz, CH), 6.86 (2H, d, $J_2$=3 Hz, CH), 3.64 (8H, q, $J_3$=7 Hz, $CH_2$), 1.27 (12H, t, $J_3$=7 Hz, $CH_3$); $\nu_{max}$ (KBr)/cm$^{-1}$: 2970, 2926, 1585, 1495, 1396, 1343, 1252, 1074; m/z (ESI): 323.2 (100%, [M−FeCl$_4$]$^+$).

Synthesis 8

3,6-Bis-diethylamino xanthene dihydrochloride

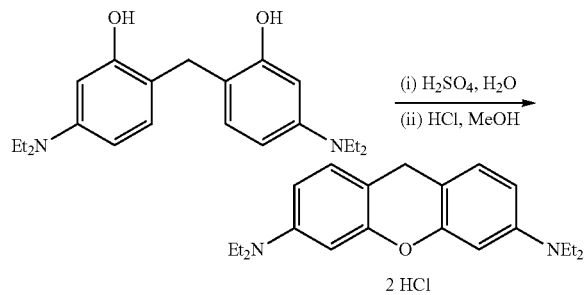

3,6-Bis-diethylamino xanthene dihydrochloride

Concentrated sulphuric acid (6 cm$^3$) was added to water (2 cm$^3$) and the mixture cooled to 5° C. in ice. 5,5'-Bis-diethylamino-2,2'-methandiyl-di-phenol (2.00 g, 5.85 mmol) was added portion wise with stirring. The mixture was then heated at 160° C. for 2 hours under nitrogen. The resulting dark orange solution was cooled in ice to 5° C. before the addition of ice water (10 cm$^3$). The mixture was neutralised by the slow addition of sodium hydroxide (40% in water) keeping the temperature below 20° C. The resulting precipitate was collected by filtration, washed with water (2×10 cm$^3$) and dried under vacuum overnight. The intermediate was added to a solution of methanol (20 cm$^3$) and hydrochloric acid (1.3 cm$^3$, 32%) and stirred for 1 hour until homogeneous. The solvent was removed under reduced pressure and the solid dried under vacuum overnight to give the product as a purple solid (1.03 g, 44%).

$\delta_H$ (250 MHz, D$_2$O): 7.49 (2H, d, J$_1$=8 Hz, CH), 7.26-7.21 (4H, m, CH), 4.16 (2H, s, CH$_2$), 3.63 (8H, q, J$_3$=7 Hz, CH$_2$), 1.12 (12H, t, J$_3$=7 Hz, CH$_3$); $\nu_{max}$ (KBr)/cm$^{-1}$: 2980, 2614, 1612, 1479, 1414, 1344, 1290, 1153, 1106, 1015; m/z (ESI): 325.3 (41%, [M−HCl$_2$]$^+$).

Synthesis 9

3,6-Bis-diethylamino Xanthylium Nitrate 3,6-Bis-diethylamino Xanthylium Nitrate Method A

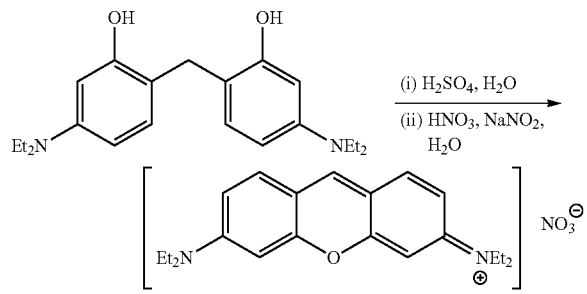

Concentrated sulphuric acid (5.4 cm$^3$) was added to water (0.6 cm$^3$) and the mixture cooled to 5° C. in ice. 5,5'-Bis-diethylamino-2,2'-methandiyl-di-phenol (2.00 g, 5.85 mmol) was added portion wise with stirring. The mixture was then heated to 140° C. for 90 minutes under nitrogen. The resulting dark orange solution was cooled in ice to 5° C. before the addition of ice water (12 cm$^3$). The mixture was neutralised by the slow addition of sodium hydroxide (40% in water) whilst maintaining a temperature of 20° C. or below. Nitric acid (1 cm$^3$, 70%) was added drop wise and the mixture stirred at room temperature for 30 minutes. The mixture was filtered and the solid sodium sulphate washed with water (3×10 cm$^3$). Nitric acid (1 cm$^3$, 70%) was added to the filtrate followed by the drop wise addition of sodium nitrite (807 mg, 11.70 mmol) in water (10 cm$^3$). The reaction was stirred at room temperature for 15 minutes, whereupon the resulting solid was collected by filtration and dried under vacuum overnight to give the product as a purple/green solid (643 mg, 29%).

$\delta_H$ (250 MHz, DMSO-d$_6$): 8.55 (1H, s, CH), 7.79 (2H, d, J$_1$=9 Hz, CH), 7.17 (2H, dd, J$_1$=9 Hz, J$_2$=2 Hz, CH), 6.93 (2H, d, J$_2$=2 Hz, CH), 3.69 (8H, q, J$_3$=7 Hz, CH$_2$), 1.32 (12H, t, J$_3$=7 Hz, CH$_3$); $\delta_C$ (100 MHz, DMSO-d$_6$): 158.2, 156.2, 146.3, 134.2, 114.9, 96.4, 45.0, 13.1; $\nu_{max}$ (KBr)/cm$^{-1}$: 2978, 1596, 1522, 1493, 1387, 1347, 1264, 1168, 1074, 1007; m/z (ESI): 323.2 (100%, [M−NO$_3$]$^+$).

3,6-Bis-diethylamino xanthylium nitrate.HNO$_3$

Method B

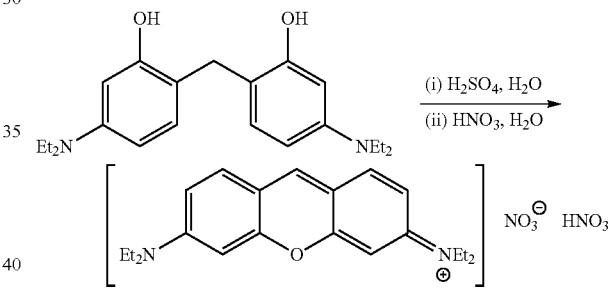

Concentrated sulphuric acid (5.4 cm$^3$) was added to water (0.6 cm$^3$) and the mixture cooled to 5° C. in ice. 5,5'-Bis-diethylamino-2,2'-methandiyl-di-phenol (2.00 g, 5.85 mmol) was added portion wise with stirring. The mixture was then heated at 140° C. for 90 minutes under nitrogen. The resulting dark orange solution was cooled in ice to 5° C. before the addition of ice water (12 cm$^3$). The mixture was neutralised by the slow addition of sodium hydroxide (40% in water) whilst maintaining a temperature of 20° C. or below. Nitric acid (6 cm$^3$, 70%) was added drop wise and the mixture stirred at room temperature for 30 minutes until the precipitate completely dissolved. The reaction was heated to 100° C. for 24 hours and then cooled to room temperature. Nitric acid (0.5 cm$^3$, 70%) was added and the resulting solid collected by filtration.

The crude product was dissolved in fresh water (20 cm$^3$) and nitric acid (few drops, 70%) added until product began to precipitate. The mixture was then heated to 60° C. for 30 minutes before cooling to room temperature over 4 hours. The mixture was then filtered and the precipitate dried under vacuum overnight to give the product as a green/purple solid (467 mg, 21%).

Alternatively, the crude product was dissolved in fresh water (20 cm$^3$) and nitric acid (few drops, 70%) added until the product precipitated. The mixture was then filtered and the precipitate dried under vacuum overnight. Material was dissolved in the minimum volume of hot IPA, cooled to 5° C. overnight, and the solid collected by filtration and dried under vacuum to give the product as a green/purple solid (401 mg, 18%).

3,6-Bis-diethylamino Xanthylium Nitrate.HNO$_3$

Method C

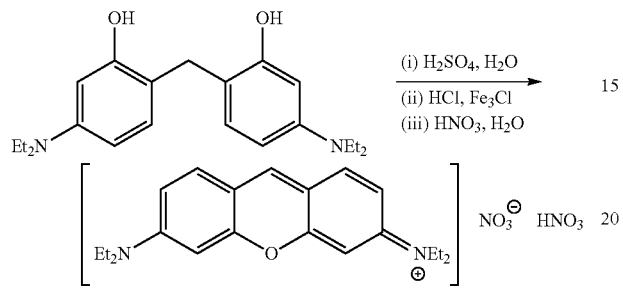

3,6-Bis-diethylamino xanthylium iron tetrachloride (11.00 g, 21.11 mmol) was dissolved in water (40 cm$^3$). Nitric acid (2 cm$^3$, 70%) was added and the mixture stirred at room temperature for 30 minutes. The resulting solid was collected by filtration and dried under vacuum overnight to give the product as a purple solid (7.11 g, 54%).

$\delta_H$ (250 MHz, DMSO-d$_6$): 8.73 (1H, s, CH), 7.86 (2H, d, J=9 Hz, CH), 7.21 (2H, d, J=9 Hz, CH), 6.90 (2H, s, CH), 3.72-3.55 (8H, m, CH$_2$), 1.21 (12H, t, J=7 Hz, CH$_3$).

Method C described above involves the preparation of an intermediate having an iron tetrachloride counter ion. Nitric acid may be used to replace that counter ion. Excessive levels of iron are generally unacceptable in pharmaceutical products. Table 1 below shows the metal levels within a product obtained by Method C (Pyronin B NO$_3^-$.HNO$_3$) in comparison with the intermediate iron tetrachloride salt (Pyronin FeCl$_4^-$).

TABLE 1

Metal levels in the product of Method C

| Sample Metals (µg/g) | Pyronin FeCl$_4^-$ | Pyronin B NO$_3^-$•HNO$_3$ |
|---|---|---|
| B | 31.5 | 1.7 |
| Mg | 3.6 | 2.3* |
| Al | 12 | 1.8* |
| V | 3.7 | 0.2 |
| Cr | 2.7 | 0.3 |
| Mn | 23.3 | 1.2 |
| Fe | 78982 | 126.8 |
| Co | 0.3 | <0.04 |
| Ni | 1.8 | 0.5 |
| Cu | 12.9 | <1.01 |
| Zn | 62.6 | 11.5 |
| Ga | 5.0 | <0.01 |
| Sb | 0.1 | <0.04 |
| Sn | 10.4 | 0.8 |
| Ba | 1.7 | 1.9 |
| Pb | 0.4 | <0.1 |
| Hg | 54 | 24 |
| Nb | Present | Absent |
| Ta | Present | Absent |
| Ge | Present | Absent |

*indicates an inhomogeneity between samples.

Synthesis 10

9-Ethyl-3,6-bis-diethylamino Xanthylium Chloride

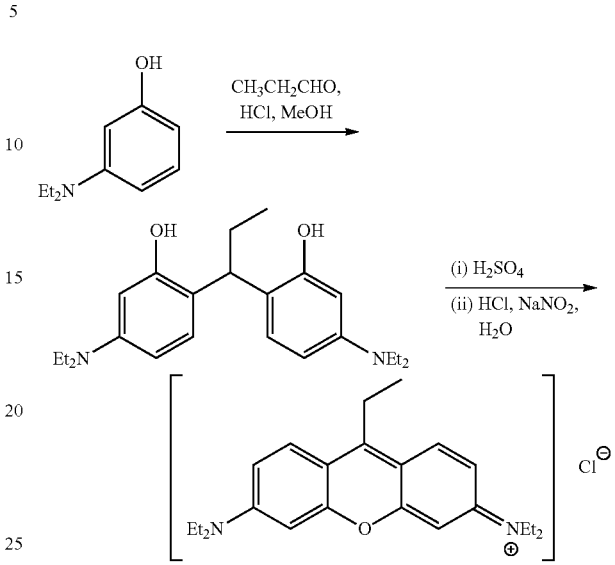

5,5'-Bis-diethylamino-2,2'-propylidine-di-phenol

3-Diethylaminophenol (10.00 g, 60.61 mmol) was dissolved in methanol (15 cm$^3$). The solution was cooled to 5° C. before hydrochloric acid (3 cm$^3$, 32%) was added. Propionaldehyde (1.76 g, 30.30 mmol) was then added drop wise and the resulting solution was heated to 40° C. overnight. A second portion of propionaldehyde (1.76 g, 30.30 mmol) was added and the mixture heated for a further 24 hours. The mixture was poured into water (30 cm$^3$) before the pH was adjusted to pH 8 with a saturated solution of ammonium bicarbonate. The mixture was extracted with dichloromethane (3×20 cm$^3$). The combined organic extracts were dried (sodium sulphate), filtered and the solvent removed under reduced pressure. Column chromatography (3:7 ethyl acetate/hexane) gave the target material as a pink solid (2.11 g, 19%).

$\delta_H$ (250 MHz, CDCl$_3$): 7.05 (2H, d, J$_1$=8.5 Hz, CH), 6.23 (2H, dd, J$_1$=8.5 Hz, J$_2$=2.5 Hz, CH), 6.09 (2H, d, J$_2$=2.5 Hz, CH), 3.96 (1H, t, J$_3$=7 Hz, CH), 3.23 (8H, q, J$_4$=7 Hz, CH$_2$), 2.06-2.00 (2H, m, CH$_2$), 1.08 (12H, t, J$_4$=7 Hz, CH$_3$), 0.90 (3H, t, J$_3$=7 Hz, CH$_3$); $\delta_C$ (62.5 MHz, CDCl$_3$): 153.8, 147.4, 127.5, 118.5, 105.8, 99.9, 44.3, 36.6, 26.3, 12.8, 12.5; $v_{max}$ (KBr)/cm$^{-1}$: 2967, 2899, 1620, 1517, 1354, 1210, 1091, 1076; m/z (ESI+): 371.3 (100%, [M+H]$^+$).

9-Ethyl-3,6-Bis-diethylamino Xanthylium Chloride

Adapted from U.S. Pat. No. 3,932,415

5,5'-Bis-diethylamino-2,2'-propylidine-di-phenol (500 mg, 1.35 mmol) was added portion-wise to concentrated sulphuric acid (2 cm$^3$). The solution was heated to 90° C. for 3 hours. The solution was allowed to cool to room temperature and then poured into ice water (20 cm$^3$). The pH of the solution was adjusted to pH 6 by the slow addition of sodium hydroxide (40% in water). Hydrochloric acid (1 cm$^3$, 32%) was added and the solution allowed to warm to room temperature. Sodium nitrite (186 mg, 2.70 mmol) dissolved in water (10 cm$^3$) was added drop wise. Once the addition was complete the reaction was stirred at room temperature for 16 hours. The resulting precipitate was collected by filtration and dried under vacuum. The solid was extracted with methanol/dichloromethane (1:20, 3×10 cm³). The solvent was removed under vacuum to give a green solid. This was then dissolved in water (10 cm³), filtered and the solid residue washed with water (2×5 cm³). The aqueous solution was saturated with sodium chloride before it was extracted with chloroform (7×30 cm³). The combined organic extracts were dried (sodium sulphate), filtered and the solvent removed under reduced pressure to give the product as a green solid (59 mg, 11%).

$\delta_H$(250 MHz, CD$_3$OD): 8.11 (2H, d, J$_1$=8 Hz, CH), 7.17 (2H, dd, J$_1$=8 Hz, J$_2$=3 Hz, CH), 6.89 (2H, d, J$_2$=3 Hz, CH), 3.65 (8H, J$_3$=7 Hz, CH$_2$), 3.45-3.38 (2H, m, CH$_2$), 1.40-1.20 (15H, m, CH$_3$); $v_{max}$ (KBr)/cm$^{-1}$: 2972, 1592, 1469, 1398, 1343, 1248, 1185, 1132, 1073; m/z (ESI): 351.2 (100%, [M−Cl]$^+$).

Synthesis 11

3,6-Bis(diethylamino))thioxanthylium Iodide

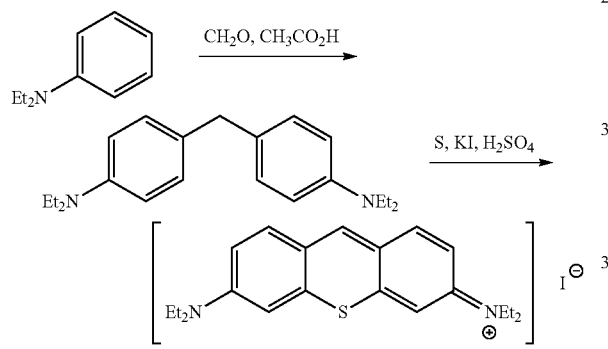

4,4'-Bis(diethylamino)diphenylmethane

Acetic acid (8.05 g, 0.134 mol) was added drop wise to N,N-diethylaniline (10.0 g, 67.1 mmol). Formalin (3.00 cm³, 37% in water) was added with stirring and the mixture heated to reflux for 90 minutes. The reaction was allowed to cool, before dilution with ice water (50 cm³). The reaction was basified with saturated sodium bicarbonate (pH 9). The resulting mixture was extracted with DCM (3×50 cm³), the combined extracts were dried over sodium sulphate, filtered and the solvent removed under reduced pressure. Column chromatography (1:9 ethyl acetate/hexane, R$_f$ 0.3) gave the target material as a colourless oil (10.01 g, 96%).

$\delta_H$ (250 MHz, CDCl$_3$): 7.02 (4H, d, J=8.5 Hz, CH), 6.61 (4H, d, J=8.5 Hz, CH), 3.77 (2H, s, CH$_2$), 3.30 (8H, q, J=7 Hz, CH$_2$), 1.21 (12H, t, J=7 Hz, CH$_3$); $\delta_c$ (63 MHz, CDCl$_3$): 146.1, 129.9, 129.6, 129.2, 112.2, 44.5, 39.8, 12.7; $v_{max}$ (neat)/cm$^{-1}$: 2969, 2928, 1614, 1564, 1517, 1465, 1354, 1264, 1195, 1151, 1075, 1012; m/z (ESI): 311.3 (100%, [M+H]$^+$).

3,6-Bis(diethylamino)thioxanthylium Iodide

Adapted from R. H. Nealey, J. S. Driscoll, *J. Hetero. Chem.* 1966, 3, 228.

Sulphur (1.65 g, 51.6 mmol) was added in small portions with vigorous stirring to fuming sulphuric acid (8.00 g) over a 15 minute period. The reaction was cooled to 5° C. and 4,4'-bis(diethylamino)diphenylmethane (2.00 g, 6.45 mmol) was added at such a rate to maintain the temperature below 20° C. The reaction was then stirred at ambient temperature for 90 minutes and then poured into 40 cm³ of ice. The resulting red mixture was boiled for 1 hour and then allowed to cool to ambient temperature before filtration.

Potassium iodide was added to the filtrate until a precipitate was observed. The mixture was cooled in ice before the green solid was collected by filtration and dried under reduced pressure (253 mg, 8%).

$\delta_H$ (250 MHz, DMSO-d$_6$): 8.62 (1H, s, CH), 7.98 (2H, d, J=9 Hz, CH), 7.36 (2H, d, J=3 Hz, CH), 7.23 (2H, dd, J=9 Hz, 3 Hz, CH), 3.68, (8H, q, J=7 Hz, CH$_2$), 1.23 (12H, t, J=7 Hz, CH$_3$); $v_{max}$ (KBr)/cm$^{-1}$: 3456, 3393, 1593, 1560, 1509, 1392, 1343, 1191, 1152, 1071; m/z (ESI): 339.4 (100%, [M−I]$^+$).

Synthesis 12

3,6-Bis(dimethylamino)thioxanthylium Zinc Trichloride

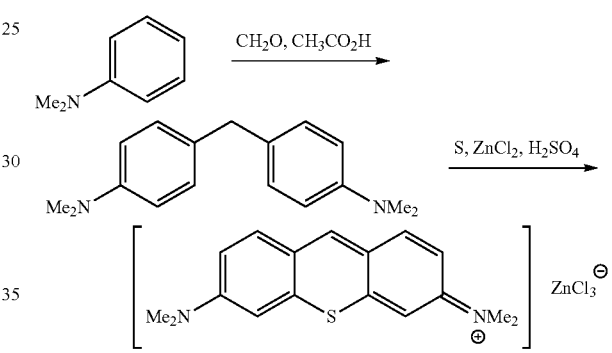

4,4'-Bis(dimethylamino)diphenylmethane

Acetic acid (9.91 g, 0.165 mol) was added drop wise to N,N-dimethylaniline (10.00 g, 82.6 mmol). Paraformaldehyde (1.23 g, 41.3 mmol) was added with stirring and the mixture heated to reflux for 90 minutes. The reaction was allowed to cool, before dilution with ice water (50 cm³). The reaction was basified with 10% sodium hydroxide (pH 9) and the resulting solid collected by filtration. The solid was washed with water (2×5 cm³), and dried. Recrystallisation from ethanol gave the target material as a colourless solid (6.54 g, 63%).

$\delta_H$ (250 MHz, CDCl$_3$): 7.05 (4H, d, J=8.5 Hz, CH), 6.68 (4H, d, J=8.5 Hz, CH), 3.80 (2H, s, CH$_2$), 2.62 (12H, s, CH$_3$); $\delta_c$ (62.5 MHz, CDCl$_3$): 149.1, 130.4, 129.5, 113.1, 41.0, 39.9; $v_{max}$ (KBr)/cm$^{-1}$: 2886, 2797, 1615, 1499, 1361, 1230, 1070, 828, 796;

m/z (ESI): 253.2 (100%, [M−H]$^+$).

3,6-Bis(dimethylamino)thioxanthylium Zinc Trichloride

From R. H. Nealey, J. S. Driscoll, *J. Hetero. Chem.* 1966, 3, 228.

Sulphur (10.0 g, 0.33 mol) was added in small portions with vigorous stirring to fuming sulphuric acid (50 g) over a 15 minute period. The reaction was cooled to 5° C. and 4,4'-bis(dimethylamino)diphenylmethane (10.00 g, 39.4 mmol) was added at such a rate to maintain the temperature below 20° C. The reaction was then stirred at ambient temperature for 90 minutes and then poured into 250 cm³ of ice. The resulting red mixture was boiled for 1 hour and then allowed to cool to ambient temperature before filtration. A 40% aqueous solution of zinc chloride was added to the filtrate until a green colour was observed. The mixture was cooled in an ice bath and the solid collected by filtration. The solid was dried overnight under reduced pressure to give the target material as a green solid (1.81 g, 10%).

$\delta_H$ (250 MHz, DMSO-d$_6$): 8.68 (1H, s, CH), 8.01 (2H, d, J=9 Hz, CH), 7.37 (2H, d, J=3 Hz, CH), 7.25 (2H, dd, J=9 Hz, 3 Hz, CH), 3.28 (12H, s, CH$_3$); $\delta_c$ (62.5 MHz, DMSO-d$_6$): 154.5, 149.3, 143.6, 138.1, 119.0, 116.2, 106.4, 41.0; $\nu_{max}$ (KBr)/cm$^{-1}$: 3755, 3381, 1614, 1599, 1527, 1395, 1179, 1073; m/z (ESI): 283.2 (100%, [M−ZnCl$_3$]$^+$).

Synthesis 13

3,6-Bis(dimethylamino)-1,9-dimethylthioxanthylium Zinc Trichloride

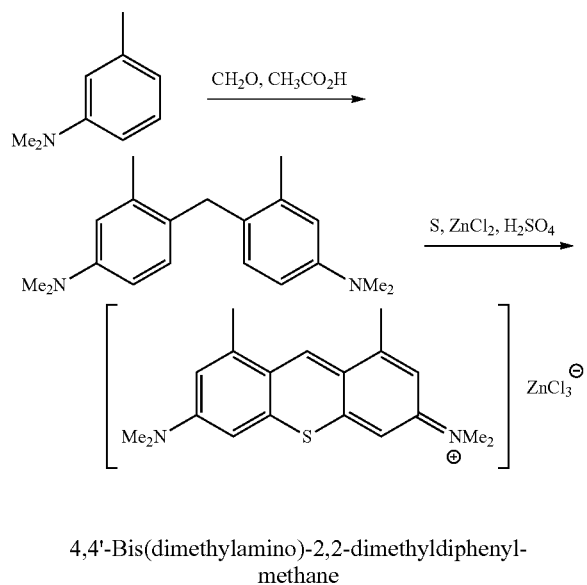

4,4'-Bis(dimethylamino)-2,2-dimethyldiphenyl-methane

Hydrochloric acid (1.5 cm³, 10 M) was added drop wise to a solution of 3-N,N-trimethylaniline (5.00 g, 37.0 mmol) in methanol (10 cm³) cooled to 5° C. Formalin (1.50 cm³, 40% in water) was added and the reaction allowed to stand at 6° C. for 48 hours. The resulting colourless crystals were collected by filtration, washed with cold methanol (5 cm³) and dried under reduced pressure (4.13 g, 79%).

$\delta_H$ (250 MHz, CDCl$_3$): 6.77 (2H, d, J=8.5 Hz, CH), 6.64 (2H, d, J=3 Hz, CH), 6.54 (2H, dd, J=8.5, 3 Hz, CH), 3.75 (2H, s, CH$_2$), 2.91 (12H, s, CH$_3$), 2.24 (6H, s CH$_3$);

$\delta_c$ (62.5 MHz, CDCl$_3$): 149.2, 137.1, 129.9, 127.7, 114.9, 110.7, 41.0, 34.9, 20.2; $\nu_{max}$ (KBr)/cm$^{-1}$: 3341, 3328, 1613, 1507, 1344, 1330, 1226, 1059, 1010, 841, 799; m/z (ESI): 283.2 (100%, [M+H]$^+$).

3,6-Bis(dimethylamino)-1,9-dimethylthioxanthylium zinc trichloride

Adapted from R. H. Nealey, J. S. Driscoll, *J. Hetero. Chem.* 1966, 3, 228.

Sulphur (907 mg, 28.4 mmol) was added in small portions with vigorous stirring to fuming sulphuric acid (5.0 cm³) over a 15 minute period. The reaction was cooled to 5° C. and 4,4'-bis(dimethylamino)-2,2-dimethyldiphenylmethane (1.00 g, 3.55 mmol) was added at such a rate to maintain the temperature below 20° C. The reaction was then stirred at ambient temperature for 90 minutes and then poured into 30 cm³ of ice. The resulting red mixture was boiled for 1 hour and then allowed to cool to ambient temperature before filtration. A 40% aqueous solution of zinc chloride was added to the filtrate until a green colour was observed. The mixture was cooled in an ice bath and the solid collected by filtration. This precipitation was repeated and the resulting solid was dried overnight under reduced pressure to give the target material as a green solid (98 mg, 6%).

$\delta_H$ (250 MHz, DMSO-d$_6$): 8.58 (1H, s, CH), 7.19 (2H, s, CH), 7.17 (2H, s, CH), 3.24 (12H, s, CH$_3$), 2.84 (6H, s, CH$_3$); $\delta_c$ (62.5 MHz, DMSO-d$_6$): 154.1, 145.7, 144.2, 141.6, 118.1, 116.7, 104.6, 40.9, 20.2; m/z (ESI): 311.2 (100%, [M−ZnCl$_3$]$^+$).

Synthesis 14

3,7-Bis(dimethylamino)phenazinium chloride

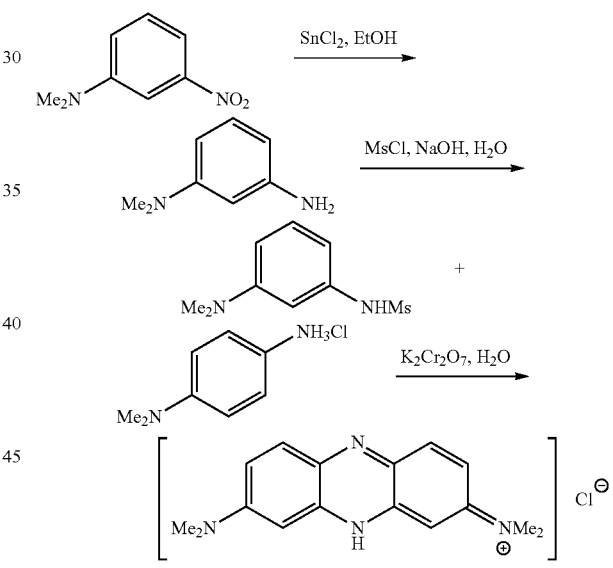

N,N-dimethyl-1,3-phenylenediamine

N,N-dimethyl-3-nitroaniline (3.00 g, 18.1 mmol) was dissolved in ethanol (40 cm³). Tin dichloride (16.3 g, 72.0 mmol) was added and the reaction heated under reflux for 16 h. The reaction mixture was allowed to cool before the bulk of the solvent was removed under reduced pressure. The remaining residue was poured in to water (100 cm³), and basified with sodium hydroxide (3M). The mixture was extracted with chloroform (3×30 cm³). The combined extracts were dried over sodium sulphate, filtered and the solvent removed under reduced pressure to give the product as a brown oil (2.01 g, 82%).

$\delta_H$ (250 MHz, CDCl$_3$): 7.02 (1H, t, J=8 Hz, CH), 6.23 (1H, dd, J=6 Hz, J=3 Hz, CH), 6.12 (1H, d, J=3 Hz, CH), 6.09 (1H, s, CH), 2.94 (6H, s, CH$_3$); $\delta_c$ (62.5 MHz, CDCl$_3$): 151.8, 147.4, 129.9, 104.3, 103.8, 99.6, 40.7; $v_{max}$ (neat)/cm$^{-1}$: 2879, 2800, 1611, 1504, 1443, 1354, 1260, 1174, 994.

N-[3-(dimethylamino)phenyl]methanesulphonamide

Methanesulphonyl chloride (838 mg, 7.35 mmol) was added slowly to a cooled solution (5° C.) of N,N-dimethyl-1,3-phenylenediamine (1.00 g, 7.35 mmol) and sodium hydroxide (5M, 1.5 cm$^3$) in water (10 cm$^3$). The reaction was allowed to warm to room temperature overnight. The mixture was extracted with chloroform (3×15 cm$^3$). The combined extracts were dried over sodium sulphate, filtered and the solvent removed under reduced pressure. Column chromatography (1:20 methanol/dichloromethane) gave the target material as a brown oil (1.24 g, 79%).

$\delta_H$ (250 MHz, CDCl$_3$): 7.20 (1H, t, J=8 Hz, CH), 6.55-6.47 (3H, m, CH), 3.00 (3H, s, CH$_3$), 2.95 (6H, s, CH$_3$); $\delta_c$ (62.5 MHz, CDCl$_3$): 151.6, 137.8, 130.1, 109.5, 108.5, 104.6, 40.8, 38.7; $v_{max}$ (neat)/cm$^{-1}$: 2929, 2806, 1607, 1511, 1394, 1321, 1231, 1148, 1004, 940;

3,7-Bis(dimethylamino)phenazinium chloride

Adapted from D. F. Gloster, L. Cincotta, J. W. Foley, *J. Heterocyclic Chem.* 1999, 36, 25.

N,N-dimethyl-1,4-phenylenediamine hydrochloride (402 mg, 2.34 mmol) in water (40 cm$^3$) was added slowly to N-[3-(dimethylamino)phenyl]methanesulphonamide (500 mg, 2.34 mmol) in methanol (20 cm$^3$). A saturated solution of potassium dichromate (1 cm$^3$) was added and the mixture refluxed for 15 min. The mixture was cooled and diluted with water (80 cm$^3$), acidified with hydrochloric acid (1M) and then extracted with chloroform (3×30 cm$^3$). The combined extracts were dried over sodium sulphate, filtered and the solvent removed under reduced pressure. Column chromatography (1:9 methanol/dichloromethane) gave the target material as a green solid (153 mg, 22%).

$\delta_H$ (250 MHz, CDCl$_3$): 7.90 (2H, d, J=10 Hz, CH), 7.35 (2H, dd J=10 Hz, J=3 Hz, CH), 7.02 (2H, d, J=3 Hz, CH), 3.18 (12H, s, CH$_3$); $v_{max}$ (KBr)/cm$^{-1}$: 2854, 1596, 1506, 1475, 1428, 1338, 1167, 1142, 807.

Synthesis 15

3,7-Bis(dimethylamino)oxazinium chloride

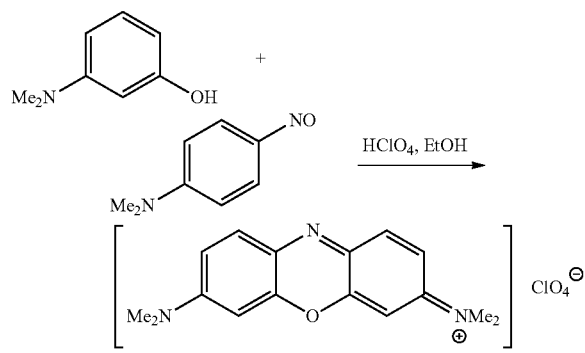

3,7-Bis(dimethylamino)oxazinium chloride

Adapted from A. Kanitz, H, Hartmann, *Eur, J, Org, Chem.* 1999, 923.

3-Dimethylaminophenol (910 mg, 6.67 mmol), N,N-dimethyl-4-nitrosoaniline (1.00 g, 6.67 mmol) and perchloric acid (1 cm$^3$) were heated together in ethanol (20 cm$^3$) for 5 min. The reaction was left to stand at room temperature overnight. The resulting solid was collected by filtration and washed with EtOAc (2×5 cm$^3$). Column chromatography (1:9 methanol/dichloromethane) gave the product as a green/blue solid (13 mg, 1%).

$\delta_H$ (250 MHz, CD$_3$OD): 7.80 (2H, d, J=10 Hz , CH), 7.41 (2H, dd, J=10 Hz, 3 Hz, CH), 6.96 (2H, d, J=3 Hz, CH), 3.31 (12H, s, CH$_3$); $v_{max}$ (KBr)/cm$^{-1}$: 1607, 1526, 1490, 1397, 1346, 1179, 1094, 772.

Synthesis 16

3,6-Bis-(dimethylamino)xanthylium nitrate

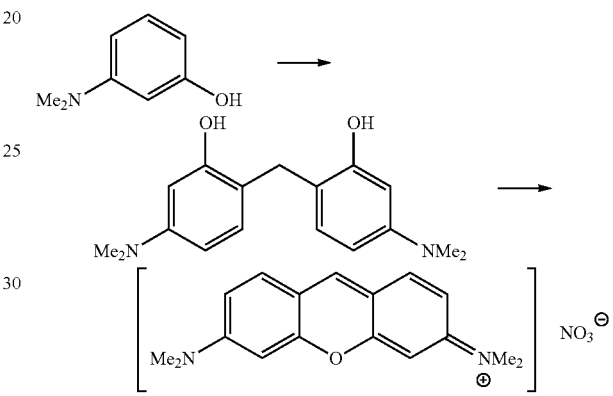

5,5'-Bis-(dimethylamino)-2,2'-methandiyl-di-phenol 3-(Dimethylamino)phenol (3.00 g, 21.87 mmol) was added to MeOH (30 cm$^3$). The mixture was cooled to 6° C. in ice before HCl (1.24 cm$^3$, 10.93 mmol, 32%) was added. Formalin (842 μl, 10.93 mmol, 39%) was added to the reaction mixture. The reaction was stirred at ~6° C. for 22 h after which TLC analysis [2:3 EtOAc/Hexane (R$_f$0.3)] showed the reaction to be complete. The reaction mixture was poured into H$_2$O (40 cm$^3$) and the resulting mixture neutralised by the addition of an aqueous solution of NaHCO$_3$ (sat.). The mixture was extracted with DCM (3×30 cm$^3$) and the combined extracts dried (Na$_2$SO$_4$). The solvent was removed under reduced pressure to yield a purple solid. Column chromatography (2:3 EtOAc/Hexane) gave the product as a purple solid (1.74 g, 56%).

$\delta_H$ (250 MHz, CDCl$_3$): 7.05 (2H, d, J=8 Hz, 2ArH), 6.27 (2H, d, J=8 Hz, 2ArH), 6.13 (2H, s, 2ArH), 3.73 (2H, s, CH$_2$), 2.75 (12H, s, 4CH$_3$); $\delta_c$ (62.5 MHz, CDCl$_3$): 153.5, 150.9, 130.8, 116.5, 106.5, 101.2, 41.0, 29.8; $v_{max}$ (KBr)/cm$^{-1}$: 3366, 2975, 2929, 1626, 1561, 1519, 1438, 1362, 1241, 1142, 1112, 980; m/z (ESI): 287.17 (100%, [M+H]$^+$).

3,6-Bis-(dimethylamino)xanthylium nitrate

H$_2$SO$_4$ (1.6 cm$^3$, 98%) was added to H$_2$O (160 EN) and cooled to 6° C. in ice. 5,5'-Bis-(dimethylamino)-2,2'-methandiyl-di-phenol (440 mg, 1.40 mmol) was added and the mixture heated to 90° C. under N$_2$ for 17 h. The resulting solution was cooled to 6° C. in ice and H$_2$O (4 cm$^3$) added. The mixture was neutralised by the addition of NaOH (40%)

whilst maintaining a reaction temperature of less than 15° C. HCl (800 μl, 32%) was added and the reaction stirred at 20° C. for 30 min. under $N_2$. $FeCl_3.6H_2O$ (755 mg, 2.80 mmol) in $H_2O$ (4 cm$^3$) was added and the mixture heated to 90° C. for 2 h in air. The reaction was allowed to cool to room temperature overnight whereupon a green oil precipitated. The bulk pinkish solution was decanted and the remaining oil taken up in MeOH (20 cm$^3$). The mixture was filtered and the solvent removed under vacuum. The oil was dissolved in $H_2O$ (8 cm$^3$) and $HNO_3$ (few drops, 70%) was added slowly until a purple/green solid precipitated. This was collected by filtration and dried under vacuum overnight to give the product as a green solid (190 mg, 41%).

$\delta_H$ (250 MHz, DMSO-$d_6$): 8.72, (1H, s ArH), 7.83 (2H, d, J=7 Hz, 2ArH), 7.17 (2H, d, J=7 Hz, 2ArH), 6.83 (2H, s, 2ArH), 3.27 (12H, s, 4CH$_3$); $\delta_c$ (62.5 MHz, CDCl$_3$): 157.8, 157.7, 145.9, 132.8, 114.1, 114.0, 95.9, 39.6; $v_{max}$ (KBr)/cm$^{-1}$: 2921, 1653, 1604, 1528, 1497, 1384, 1168, 918; m/z (ESI): 267.15 (100%, [M–NO$_3$]$^+$).

Synthesis 17

3,6-Bis-diethylamino-9-(4-diethylanilino)xanthylium nitrate

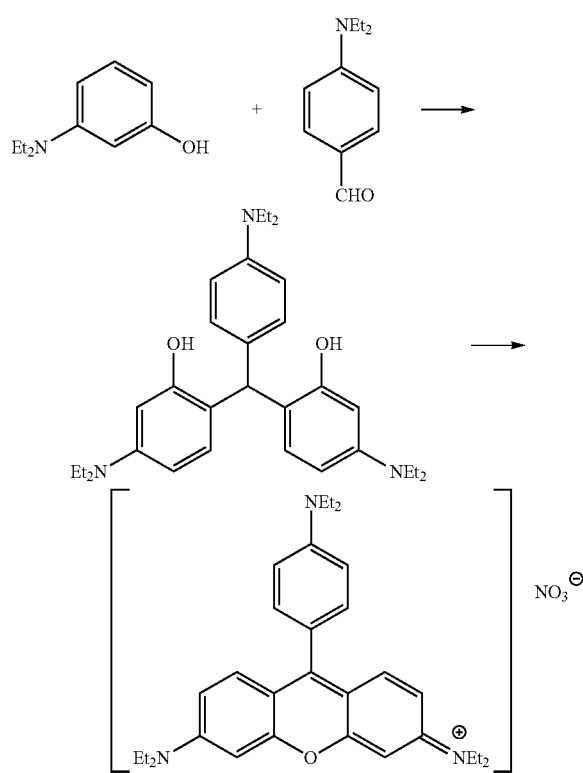

5,5=Bis-dimethylamino-2,2'44-diethylaminobenzilidine)-di-phenol

3-Dimethylamino-phenol (5.00 g, 30.30 mmol) was added to MeOH (20 cm$^3$). HCl (1.73 cm$^3$, 15.15 mmol, 32%) was then added to the mixture. 4-diethylamino-benzaldehyde (2.68 g, 15.15 mmol) was added to the reaction mixture. The reaction was stirred at room temperature for 20 h after which TLC analysis [2:3 EtOAc/Hexane (Rf: 0.25)] showed the reaction to be complete. The reaction mixture was poured into $H_2O$ (40 cm$^3$) and the resulting mixture neutralised by the addition of an aqueous solution of NaHCO3 (sat.). The mixture was extracted with DCM (3×40 cm3) and the combined extracts dried (Na2SO4). The solvent was removed under reduced pressure to yield a red oil. Column chromatography (2:3 EtOAc/Hexane) gave the product as a red solid (4.15 g, 57%).

$\delta_H$ (250 MHz, CDCl$_3$): 7.03 (2H, d, J=8 Hz, 2ArH), 6.71 (2H, d, J=8 Hz, 2ArH), 6.57 (2H, d, J=8 Hz, 2ArH), 6.23-6.18 (2H, m, 2ArH), 6.21 (2H, s, 2ArH), 5.33 (1H, s, CH), 4.98 (2H, bs, OH), 3.33-3.24 (12H, m, 6CH$_2$), 1.12 (18H, t, J=7 Hz, 6CH$_3$); $\delta_c$ (100 MHz, CDCl$_3$): 155.1, 148.3, 146.7, 130.5, 130.2, 130.1, 128.1, 116.1, 112.1, 104.7, 100.0, 44.3, 44.0, 12.7, 12.6; $v_{max}$ (KBr)/cm$^{-1}$: 2969, 2929, 2869, 1618, 1516, 1465, 1399, 1374, 1355, 1266, 1228, 1199, 1094; m/z (ESI): 490.34 (100%, [M+H]$^+$).

3,6-Bis-diethylamino-9-(4-diethylanilino)xanthylium nitrate $H_2SO_4$ (5.4 cm$^3$, 98%) was added to $H_2O$ (600 μl) and cooled to 5° C. in ice. 5,5'-Bis-dimethylamino-2,2'-(4-diethylaminobenzilidine)-di-phenol (2.00 g, 4.19 mmol) was added and the mixture heated to 150° C. under $N_2$ for 3 h. The resulting solution was cooled to 5° C. in ice and $H_2O$ (20 cm$^3$) added. The mixture was neutralised by the addition of NaOH (40%) whilst maintaining a reaction temperature of less than 20° C. HCl (4 cm$^3$, 32%) was added and the reaction stirred at 5° C. for 2 h under $N_2$. $FeCl_3.6H_2O$ (2.26 g, 8.39 mmol) in $H_2O$ (20 cm$^3$) was added and the mixture heated to 90° C. for 2 h in air. The reaction was allowed to cool to room temperature overnight. NaCl was added until a precipitate appeared. The solid was collected by filtration and dried under vacuum. The solid was extracted with MeOH (40 cm$^3$). The solvent was removed under vacuum to yield a green solid. This material was dissolved in $H_2O$ (12 cm$^3$) and $HNO_3$ (1 cm$^3$, 70%) was added slowly until a purple/green solid precipitated. After 10 min the solid was collected by filtration and dried under vacuum to give the product as a green solid (1.11 g, 50%).

$\delta_H$ (250 MHz, CD$_3$OD): 7.50-7.40 (4H, m, 4ArH), 7.20-7.03 (4H, m, 4ArH), 6.93 (2H, s, 2ArH), 3.72-3.45 (12H, m, 6CH$_2$), 1.30-1.15 (18H, t, J=7 Hz, 6CH$_3$); $\delta_c$ (100 MHz, CDCl$_3$): 159.6, 157.3, 156.5, 141.3, 133.4, 123.5, 115.9, 97.7, 54.5, 47.1, 13.0, 11.2; $v_{max}$ (KBr)/cm$^{-1}$: 1646, 1594, 1473, 1419, 1384, 1349, 1186, 1073; m/z (ESI): 470.32 (100%, [M–NO$_3$]$^+$).

Synthesis 18

3,6-Bis-diethylamino-9-(4-nitrophenyl)xanthylium nitrate

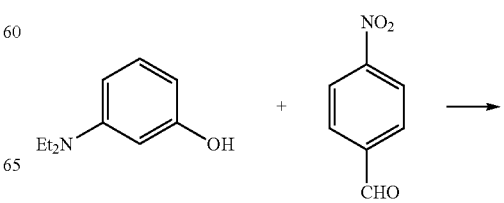

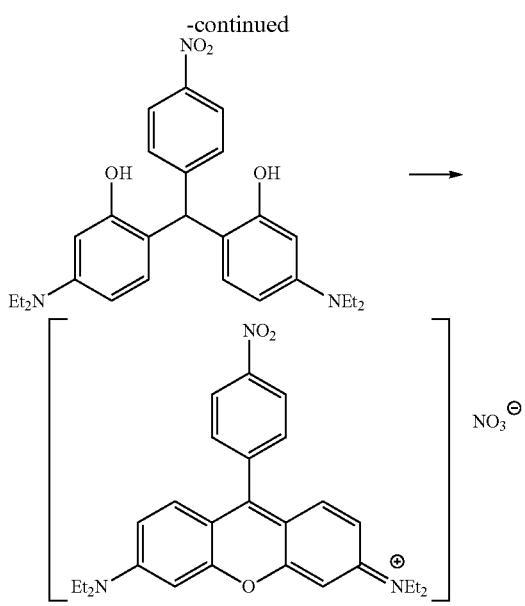

5,5'-Bis-dimethylamino-2,2'-(4-nitrobenzilidine)-di-phenol

3-Dimethylamino-phenol (3.00 g, 18.18 mmol) was added to MeOH (30 cm$^3$). HCl (1.04 cm$^3$, 9.09 mmol, 32%) was then added to the mixture. 4-nitro-benzaldehyde (1.37 g, 9.09 mmol) was added to the reaction mixture. The reaction was heated to 40° C. for 18 h and the 50° C. for 24 h after which TLC analysis [1:1 EtOAc/Hexane (R$_f$ 0.3)] showed the reaction to be almost complete. The reaction mixture was poured into H$_2$O (40 cm$^3$) and the pH of resulting mixture basified by the addition of an aqueous solution of NaHCO$_3$ (sat.). The mixture was extracted with DCM (3×30 cm$^3$) and the combined extracts dried (Na$_2$SO$_4$). The solvent was removed under reduced pressure to yield a red oil. Column chromatography (1:1 EtOAc/Hexane) gave the product as an orange red solid (2.84 g, 69%).

$\delta_H$ (250 MHz, CDCl$_3$): 8.11 (2H, d, J=8 Hz, 2ArH), 7.34 (2H, d, J=8 Hz, 2ArH), 6.65 (2H, d, J=8 Hz, 2ArH), 6.20-6.15 (4H, m, 4ArH), 5.71 (1H, s, CH), 3.27 (8H, q, J=7 Hz, 4CH$_2$), 1.11 (12H, t, J=7 Hz, 4CH$_3$); $\delta_C$ (100 MHz, CDCl$_3$): 154.5, 151.8, 148.4, 146.2, 130.6, 130.0, 123.4, 115.1, 104.9, 99.8, 44.4, 43.9, 12.6; $\nu_{max}$ (KBr)/cm$^{-1}$: 2971, 1618, 1559, 1540, 1522, 1457, 1343, 1375, 1228, 1094; m/z (ESI): 464.25 (100%, [M+H]$^+$).

3,6-Bis-diethylamino-9-(4-nitrophenyl)xanthylium nitrate

H$_2$SO$_4$ (1.2 cm$^3$, 98%) was added to H$_2$O (120 µl) and cooled to 5° C. in ice. 5,5'-Bis-dimethylamino-2,2'-(4-nitrobenzilidine)-di-phenol (400 mg, 0.863 mmol) was added and the mixture heated to 70° C. under N$_2$ for 20 h and then at 90° C. for 29 h. The resulting solution was cooled to 6° C. in ice and H$_2$O (4 cm$^3$) added. The mixture was neutralised by the addition of NaOH (20%) whilst maintaining a reaction temperature of less than 16° C. HCl (1.2 cm$^3$, 32%) was added and the reaction stirred at 19° C. for 30 min under N$_2$. FeCl$_3$.6H$_2$O (467 mg, 1.73 mmol) in H$_2$O (4 cm$^3$) was added and the mixture heated to 88° C. for 2 h in air. The reaction was allowed to cool to 20° C. overnight. The resulting green precipitate was collected by filtration and dried under vacuum overnight. This material was dissolved in H$_2$O (4 cm$^3$) and HNO$_3$ (few drops, 70%) was added slowly until a purple/green solid precipitated. After 10 min the solid was collected by filtration and dried under vacuum. Column chromatography (1:9 MeOH/DCM) gave the product as a green solid (243 mg, 56%).

$\delta_H$ (250 MHz, CD$_3$OD): 8.53 (2H, d, J=7 Hz, 2ArH), 7.76 (2H, d, J=7 Hz, 2ArH), 7.30 (2H, d, J=7 Hz, 2ArH), 7.10 (2H, d, J=7 Hz, 2ArH), 7.02 (2H, s, 2ArH), 3.83-3.57 (8H, m, 4CH$_2$), 1.44-1.18 (12H, m, 4CH$_3$); $\delta_C$ (100 MHz, CD$_3$OD): 158.0, 155.9, 154.5, 148.9, 138.7, 131.1, 130.8, 123.6, 114.4, 112.8, 96.2, 45.5, 11.4; $\nu_{max}$ (KBr)/cm$^{-1}$: 2977, 1647, 1593, 1467, 1384, 1347, 1184, 1074; m/z (ESI): 444.23 (100%, [M−NO$_3$]$^+$).

Synthesis 19

1,1,7,7,11,11,17,17-Octamethyl-2,3,6,7,12,13,16,17-octahydro-1H,5H,11H,15H-diquinolizino[1,9-bc;1',9'-hi]xanthylium nitrate

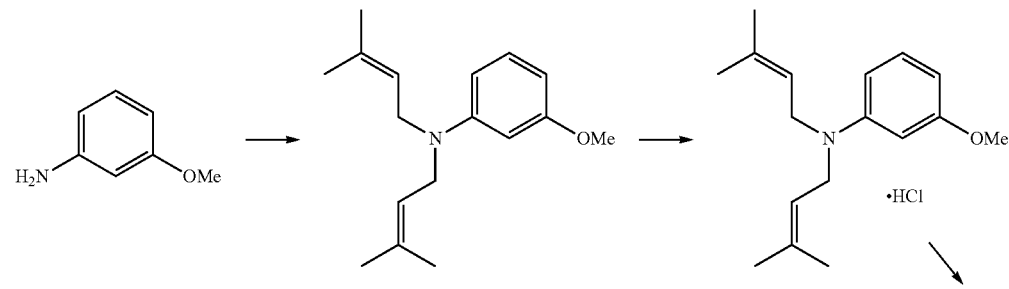

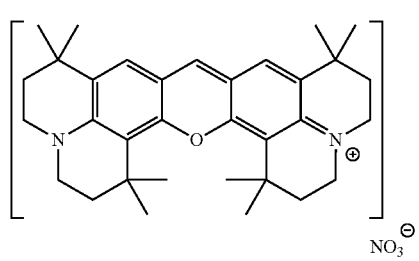 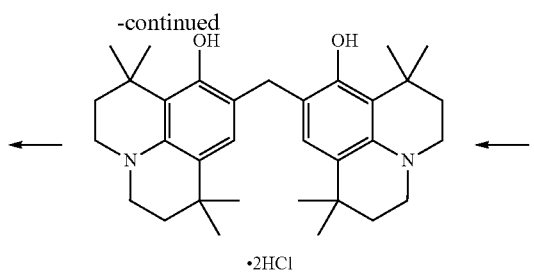

3-Methoxy-N,N-Bis(3-methylbut-2-ene)aniline

Uddin, M. J., Marnett L., J., *Organic Letters,* 10, 2008, 4799.

To a solution of anisidine (5.00 g, 40 65 mmol) in $CH_3CN$ (20 cm$^3$), $K_2CO_3$ (11.22 g, 80.13 mmol) and 1-chloror-3-methylbut-2-ene (8.49 g, 80.13 mmol) were added. Molecular sieves (4 Å, 10 g) were added and the reaction stirred at room temperature for 48 h. The resulting mixture was filtered and the solid washed with $CH_3CN$ (2×15 cm$^3$). The solvent was removed from the filtrate under reduced pressure. Column chromatography [1:1 40:60 petrol/DCM (R$_f$ 0.4)] gave the product as a colourless oil (8.54 g, 81%).

$\delta_H$ (250 MHz, CDCl$_3$): 7.14-7.07 (1H, m, ArH), 6.32 (1H, d, J=8 Hz, ArH), 6.30-6.25 (2H, m, 2ArH), 5.23-5.19 (2H, m, 2CH), 3.84 (4H, d, J=6 Hz, 2CH$_2$), 3.77 (3H, s, OCH$_3$), 1.72 (6H, s, 2CH$_3$), 1.70 (6H, s, 2CH$_3$); $\delta_c$ (62.5 MHz, CDCl$_3$): 160.8, 150.5, 134.1, 129.8, 121.8, 105.9, 101.0, 99.1, 55.1, 48.4, 25.8, 18.0; $\nu_{max}$ (neat)/cm$^{-1}$: 2967, 2927, 1671, 1610, 1498, 1452, 1376, 1327, 1263, 1214, 1164, 1060, 1043, 986, 941; m/z (ESI): 260.20 (100%, [M+H]$^+$).

3-Methoxy-N,N-Bis(3-methylbut-2-ene)aniline hydrochloride

Based on Uddin, M. J., Marnett L., J., *Organic Letters,* 10, 2008, 4799.

3-Methoxy-N,N-Bis(3-methylbut-2-ene)aniline (7.50 g, 28.96 mmol) was dissolved in EtOH (20 cm$^3$). HCl (9.65 cm$^3$, 32%) was added and the reaction mixture stirred at room temperature for 1 h. The solvent was removed under vacuum overnight to yield the product as a colourless sticky solid (8.33 g, 97%).

$\delta_H$ (250 MHz, DMSO-d$_6$): 7.55-7.35 (3H, m, 3ArH), 7.04-6.95 (1H, m, ArH), 5.30-5.02 (2H, m, 2CH), 4.30-4.01 (4H, m, 2CH$_2$), 3.78 (3H, s, OCH$_3$), 1.56 (6H, s, 2CH$_3$), 1.52 (6H, s, 2CH$_3$);

1,1,7,7-tetramethyl-8-hydroxyjulolidine

3-Methoxy-N,N-Bis(3-methylbut-2-ene)aniline hydrochloride (7.00 g, 17.68 mmol) was added to methanesulphonic acid (70 cm$^3$). The resulting solution was heated to 95° C. for 24 h. It was then cooled to room temperature and ice water (140 cm$^3$) added. The mixture was neutralised by the addition of NH$_4$OH (sat.) and then extracted with CHCl$_3$ (3×60 cm$^3$). The extracts were dried (Na$_2$SO$_4$) and the solvent removed under reduced pressure. Column chromatography [3:2 40:60 petrol/DCM (R$_f$ 0.25)] gave the product as a pink solid (3.04 g, 52%).

$\delta_H$ (250 MHz, CDCl$_3$): 6.89 (1H, d, J=8 Hz, ArH), 6.00 (1H, d, J=8 Hz, ArH), 4.50 (1H, s, OH), 3.09-2.99 (4H, m, 2CH$_2$), 1.80-1.72 (4H, m, 2CH$_2$), 1.42 (6H, s, 2CH$_3$), 1.24 (6H, s, 2CH$_3$); $\delta_c$ (62.5 MHz, CDCl$_3$): 153.2, 143.6, 125.0, 124.3, 116.8, 105.3, 47.8, 47.4, 40.6, 37.4, 32.4, 32.3, 29.2; $\nu_{max}$ (KBr)/cm$^{-1}$: 2953, 2928, 2859, 2826, 1586, 1424, 1385, 1272, 1165, 1133, 1102, 952, 800; m/z (ESI): 246.19 (100%, [M+H]$^+$).

7,7-Methylene-bis(1,1,7,7-tetramethyl-8-hydroxyjulolidine) dihydrochloride 1,1,7,7-tetramethyl-8-hydroxyjulolidine (800 mg, 3.27 mmol) was added to MeOH (10 cm$^3$). HCl (186 µl, 1.63 mmol, 32%) was then added to the mixture. Formalin (122 µl, 1.63 mmol, 39%) was added to the reaction mixture. The reaction was heated to 60° C. for 16 h and the after which TLC analysis [3:7 EtOAc/Hexane (R$_f$ 0.6)] showed the reaction to be complete. The reaction volume was reduced by half under reduced pressure and the remainder cooled to −6° C. overnight. The resulting precipitate was collected by filtration and dried under vacuum to give the product as a green solid (494 mg, 60%).

$\delta_H$ (250 MHz, DMSO-d$_6$): 8.95 (2H, bs, 2OH), 7.08 (2H, s, 2ArH), 3.90 (2H, s, CH$_2$), 3.39-3.25 (4H, m, 2CH$_2$), 2.19-1.86 (4H, m, 2CH$_2$), 1.41 (6H, s, 2CH$_3$), 1.17 (6H, s, 2CH$_3$); $\nu_{max}$ (KBr)/cm$^{-1}$: 3390, 2960, 2928, 2619, 2531, 1472, 1428, 1386, 1361, 1265, 1177; m/z (ESI): 503.36 (100%, [M−HCl$_2$]$^+$).

1,1,7,7,11,11,17,17-Octamethyl-2,3,6,7,12,13,16,17-octahydro-1H,5H,11H,15H-diquinolizino[1,9-bc;1',9'-hi]xanthylium nitrate $H_2SO_4$ (600 µl, 98%) was added to $H_2O$ (60 µl) and cooled to 5° C. in ice. 7,7-Methylene-bis(1,1,7,7-tetramethyl-8-hydroxyjulolidine) dihydrochloride (200 mg, 0.348 mmol) was added and the mixture heated to 50° C. under N$_2$ for 4 h and then 65° C. for 2 h. The resulting solution was cooled to 6° C. in ice and H$_2$O (2 cm$^3$) added. The mixture was neutralised by the addition of NaOH (20%) whilst maintaining a reaction temperature of less than 18° C. HCl (400 µl, 32%) was added and the reaction stirred at 20° C. for 30 min under N$_2$. FeCl$_3$.6H$_2$O (188 mg, 0.696 mmol) in H$_2$O (1 cm$^3$) was added and the mixture heated to 89° C. for 3 h in air. The reaction was allowed to cool to room temperature overnight. The resulting solid was collected by filtration and dried under vacuum overnight. This material was dissolved in H$_2$O (20 cm$^3$) and HNO$_3$ (70%) was added slowly until a green solid precipitated. After 10 min the solid was collected by filtration and dried under vacuum to give the product as a green solid (126 mg, 66%).

$\delta_H$ (250 MHz, CD$_3$OD): 8.29 (1H, s, ArH), 7.58 (2H, d, J=8 Hz, 2ArH), 3.66 (4H, t, J=6 Hz, 2CH$_2$), 3.57 (4H, t, J=5 Hz, 2CH$_2$), 1.87 (4H, t, J=5 Hz, 2CH$_2$), 1.82 (4H, t, J=6 Hz, 2CH$_2$), 1.71 (13H, s, 4CH$_2$), 1.37 (12H, s, 4CH$_3$); $\delta_c$ (100 MHz, CD$_3$OD): 154.3, 151.8, 144.3, 132.9, 126.7, 114.3, 114.2, 38.8, 33.8, 31.9, 31.6, 27.8, 27.6; $v_{max}$ (KBr)/cm$^{-1}$: 2957, 1596, 1507, 1384, 1309, 1202, 1038; m/z (ESI): 483.34 (100%, [M–NO$_3$]$^+$).

Synthesis 20

3,6-Bis-morpholino-xanthylium nitrate

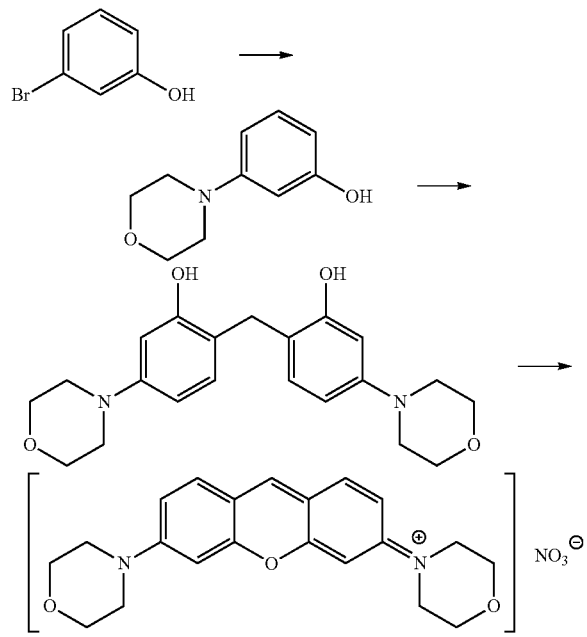

N-(3-Hydroxyphenyl)morpholine

Pd(OAc)$_2$ (78 mg, 0.347 mmol) was added to morpholine (1.81 g, 20.81 mmol) and 3-bromophenol (3.00 g, 17.34 mmol) under N$_2$. 2,8,9-triisobutyl-2,5,8,9-tetraaza-1-phosphabicyclo[3,3,3]undecane (238 mg, 0.694 mmol), LiHMDS (39.88 cm$^3$, 1 M in THF) and dry toluene (80 cm$^3$) were added sequentially. The mixture was heated to 80° C. for 18 h, before being cooled to room temperature. The solvent was removed under vacuum and the residue extracted with hot EtOAc/DCM (1:1, 200 cm$^3$). The mixture was filtered and the solvent removed. Column chromatography [1:1 EtOAc/DCM (R$_f$ 0.25)] gave the product as an off-white solid (2.38 g, 77%).

$\delta_H$ (250 MHz, CDCl$_3$): 7.14-7.08 (1H, m, ArH), 6.48 (1H, d, J=8 Hz, ArH), 6.36-6.32 (2H, m, 2ArH), 5.82 (1H, bs, OH), 3.85 (4H, t, J=5 Hz, 2CH$_2$), 3.11 (4H, t, J=5 Hz, 2CH$_2$); $\delta_C$ (62.5 MHz, CDCl$_3$): 156.9, 152.6, 130.2, 108.2, 107.6, 103.2, 66.8, 49.4; $v_{max}$ (KBr)/cm$^{-1}$: 3242, 2974, 2816, 1610, 1582, 1491, 1448, 1267, 1191, 1104, 1064, 975, 773; m/z (ESI): 180.10 (100%, [M+H]$^+$).

5,5=Bis-morpholino-2,2=methandiyl-di-phenol

N-(3-Hydroxyphenyl)morpholine (2.00 g, 11.17 mmol) was added to MeOH (25 cm$^3$). The mixture was cooled to 5° C. in ice before HCl (637 µl, 5.89 mmol, 32%) was added. Formalin (419 µl, 5.89 mmol, 39%) was added to the reaction mixture. The reaction was stirred at 5° C. for 18 h, and then at room temperature for 24 h. The reaction mixture was poured into H$_2$O (40 cm$^3$) and the resulting mixture neutralised by the addition of an aqueous solution of NaHCO$_3$ (sat.). The mixture was extracted with DCM (3×30 cm$^3$) and the combined extracts dried (Na$_2$SO$_4$). The solvent was removed under reduced pressure. Column chromatography [4:1 EtOAc/Hexane (R$_f$ 0.3)] gave the product as a purple solid (684 mg, 33%).

$\delta_H$ (250 MHz, DMSO-d$_6$): 9.08 (2H, s, OH), 6.76 (2H, d, J=8 Hz, 2ArH), 6.35 (2H, s, 2ArH), 6.29 (2H, d, J=8 Hz, 2ArH), 3.72-3.68 (8H, m, 4CH$_2$), 3.59 (2H, s, CH$_2$), 2.98-2.94 (8H, m, 4CH$_2$); $\delta_C$ (62.5 MHz, DMSO-d$_6$): 155.3, 150.5, 130.4, 118.7, 106.5, 102.2, 66.2, 49.0, 28.0; $v_{max}$ (KBr)/cm$^{-1}$: 3246, 2965, 2825, 1618, 1584, 1527, 1451, 1261, 1191, 1112, 981, 882; m/z (ESI): 371.19 (100%, [M+H]$^+$).

3,6-Bis-(morpholino)xanthylium nitrate

H$_2$SO$_4$ (900 µl, 98%) was added to H$_2$O (100 µl) and cooled to room temperature. 5,5'-bis-morpholino-2,2'-methandiyl-di-phenol (300 mg, 0.811 mmol) was added and the mixture heated to 140° C. under N$_2$ for 3 h. The resulting solution was cooled to room temperature and H$_2$O (2 cm$^3$) added. The mixture was neutralised by the addition of NaOH (40%) whilst maintaining a reaction temperature of less than 15° C. HCl (600 µl, 32%) was added and the reaction stirred at room temperature for 30 min. under N$_2$. FeCl$_3$.6H$_2$O (438 mg, 1.62 mmol) in H$_2$O (2 cm$^3$) was added and the mixture heated to 90° C. for 2 h in air. The reaction was allowed to cool to room temperature. The resulting solid was collected by filtration and dried under vacuum. This material was dissolved in H$_2$O (10 cm$^3$) and HNO$_3$ (300 µl, 70%) was added slowly until a green solid precipitated. After 10 min the solid was collected by filtration and dried under vacuum to give the product as a green solid (198 mg, 67%).

$\delta_H$ (250 MHz, CD$_3$OD): 8.70 (1H, s, ArH), 7.87 (2H, d, J=7 Hz, 2ArH), 7.37 (2H, d, J=7 Hz, 2ArH), 7.15 (2H, s, 2ArH), 3.86-3.85 (8H, m, 4CH$_2$), 3.79-3.67 (8H, m, 4CH$_2$); $\delta_C$ (100 MHz, CD$_3$OD): 158.4, 157.9, 146.5, 133.3, 115.2, 114.6, 96.9, 66.0, 46.9; $v_{max}$ (KBr)/cm$^{-1}$: 2865, 1598, 1489, 1384, 1244, 1170, 1109, 1034, 903; m/z (ESI): 351.17 (100%, [M–NO$_3$]$^+$).

Synthesis 21

3,6-Bis-piperidino-xanthylium nitrate

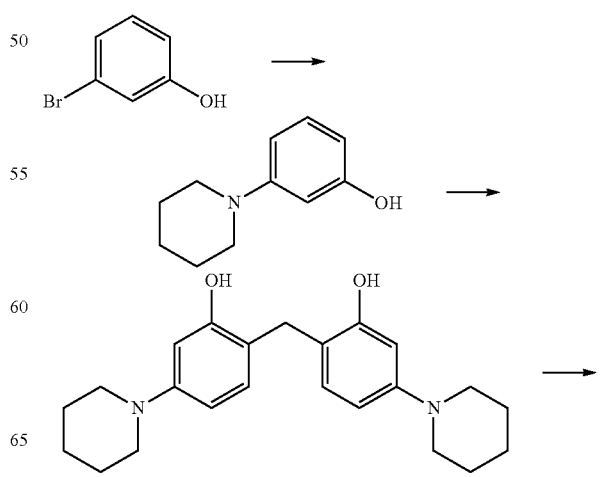

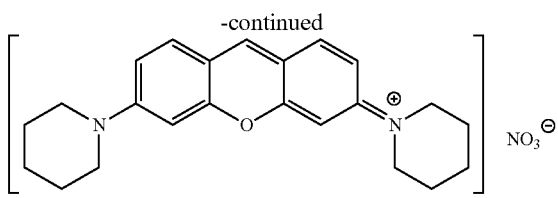

N-(3-Hydroxyphenyl)piperidine

Pd(OAc)$_2$ (129 mg, 0.578 mmol) was added to piperidine (2.95 g, 34.68 mmol) and 3-bromophenol (5.00 g, 28.90 mmol) under N$_2$. 2,8,9-triisobutyl-2,5,8,9-tetraaza-1-phosphabicyclo[3,3,3]undecane (397 mg, 1.16 mmol), LiHMDS (66.50 cm$^3$, 1 M in THF) and dry toluene (110 cm$^3$) were added sequentially. The mixture was heated to 80° C. for 18 h, before being cooled to room temperature. H$_2$O (50 cm$^3$) was added and the layers separated. The aqueous layer was extracted with toluene (3×30 cm$^3$). The combined organics were dried (Na$_2$SO$_4$) and the solvent removed under reduced pressure. Column chromatography [3:7 EtOAc/Hexane (R$_f$ 0.4)] gave the product as an off-white solid (2.56 g, 50%).

$\delta_H$ (250 MHz, CDCl$_3$): 7.11-7.04 (1H, m, ArH), 6.52 (1H, d, J=8 Hz, ArH), 6.35 (1H, s, ArH), 6.29 (1H, d, J=8 Hz, ArH), 5.84 (1H, bs, OH), 3.08 (4H, t, J=5 Hz, 2CH$_2$), 1.75-1.62 (4H, m, 2CH$_2$), 1.60-1.50 (2H, m, CH$_2$); $\delta_c$ (62.5 MHz, CDCl$_3$): 156.7, 153.4, 130.0, 109.3, 107.4, 104.6, 51.0, 25.5, 24.2; $\nu_{max}$ (KBr)/cm$^{-1}$: 3064, 2959, 2937, 2921, 2856, 1597, 1503, 1454, 1276, 1201, 1133, 1104, 971, 877; m/z (ESI): 178.12 (100%, [M+H]$^+$).

5,5'-Bis-piperidino-2,2'-methandiyl-di-phenol

N-(3-Hydroxyphenyl)piperidine (1.50 g, 8.52 mmol) was added to MeOH (20 cm$^3$). The mixture was cooled to 5° C. in ice before HCl (486 µl, 4.26 mmol, 32%) was added. Formalin (327 µl, 4.26 mmol, 39%) was added to the reaction mixture. The reaction was stirred at 5° C. for 18 h, and then at 30° C. for 18 h. The reaction mixture was poured into H$_2$O (30 cm$^3$) and the resulting mixture neutralised by the addition of an aqueous solution of NaHCO$_3$ (sat.). The mixture was extracted with DCM (3×30 cm$^3$) and the combined extracts dried (Na$_2$SO$_4$). The solvent was removed under reduced pressure. Column chromatography (3:7 EtOAc/Hexane (Rf: 0.4)] gave the product as a purple/pink solid (886 mg, 57%).

$\delta_H$ (250 MHz, CDCl$_3$): 7.06 (2H, d, J=8 Hz, ArH), 6.44 (2H, d, J=8 Hz, ArH), 6.23 (2H, s, ArH), 3.72 (2H, s, CH$_2$), 2.96-2.83 (8H, m, 4CH$_2$), 1.70-1.56 (8H, m, 4CH$_2$), 1.56-1.40 (4H, m, 2CH$_2$); $\delta_c$ (62.5 MHz, CDCl$_3$): 153.4, 151.7, 130.8, 119.9, 110.1, 105.4, 51.3, 30.2, 25.4, 24.2; $\nu_{max}$ (KBr)/cm$^{-1}$: 3268, 2928, 2854, 2798, 1618, 1577, 1522, 1497, 1447, 1383, 1253, 1177, 1115, 969; m/z (ESI): 367.24 (100%, [M+H]$^+$).

3,6-Bis-(piperidino)xanthylium nitrate

H$_2$SO$_4$ (900 µl, 98%) was added to H$_2$O (100 µl) and cooled to room temperature. 5,5'-bis-piperidino-2,2'-methandiyl-di-phenol (350 mg, 0.956 mmol) was added and the mixture heated to 140° C. under N$_2$ for 3 h. The resulting solution was cooled to room temperature and H$_2$O (5 cm$^3$) added. The mixture was neutralised by the addition of NaOH (40%) whilst maintaining a reaction temperature of less than 20° C. HCl (700 µl, 32%) was added and the reaction stirred at room temperature for 30 min. under N$_2$. FeCl$_3$.6H$_2$O (516 mg, 1.91 mmol) in H$_2$O (3 cm$^3$) was added and the mixture heated to 80° C. for 2 h in air. The reaction was allowed to cool to room temperature overnight whereupon a green oil precipitated. The bulk pinkish solution was decanted and the remaining oil taken up in fresh H$_2$O (8 cm$^3$). HNO$_3$ (few drops, 70%) was added slowly until a green solid precipitated. This was collected by filtration and dried under vacuum. Column chromatography (1:9 MeOH/DCM (R$_f$ 0.2)] gave the product as a green solid (117 mg, 30%).

$\delta_H$ (250 MHz, CD$_3$OD): 8.51 (1H, s, ArH), 7.77 (2H, d J=9 Hz, ArH), 7.30 (2H, d, J=9 Hz, ArH), 7.07 (2H, s, ArH), 3.86-3.72 (8H, m, 4CH$_2$), 1.90-1.66 (12H, m, 6CH$_2$); $\delta_c$ (100 MHz, CD$_3$OD): 158.5, 157.1, 144.9, 133.1, 114.5, 96.6, 46.9, 25.7, 23.9; $\nu_{max}$ (KBr)/cm$^{-1}$: 2928, 1653, 1577, 1560, 1490, 1384, 1244, 1169, 1017; m/z (ESI): 347.21 (100%, [M–NO$_3$]$^+$).

Synthesis 22

3,6-Bis-pyrrolidino-xanthylium nitrate

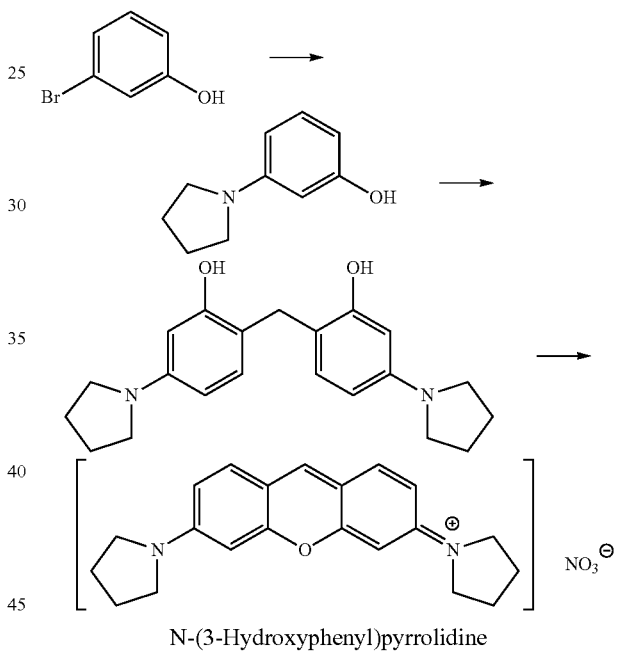

N-(3-Hydroxyphenyl)pyrrolidine

Pd(OAc)$_2$ (129 mg, 0.578 mmol) was added to pyrrolidine (2.46 g, 34.68 mmol) and 3-bromophenol (5.00 g, 28.90 mmol) under N$_2$. 2,8,9-triisobutyl-2,5,8,9-tetraaza-1-phosphabicyclo[3,3,3]undecane (397 mg, 1.16 mmol), LiHMDS (66.50 cm$^3$, 1 M in THF) and dry toluene (110 cm$^3$) were added sequentially. The mixture was heated to 80° C. for 18 h, before being cooled to room temperature. H$_2$O (50 cm$^3$) was added and the layers separated. The aqueous layer was extracted with toluene (3×40 cm$^3$). The combined organics were dried (Na$_2$SO$_4$) and the solvent removed under reduced pressure. Column chromatography [3:7 EtOAc/Hexane (R$_f$ 0.5)] gave the product as an off-white solid (1.92 g, 51%).

$\delta_H$ (250 MHz, CDCl$_3$): 7.10-7.04 (1H, m, ArH), 6.18-6.11 (2H, m, 2ArH), 6.05 (1H, s, ArH), 4.70 (1H, bs, OH), 3.30-3.20 (4H, m, 2CH$_2$), 2.01-1.96 (4H, m, 2CH$_2$); $\delta_c$ (62.5 MHz, CDCl$_3$): 156.5, 149.5, 130.1, 104.8, 102.5, 98.7, 47.7, 25.5; $\nu_{max}$ (KBr)/cm$^{-1}$: 3315, 2979, 2891, 2852, 1618, 1578, 1518, 1491, 1459, 1217, 1202, 1170, 817; m/z (ESI): 164.11 (100%, [M+H]$^+$).

5,5'-Bis-pyrrolidino-2,2'-methandiyl-di-phenol

N-(3-Hydroxyphenyl)pyrrolidine (1.00 g, 6.13 mmol) was added to MeOH (15 cm³). HCl (350 µl, 3.07 mmol, 32%) was then added. Formalin (236 µl, 3.07 mmol, 39%) was added to the reaction mixture. The reaction was stirred at room temperature overnight, and then at 30° C. for 24 h. The reaction mixture was poured into H₂O (30 cm³) and the resulting mixture neutralised by the addition of an aqueous solution of NaHCO₃ (sat.).

The mixture was extracted with DCM (3×30 cm³) and the combined extracts dried (Na₂SO₄). The solvent was removed under reduced pressure. Column chromatography [3:7 EtOAc/Hexane ($R_f$ 0.3)] gave the product as an off-white solid (384 mg, 37%).

$\delta_H$ (250 MHz, CDCl₃): 7.01 (2H, d, J=8 Hz, ArH), 6.92 (2H, bs, OH), 6.05 (2H, d, J=8 Hz, 2ArH), 5.93 (2H, s, ArH), 3.72 (2H, s, CH₂), 3.13-3.00 (8H, m, 4CH₂), 1.96-1.85 (8H, m, 4CH₂); $\delta_c$ (62.5 MHz, CDCl₃): 153.2, 148.2, 130.8, 114.9, 105.3, 99.5, 47.7, 29.7, 25.4; $v_{max}$ (KBr)/cm⁻¹: 3389, 2967, 2834, 1624, 1560, 1515, 1483, 1431, 1371, 1204, 1176, 1126; m/z (ESI): 339.21 (100%, [M+H]⁺).

3,6-Bis-(pyrrolidino)xanthylium nitrate

H₂SO₄ (500 µl, 98%) was added to H₂O (50 µl) and cooled to room temperature. 5,5'-bis-pyrollidino-2,2'-methandiyl-di-phenol (150 mg, 0.419 mmol) was added and the mixture heated to 140° C. under N₂ for 3 h. The resulting solution was cooled to room temperature and ice H₂O (1 cm³) added. The mixture was neutralised by the addition of NaOH (40%) whilst maintaining a reaction temperature of less than 20° C. HCl (300 µl, 32%) was added and the reaction stirred at room temperature for 30 min. under N₂. FeCl₃.6H₂O (226 mg, 0.838 mmol) in H₂O (1 cm³) was added and the mixture heated to 90° C. for 2 h in air. The reaction was allowed to cool to room temperature overnight. The resulting solid was collected by filtration and dried under vacuum. This material was dissolved in H₂O (5 cm³) and HNO₃ (few drops, 70%) was added slowly until a green solid precipitated. After 10 min the solid was collected by filtration and dried under vacuum to give the product as a green solid (121 mg, 71%).

$\delta_H$ (250 MHz, CD₃OD): 8.51 (1H, s, ArH), 7.74 (2H, d, J=9 Hz, ArH), 7.00 (2H, d, J=9 Hz, 2ArH), 6.72 (2H, s, ArH), 3.69-3.52 (8H, m, 4CH₂), 2.23-2.10 (8H, m, 4CH₂); $\delta_c$ (100 MHz, CDCl₃): 157.4, 155.0, 145.6, 132.8, 114.7, 114.0, 96.2, 47.0, 24.7; $v_{max}$ (KBr)/cm⁻¹: 2961, 2865, 1652, 1601, 1518, 1384, 1345, 1165, 820; m/z (ESI): 319.18 (100%, [M–NO₃]⁺).

Synthesis 23

3,6-Bis-morpholino xanthene dihydrochloride

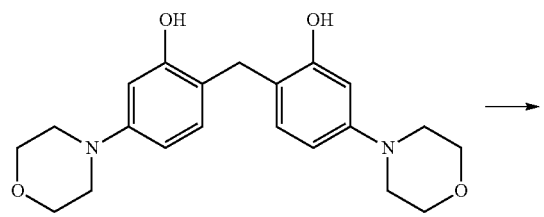

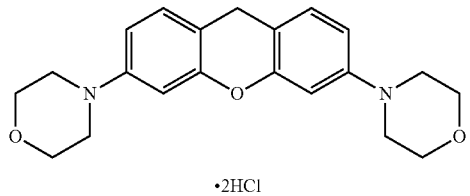

•2HCl 3,6-Bis-morpholino xanthene dihydrochloride

H₂SO₄ (1 cm³, 98%) was added to water (100 µl) and the mixture cooled to room temperature. 5,5'-Bis-morpholino-2,2'-methandiyl-di-phenol (300 mg, 0.811 mmol) was added portion wise with stirring. The mixture was then heated at 140° C. for 3 h under nitrogen. The resulting solution was cooled to room temperature before the addition of ice water (5 cm³). The mixture was neutralised by the slow addition of sodium hydroxide (40% in water) keeping the temperature below 20° C. The resulting pink precipitate was collected by filtration, washed with water (2×3 cm³). The intermediate was added to a solution of methanol (5 cm³) and HCl (600 µl, 32%) and stirred for 30 min until homogeneous. The solvent was removed under reduced pressure and the solid dried under vacuum overnight to give the product as a purple solid (276 mg, 80%).

$\delta_H$ (250 MHz, DMSO-d₆): 7.24 (2H, d, J=8 Hz, 2ArH), 7.10-7.00 (2H, m, 2ArH), 7.05 (2H, s, 2ArH), 3.94 (2H, s, CH₂), 3.92-3.81 (8H, m, 4CH₂), 3.35-3.27 (8H, m, 4CH₂); $v_{max}$ (KBr)/cm⁻¹: 2916, 2866, 2637, 2581, 1649, 1597, 1487, 1459, 1384, 1246, 1167, 1118, 1058; m/z (ESI): 353.19 (100%, [M–HCl₂]⁺).

Synthesis 24

3,6-Bis-pyrrolidino xanthene dihydrochloride

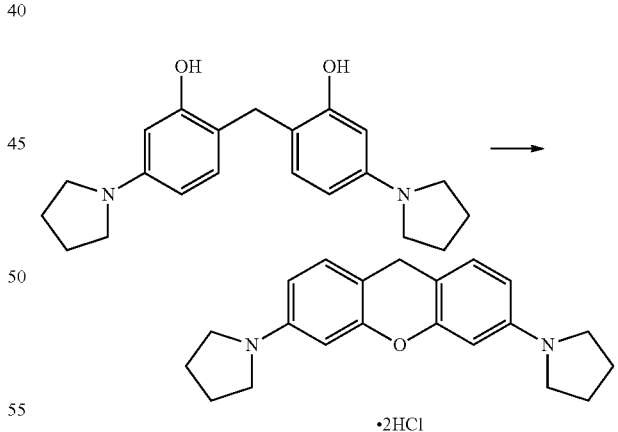

•2HCl 3,6-Bis-pyrrolidino xanthene dihydrochloride

H₂SO₄ (900 µl, 98%) was added to water (100 µl) and the mixture cooled to room temperature. 5,5'-Bis-pyrrolidino-2,2'-methandiyl-di-phenol (100 mg, 0.296 mmol) was added portion wise with stirring. The mixture was then heated at 140° C. for 3 h under nitrogen. The resulting solution was cooled to room temperature before the addition of ice water (5 cm³). The mixture was neutralised by the slow addition of sodium hydroxide (40%) keeping the temperature below 20° C. The resulting precipitate was collected by filtration, washed with water (5 cm³). The intermediate was added to a solution of methanol (5 cm³) and HCl (400 μl, 32%) and stirred for 30 min until homogeneous. The solvent was removed under reduced pressure and the solid dried under vacuum overnight to give the product as a purple solid (84 mg, 72%).

$\delta_H$ (250 MHz, DMSO-$d_6$): 7.13 (2H, d, J=8 Hz, ArH), 6.70-6.58 (6H, m, 6ArH), 3.87 (2H, s, $CH_2$), 3.40-3.29 (4H, m, $4CH_2$), 2.10-1.94 (4H, m, $4CH_2$); $\nu_{max}$ (KBr)/cm$^{-1}$: 2984, 2658, 1604, 1508, 1492, 1384, 1345, 1221, 1164, 1117, 1059, 1000; m/z (ESI): 321.20 (100%, [M–HCl$_2$]$^+$).

Synthesis 25

3,6-Bis-piperidino xanthene dihydrochloride

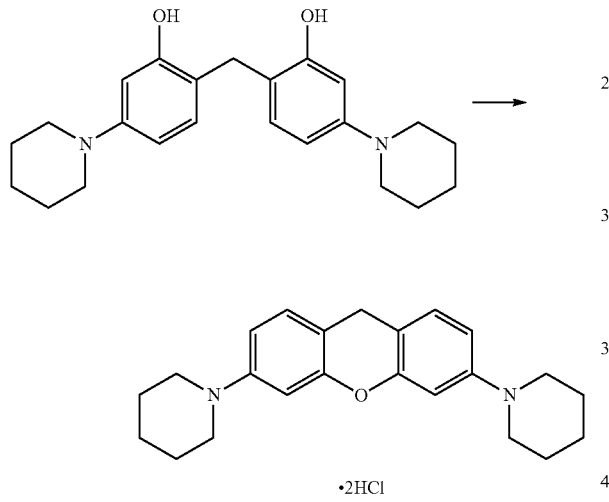

3,6-Bis-piperidino xanthene dihydrochloride $H_2SO_4$ (900 μl, 98%) was added to water (100 μl) and the mixture cooled to room temperature. 5,5'-Bis-piperidino-2, 2'-methandiyl-di-phenol (350 mg, 0.956 mmol) was added portion wise with stirring. The mixture was then heated at 140° C. for 3 h under nitrogen. The resulting solution was cooled to room temperature before the addition of ice water (5 cm³). The mixture was neutralised by the slow addition of sodium hydroxide (40%) keeping the temperature below 20° C. The resulting pink precipitate was collected by filtration, washed with water (2×5 cm³). The intermediate was added to a solution of methanol (5 cm³) and HCl (600 μl, 32%) and stirred for 30 min until homogeneous. The solvent was removed under reduced pressure and the solid dried under vacuum overnight to give the product as a purple solid (298 mg, 74%).

$\delta_H$ (250 MHz, DMSO-$d_6$): 7.73 (2H, s, ArH), 7.65 (2H, d, J=8 Hz, ArH), 6.47 (2H, d, J=8 Hz, ArH), 4.12 (2H, s, $CH_2$), 3.64-3.47 (8H, m, $4CH_2$), 2.20-1.89 (8H, m, $4CH_2$), 1.77-1.57 (4H, m, $2CH_2$); $\nu_{max}$ (KBr)/cm$^{-1}$: 2951, 2522, 1613, 1504, 1479, 1447, 1412, 1300, 1272, 1225, 1198, 1154, 1119; m/z (ESI): 349.23 (100%, [M–HCl$_2$]$^+$).

Synthesis 26

2,6,10-tris-diethylamino-4,8,12-trioxatrianguleum hexafluorophosphate

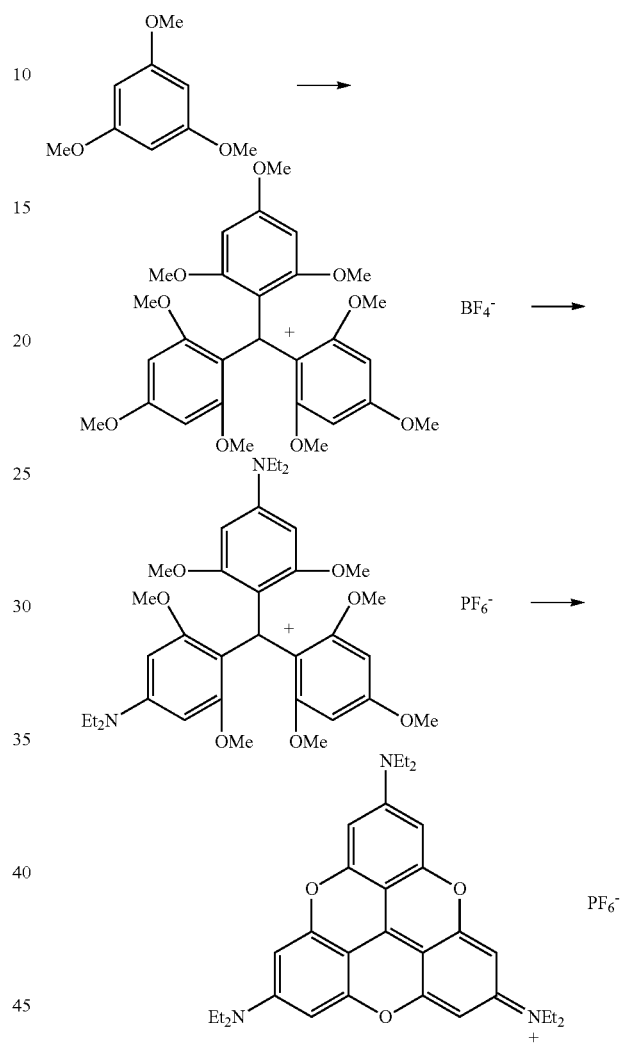

Laursen, B. W., Krebs, F. C., Nielsen, M. F., Bechgaard, K., Christensen, J. B., Harrit, N., *Journal of the American Chemical Society*, 120, 1998, 12255.

Tris-(2,4,6-trimethoxyphenyl)carbenium tetrafluoroborate

PhLi (20 cm³, 35.71 mmol, 1.8 M dibutyl ether) was added to trimethoxybenzene (5.00 g, 29.76 mmol) in dry benzene (20 cm³) under $N_2$. The reaction was stirred at room temperature for 5 days. Diethyl carbonate (1.17 g, 9.22 mmol) in benzene (30 cm³) was added and the reaction heated to reflux for 3 days, before being cooled to room temperature. The reaction mixture was poured into NaOH (60 cm³, 1 M). the mixture was extracted with diethyl ether (3×40 cm³) and the combined extracts dried (MgSO$_4$). HBF$_4$ (2.3 cm³, 48%) was added to the solution and the resulting precipitate collected by filtration and dried under vacuum. The solid was dissolved in $CH_3CN$ (30 cm³) and $H_2O$ was added until precipitation of the product occurred. The bulk solution was decanted and the residue dried under vacuum. Column chromatography [1:9 MeOH/DCM (R$_f$ 0.2)] gave the product as a green solid (1.68 g, 28%).

δ$_H$ (250 MHz, CDCl$_3$): 6.04 (6H, s, 6ArH), 3.97 (9H, s, 3OCH$_3$), 3.57 (18H, s, 6OCH$_3$); ν$_{max}$ (KBr)/cm$^{-1}$: 2941, 1594, 1560, 1474, 1420, 1260, 1229, 1166, 1118, 1084, 1060, 1022; m/z (ESI): 513.21 (100%, [M−HBF$_4$]$^+$).

Tris(4-diethylamino-2,6-dimethoxyphenyl) carbenium hexafluorophosphate

Tris-(2,4,6-trimethoxyphenyl)carbenium tetrafluoroborate (270 mg, 0.450 mmol) was dissolved in NMP (3 cm$^3$). Diethylamine (7.56 g, 0.103 mol) was added and the reaction stirred at room temperature for 9 days. The mixture was then poured into an aqueous solution of KPF$_6$ (20 cm$^3$, 0.2 M). The mixture was then stirred at room temperature for 1 h, collected by filtration and dried under vacuum to give the product as a green/blue solid (295 mg, 84%)

δ$_H$ (250 MHz, CDCl$_3$): 5.71 (6H, s, 6ArH), 3.60-3.21 (30H, m, 6OCH$_3$ and 6CH$_2$), 1.24 (18H, t, J=7 Hz, 6CH$_3$); δ$_c$ (100 MHz, CDCl$_3$): 163.3, 153.9, 114.9, 88.4, 56.0, 45.2, 13.0 (1 carbon missing); ν$_{max}$(KBr)/cm$^{-1}$: 2974, 1595, 1507, 1458, 1386, 1340, 1269, 1124, 1076, 843; m/z (ESI): 636.40 (100%, [M−HPF$_6$]$^+$).

2,6,10-Tris-diethylamino-4,8,12-trioxatrianguleum hexafluorophosphate

Tris(4-diethylamino-2,6-dimethoxyphenyl) carbenium hexafluorophosphate (250 mg, 0.32 mmol) and LiI (428 mg, 3.20 mmol) were added to NMP (25 cm$^3$). The mixture was heated to 170° C. for 4 h under N$_2$. The reaction was allowed to cool to room temperature overnight before being poured into an aqueous solution of KPF$_6$ (125 cm$^3$, 0.2 M). The resulting orange precipitate was collected by filtration, and then dissolved in DCM (100 cm$^3$). The solution was washed with an aqueous solution of KPF$_6$ (2×30 cm$^3$, 0.2 M), dried (Na$_2$SO$_4$) and the solvent removed. Column chromatography [1:2 EtOAc/DCM (R$_f$ 0.35)] gave the product as an orange solid (96 mg, 47%).

δ$_H$ (250 MHz, CDCl$_3$): 6.45 (6H, s, 6ArH), 3.53 (12H, q, J=7 Hz, 6CH$_2$), 1.24 (18H, t, J=7 Hz, 6CH$_3$); δ$_c$ (100 MHz, CDCl$_3$): 155.8, 150.3, 94.3, 94.2, 46.0, 12.3; ν$_{max}$ (KBr)/cm$^{-1}$: 2977, 1647, 1605, 1509, 1446, 1349, 1281, 1139, 843; m/z (ESI): 498.27 (100%, [M−HPF$_6$]$^+$).

Synthesis 27

3-Diethylamino-7-dimethylaminophenazinium chloride

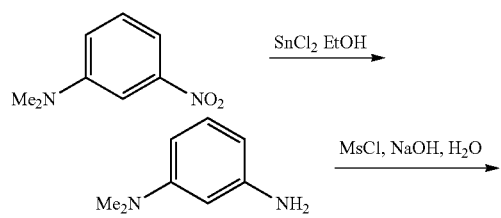

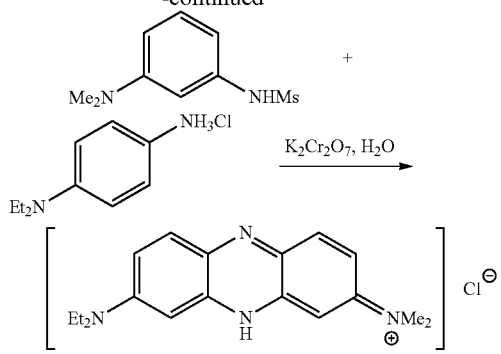

3-Diethylamino-7-dimethylaminophenazinium chloride

Adapted from D. F. Gloster, L. Cincotta, J. W. Foley, *J. Heterocyclic Chem.*, 36, 1999, 25.

N,N-diethyl-1,4-phenylenediamine (1.00 g, 6.17 mmol) was added slowly to dilute HCl (700 µl, 32%) in H$_2$O (100 cm$^3$). The mixture was stirred until it was homogeneous. N-[3-(dimethylamino)phenyl]methanesulphonamide (1.32 g, 6.17 mmol) in methanol (60 cm$^3$) was added, followed by a saturated aqueous solution of potassium dichromate (2 cm$^3$). The mixture refluxed for 15 min. The mixture was cooled and diluted with water (200 cm$^3$), acidified with hydrochloric acid (1M) and then extracted with chloroform (6×30 cm$^3$). The combined extracts were dried over sodium sulphate, filtered and the solvent removed under reduced pressure. Column chromatography (1:9 methanol/dichloromethane) gave the target material as a green solid (451 mg, 22%).

δ$_H$ (250 MHz, CDCl$_3$): 7.85 (2H, d, J=10 Hz, 2ArH), 7.30-7.25 (2H, m, 2ArH), 6.97 (2H, s, 2ArH), 3.51 (4H, q, J=7 Hz, 2CH$_2$), 3.13 (6H, s, 2CH$_3$), 1.26 (6H, J=7 Hz, 2CH$_3$); m/z (ESI): 295 (26%, [M−Cl]$^+$), 324 (100%).

Synthesis 28

3-Diethylamino-7-dimethylaminooxazinium perchlorate

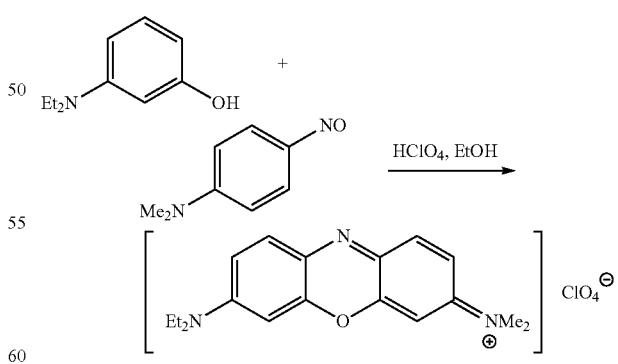

3-Diethylamino-7-dimethylaminooxazinium perchlorate

Adapted from a procedure by: A. Kanitz, H, Hartmann, *Eur, J, Org, Chem.*, 1999, 923.

3-Diethylaminophenol (1.10 g, 6.67 mmol), N,N-dimethyl-4-nitrosoaniline (1.00 g, 6.67 mmol) and perchloric acid (1 cm$^3$) were heated together in ethanol (30 cm$^3$) for 5 min. The reaction was allowed to cool to room temperature. The resulting solid was collected by filtration and dried under vacuum overnight. Column chromatography (1:9 methanol/dichloromethane) gave the product as a green solid (184 mg, 7%).

$\delta_H$ (250 MHz, CDCl$_3$): 7.76-7.71 (2H, m, 2ArH), 7.19-7.14 (2H, m, 2ArH), 6.98-6.95 (2H, m, 2ArH), 3.75 (4H, q, J=7 Hz, 2CH$_2$), 3.43 (6H, s, 2CH$_3$), 1.39 (6H, J=7 Hz, 2CH$_3$); m/z (ESI): 296 (100%, [M−Cl]).

Example 2

Activity and Therapeutic Index

In Vitro Assay for Establishing B50

This is described in detail in WO 96/30766. Briefly, a fragment of tau corresponding to the core repeat domain, which has been adsorbed to a solid phase substrate, is able to capture soluble full-length tau and bind tau with high affinity. This association confers stability against proteolytic digestion of the aggregated tau molecules. The process is self-propagating, and can be blocked selectively by prototype pharmaceutical agents.

More specifically, truncated tau (residues 297-390; dGA) diluted in carbonate buffer (pH 9.6) was bound to the assay plate, and full-length tau (T40) was added in the aqueous phase. The aqueous phase binding buffer contained 0.05% Tween-20 and 1% gelatine in phosphate-buffered saline (pH7.4). Bound tau was detected using mAb 499 that recognises an N-terminal epitope within the aqueous phase full-length tau but that fails to recognise the solid phase-bound truncated tau fragment.

The concentration of compound required to inhibit the tau-tau binding by 50% is referred to as the B50 value.

Cell-Based Assay for Establishing EC50

The process is described in more detail in WO 02/055720. In essence, fibroblast cells (3T6) express full-length tau ("T40") under control of an inducible promotor, and low constitutive levels of the PHF-core tau fragment (12 kD fragment). When T40 expression is induced, it undergoes aggregation-dependent truncation within the cell, N-terminally at ~αα 295 and C-terminally at ~αα 390, thereby producing higher levels of the 12 kD PHF-core domain fragment. Production of the 12 kD fragment can be blocked in a dose-dependent manner by tau-aggregation inhibitors. Indeed the quantitation of inhibitory activity of compounds with respect to proteolytic generation of the 12 kD fragment within cells can be described entirely in terms of the same parameters which describe inhibition of tau-tau binding in vitro. That is, the extent of proteolytic generation of the 12 kD fragment within cells is determined entirely by the extent to tau-tau binding through the repeat domain. The availability of the relevant proteases within the cell is non-limiting.

Results are expressed as the concentration at which there is a 50% inhibition of generation of the 12 kD fragment. This is referred to as the EC50 value.

Toxicity in Cells

LD50 and Therapeutic Index (RxI)

Toxicity of the compounds described herein was assessed in the cell based assay used to assess EC50. Toxicity was measured by cell numbers after 24 hrs exposure to the compound using a lactate dehydrogenase assay kit TOX-7 (Sigma Biosciences) according to the manufacturer's instructions after lysis of remaining cells. Alternatively a kit from Promega UK (CytoTox 96) was used, again according to the manufacturer's instructions.

The therapeutic index (RxI) was calculated as follows: RxI=LD50/EC50.

TABLE 2

Activity and Therapeutic Index of Compounds A to O

| Compound | B50 (µM) | EC50 (µM) | LD50 (µM) | RxI |
|---|---|---|---|---|
| MTC | 218 ± 20.1 (6) | 0.59 ± 0.04 (69) | 65.0 ± 5.0 (38) | 110 |
| DMMTC | 3.4 ± 0.2 (2) | 0.04 ± 0.004 (22) | 2.7 ± 1.2 (6) | 67 |
| DMAXC | 38.5 ± 6.9 (3) | 0.2 ± 0.11 (2) | 39.2 ± 10.5 (5) | 196 |
| A | 33.8 ± 5.2 (3) | 0.0061 ± 0.0024 (9) | 19 ± 2.7 (22) | 3115 |
| B | 254.1 ± 26.4 (3) | 0.0081 ± 0.0035 (9) | 30.8 ± 4.6 (4) | 3802 |
| C | 461 ± 130 (3) | 0.47 | 5.99 ± 2.6 (4) | 13 |
| D | 49.4 ± 7.6 (5) | 0.017 ± 0.01 (4) | 30 ± 3.4 (10) | 1764 |
| E* | 312.1 ± 28.4 (7) | 0.014 ± 0.002 (7) | 15.8 ± 2.8 (16) | 1131 |
|  | 389.6 ± 322.0 (2) | 0.048 ± 0.008 (17) | 19.37 ± 2.3 (7) | 404 |
| F | 260.1 ± 57.1 (3) | 0.042 ± 0.030 (5) | 24.6 ± 6.3 (5) | 586 |
| G | 89.4 ± 15.7 (3) | 0.079 ± 0.024 (6) | 35.8 ± 5.5 (6) | 453 |
| H | NE | 0.054 ± 0.01 (10) | 113 ± 18 (11) | 2093 |
| I•HNO$_3$ | NE | 0.032 ± 0.007 (6) | 20.4 ± 3.5 (8) | 638 |
| J | NE | 0.011 ± 0.006 (5) | 17 ± 3 (10) | 1545 |
| K | NE | 0.23 ± 0.13 (3) | 21.2 ± 12 (3) | 91 |
| L | 21.7 ± 2.7 (3) | 0.30 | 22 ± 8.6 (3) | 73 |
| M | 110.4 ± 6.2 (3) | 0.44 | NT | NT |
| N | 93.1 ± 17 (3) | NT | 136 ± 19.3 (4) | NT |
| O | 190.2 ± 33.2 (3) | 3.9 ± 3.5 (3) | 115 ± 17 (9) | 29 |
| AB | 413.5 | 1.72 ± 1.0 (4) | 78 ± 54 (6) | 45 |
| AC | 129.4 ± 11.9 (3) | 1.43 ± 0.14 (4) | 14.5 ± 8.4 (8) | 34 |
| AD | 126.4 ± 3.0 (3) | 0.35 ± 0.10 (5) | 19 ± 9 (5) | 54 |
| AE | 324.5 ± 87.1 (3) | 0.051 ± 0.012 (5) | 21 ± 8 (7) | 412 |
| AF | 186.7 ± 28.3 (4) | 22 ± 4.2 (5) | 144 ± 67 (10) | 7 |
| AG | 257.1 ± 50.3 (5) | 1.12 ± 0.75 (5) | 13.8 ± 6.2 (8) | 12 |
| AH | 129.4 ± 15.5 (3) | 0.26 ± 0.073 (9) | 121 ± 52 (12) | 465 |
| AI | NE | 16 ± 11 (3) | 280 ± 121 (10) | 17 |
| AJ | NE | 0.37 ± 0.1 (6) | 125 ± 57 (10) | 334 |

TABLE 2-continued

Activity and Therapeutic Index of Compounds A to O

| Compound | B50 (μM) | EC50 (μM) | LD50 (μM) | RxI |
|---|---|---|---|---|
| AK | 284.1 ± 101.2 (5) | 0.64 ± 0.27 (5) | 44 ± 26 (8) | 69 |
| AL | 8.5 ± 0.9 (3) | 0.13 ± 0.07 (4) | 8 ± 4 (6) | 62 |
| AM | 634.1 | 1.1 ± 0.24 (5) | 93 ± 19 (6) | 85 |
| AN | NE | 0.54 ± 0.08 (4) | 167 ± 29 (6) | 309 |

NE = no effect when tested to 500 μM.
NT = not tested
B50, EC50, LD50 values are expressed as mean values (in μM) ± SE, with number of replications in parentheses.
RxI = EC50/LD50.
*results from two different synthetic batches of compound E

REFERENCES

The following references are hereby incorporated by reference in their entirety:
U.S. Pat. No. 3,932,415
DE 65282
JP 2000/344684
WO 96/30766
WO 02/055720
WO02/075318
Albert, *Journal of the Chemical Society* 1947, 244.
Biehringer, *Chemische Berichte* 1894, 27, 3299.
Biehringer, *Journal Fur Praktische Chemie* 1896, 54, 217.
Bondareff, W. et al., 1994, *J. Neuropath. Exper. Neurol.*, Vol. 53, No. 2, pp. 158-164.
Braak et al. (2003) Spectrum of pathology. In Mild cognitive impairment: Aging to Alzheimer's disease edited by Petersen, R. C.; pp. 149-189.
Chamberlin et al. *Journal of Organic Chemistry* 1962, 27, 2263.
Flament et al. *Brain Res.* 1990, 516, 15-19.
Goedert et al., 1989, *EMBO J.*, Vol. 8, pp. 393-399.
Goedert et al., 1989, *Neuron*, Vol. 3, pp. 519-526.
Gloster et al. *J. Heterocyclic Chem.* 1999, 36, 25.
Haley *Journal of Heterocyclic Chemistry* 1977, 14, 683.
Harrington et al. *Dementia* 1994, 5, 215-228.
Hof et al. *Acta Neuropathol.* 1992, 85, 23-30.
Hof et al. *Neurosci. Lett.* 1992, 139, 10-14.
Ikeda et al. *Neurosci. Lett.* 1995, 194, 133-135.
Jakes et al., 1991, *EMBO J.*, Vol. 10, pp. 2725-2729.
Kang et al., 1987, *Nature*, Vol. 325, p. 733.
Kanitz and Hartmann, *Eur, J, Org, Chem.* 1999, 923.
Lai et al., 1995, *Neurobiology of Ageing*, Vol. 16, No. 3, pp. 433-445.
Mena et al., 1995, *Acta Neuropathol.*, Vol. 89, pp. 50-56.
Mena et al., 1996, *Acta Neuropathol.*, Vol. 91, pp. 633-641.
Mukaetova-Ladinska, E. B., et al., 2000, *Am. J. Pathol.*, Vol. 157, No. 2, pp. 623-636.
Muller et al., *Eur. J. Biochem.*, 54, 1975, 267.
Nealey and Driscoll, *J. Hetero. Chem.* 1966, 3, 228.
Novak et al., 1993, *EMBO J.*, Vol. 12, pp. 365-370.
Prostota and Kovtun *Chemistry of Heterocyclic Compounds* 2003, 39, 1537-1538.
Shelanski et al. (1973) *Proc. Natl. Acad. Sci. USA* 1973, 70, 765-768
Wischik et al., 1988, *PNAS USA*, Vol. 85, pp. 4506-4510.
Wischik, et al., 1988, *PNAS USA*, Vol. 85, pp. 4884-4888.
Wischik et al., 1996, *PNAS USA*, Vol. 93, pp. 11213-11218.
Wischik et al., 1997, in "Microtubule-associated proteins: modifications in disease", Eds. Avila, J., Brandt, R. and Kosik, K. S. (Harwood Academic Publishers, Amsterdam) pp. 185-241.
Wischik et al. (in 'Neurobiology of Alzheimer's Disease', 2nd Edition, 2000, Eds.
Dawbarn, D. and Allen, S. J., *The Molecular and Cellular Neurobiology Series*, Bios Scientific Publishers, Oxford.
*Handbook of Pharmaceutical Additives*, 2nd Edition (eds. M. Ash and I. Ash), 2001 (Synapse Information Resources, Inc., Endicott, N.Y., USA).
*Remington's Pharmaceutical Sciences*, 20th edition, pub. Lippincott, Williams & Wilkins, 2000.
*Handbook of Pharmaceutical Excipients*, 2nd edition, 1994.
Uddin, M. J., Marnett L., J., *Organic Letters*, 10, 2008, 4799.
Laursen, B. W., Krebs, F. C., Nielsen, M. F., Bechgaard, K., Christensen, J. B., Harrit, N., *Journal of the American Chemical Society*, 120, 1998, 12255.
Love, S., Bridges, L. R. & Case, C. P., *Brain*, 1995, 118, 119-129 "*Neurofibrillary tangles in Niemann-Pick disease type C*".
Ohmi, K., Kudo, L. C., Ryazantsev, S., et al. *Proceedings of the National Academy of Sciences* 2009, 106, 8332-8337 "*Sanfilippo syndrome type B, a lysosomal storage disease, is also a tauopathy*".
Sergeant, N., Sablonniere, B., Schraen-Maschke, S., et al. *Human Molecular Genetics*, 2001, 10, 2143-2155 "*Dysregulation of human brain microtubule-associated tau mRNA maturation in myotonic dystrophy type 1*", and references therein.
Maurage, C. A., Udd, B., Ruchoux, M. M., et al. *Neurology*, 2005, 65, 1636-1638, "*Similar brain tau pathology in DM2/PROMM and DM1/Steinert disease*".
McKee, A., Cantu, R., Nowinski, C., Hedley-Whyte, E., Gavett, B., Budson, A., Santini, V., Lee, H.-S., Kubilus, C. & Stern, R. (2009) Chronic traumatic encephalopathy in athletes: progressive tauopathy after repetitive head injury. Journal of Neuropathology & Experimental Neurology 68, 709-735

The invention claimed is:

1. A method of treatment of a tauopathy condition or a disease of tau protein aggregation in a patient in need thereof comprising administering to the patient a compound of formula (I):

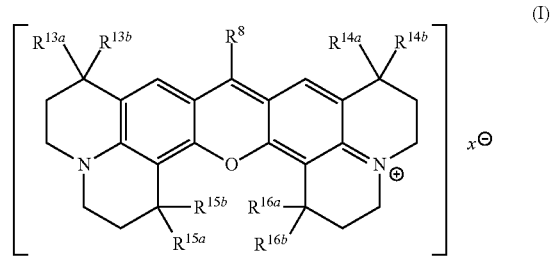

wherein:

X⁻ is a counter ion;

—R⁵ is independently —H, or saturated C₁₋₆alkyl, which is unsubstituted or substituted with one or more substituents —R⁵ᴬ, or phenyl, which is unsubstituted or substituted with one or more substituents —R⁵ᴬ;

each —R⁵ᴬ is independently selected from —F, —Cl, —Br, —I, —OH, —OR⁶, —SH, —SR⁶, —CN, —NO₂, —NH₂, —NHR⁶, —NR⁶₂, —NHC(=O)R⁶, —NR⁶C(=O)R⁶, —C(=O)OR⁶, —OC(=O)R⁶, —C(=O)NH₂, —C(=O)NHR⁶, and —C(=O)NR⁶₂, —C(=O)R⁶, —C(=O)OH, —S(=O)R⁶, —S(=O)₂R⁶, and —S(=O)₂OH;

each —R⁶ is independently saturated aliphatic C₁₋₄alkyl, phenyl, or benzyl;

—R¹³ᵃ, —R¹³ᵇ, —R¹⁴ᵃ, —R¹⁴ᵇ, —R¹⁵ᵃ, —R¹⁵ᵇ, —R¹⁶ᵃ, and —R¹⁶ᵇ are each independently selected from H and saturated aliphatic C₁₋₄ alkyl.

2. A method according to claim 1, wherein X⁻ is selected from the group consisting of: NO₃⁻, ClO₄⁻, F⁻, Cl⁻, Br⁻, I⁻, ZnCl₃⁻, FeCl₄⁻ and PF₆⁻.

3. A method according to claim 1, wherein —R⁵ is independently —H, or saturated aliphatic C₁₋₆alkyl, which is unsubstituted or substituted with one or more substituents —R⁵ᴬ.

4. A method according to claim 1, wherein —R⁵ is saturated aliphatic C₁₋₄alkyl, which is unsubstituted or substituted with one or more substituents —R⁵ᴬ.

5. A method according to claim 4, wherein each —R⁵ᴬ is independently selected from —F, —Cl, —Br, or —I.

6. A method according to claim 4, wherein —R⁵ is —CF₃.

7. A method according to claim 1, wherein —R⁵ is phenyl, which is substituted with one or more substituents —R⁵ᴬ.

8. A method according to claim 7, wherein each —R⁵ᴬ is independently selected from NH₂ and NO₂.

9. A method according to claim 4, wherein —R⁵ is -Et.

10. A method according to claim 1, wherein the compound is a compound of formula (Ic):

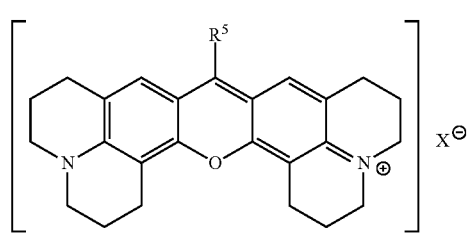

(Ic)

wherein X and R⁵ are as defined for the compounds of formula (I).

11. A method according to claim 1, wherein the compound is selected from the group consisting of:

| Compound | Structure and Name |
|---|---|
| A | 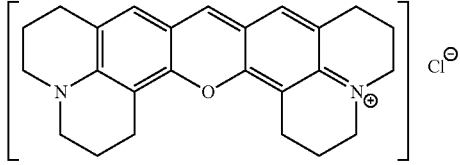<br>2,3,6,7,12,13,16,17-Octahydro-1H,5H,11H,15H-diquinolizino[1,9-bc: 1′,9′-hi] xanthylium chloride |
| B | 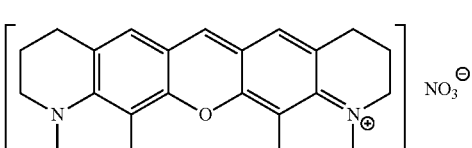<br>2,3,6,7,12,13,16,17-Octahydro-1H,5H,11H,15H-diquinolizino[1,9-bc: 1′,9′-hi] xanthylium nitrate |
| C | 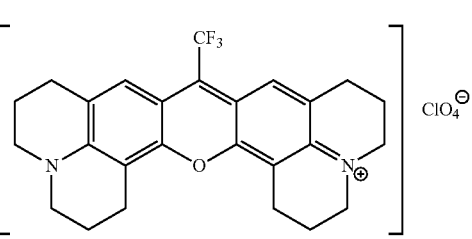<br>8-(Trifluoromethyl)-2,3,5,6,11,12,14,15-octahydro-1H,4H,10H,13H-diquinolizino[9,9a,1-bc; 9′,9a′1′-hi] xanthylium perchlorate |
| D | 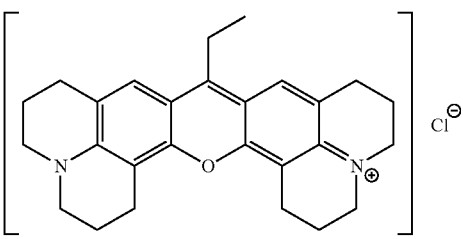<br>8-Ethyl-2,3,6,7,12,13,16,17-octahydro-1H,5H,11H,15H-diquinolizino[1,9-bc; 1′,9′-hi] xanthylium chloride |
| AE | 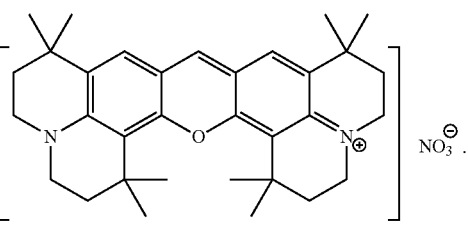<br>1,1,7,7,11,11,17,17-Octamethyl-2,3,6,7,12,13,16,17-octahydro-1H,5H,11H,15H-diquinolizino [1,9-bc: 1′,9′-hi] xanthylium nitrate |

12. A method according to claim 1, wherein the compound is provided in the form of a dosage unit comprising the compound in an amount of from 20 to 300 mg and a pharmaceutically acceptable carrier, diluent, or excipient.

13. A method according to claim 1, wherein the treatment comprises administration of the compound according to one of the following dosage regimes: about 50 or about 75 mg, 3 or 4 times daily; or about 100 or about 125 mg, 2 times daily.

14. A method according to claim 1, wherein the treatment comprises oral administration of the compound.

15. A method according to claim 1, wherein the treatment further comprises treatment with at least one of the following: a cholinesterase inhibitor; Donepezil, Rivastigmine, or Galantamine; an NMDA receptor antagonist; Memantine; a muscarinic receptor agonist; an inhibitor of amyloid precursor protein processing to beta-amyloid.

16. A method of reversing or inhibiting the aggregation of tau protein comprising contacting the aggregate or protein with a compound as defined in claim 1.

17. A method of regulating the aggregation of a tau protein in the brain of a mammal, which aggregation is associated with a disease of tau protein aggregation, comprising the step of administering to said mammal a therapeutically effective amount of a compound as defined in claim 1.

18. A method of inhibiting production of protein aggregates in the brain of a mammal, comprising the step of administering to said mammal a therapeutically effective amount of a compound as defined in claim 1.

19. A method of treatment of a tauopathy condition in a patient comprising administering to said patient a compound as defined in claim 1.

20. A method of treatment of a disease of tau protein aggregation in a patient comprising administering to said patient a compound as defined in claim 1.

21. A method of treatment of Alzheimer's disease (AD), Pick's disease, Progressive Supranuclear Palsy (PSP), fronto-temporal dementia (FTD), parkinsonism linked to chromosome 17 (FTDP-17), disinhibition-dementia-parkinsonism-amyotrophy complex (DDPAC), pallido-ponto-nigral degeneration (PPND), Guam-ALS syndrome, pallido-nigro-luysian degeneration (PNLD), cortico-basal degeneration (CBD), Dementia with Argyrophilic grains (AgD), Dementia pugilistica (DP), Down's Syndrome (DS), Dementia with Lewy bodies (DLB) Subacute sclerosing panencephalitis (SSPE), MCI, Neumann Pick disease, type C(NPC), Sanfilippo syndrome type B, mucopolysaccharidosis III B (MPS III B), myotonic dystrophies (DM), DM1 or DM2, or chronic traumatic encephalopathy (CTE) in a patient, comprising administering to said patient a compound as defined in claim 1.

22. A method of treatment of Alzheimer's disease (AD) in a patient, comprising administering to said patient a compound as defined in claim 1.

* * * * *